US009934367B2

(12) United States Patent
Chen et al.

(10) Patent No.: US 9,934,367 B2
(45) Date of Patent: Apr. 3, 2018

(54) METHOD OF CHARACTERIZING CHEMICAL COMPOSITION OF CRUDE OIL FOR PETROLEUM PROCESSING

(71) Applicant: Aspen Technology, Inc., Burlington, MA (US)

(72) Inventors: Chau-Chyun Chen, Lexington, MA (US); HuiLing Que, Shanghai (CN)

(73) Assignee: Aspen Technology, Inc., Bedford, MA (US)

( * ) Notice: Subject to any disclaimer, the term of this patent is extended or adjusted under 35 U.S.C. 154(b) by 0 days.

(21) Appl. No.: 13/740,095

(22) Filed: Jan. 11, 2013

(65) Prior Publication Data

US 2013/0185044 A1 Jul. 18, 2013

Related U.S. Application Data

(60) Provisional application No. 61/586,268, filed on Jan. 13, 2012, provisional application No. 61/644,792, filed on May 9, 2012.

(51) Int. Cl.
*G06F 19/00* (2018.01)
*G01N 33/28* (2006.01)
*G06Q 50/02* (2012.01)

(52) U.S. Cl.
CPC ......... *G06F 19/70* (2013.01); *G01N 33/2823* (2013.01); *G01N 33/2829* (2013.01); *G06F 19/704* (2013.01); *G06Q 50/02* (2013.01)

(58) Field of Classification Search
None
See application file for complete search history.

(56) References Cited

U.S. PATENT DOCUMENTS 5,223,714 A   6/1993 Maggard
5,699,269 A  12/1997 Ashe et al.
(Continued)

FOREIGN PATENT DOCUMENTS

EP   2 584 381 A1   4/2013
JP   10-185875      7/1998
(Continued)

OTHER PUBLICATIONS

Peng, "Molecular modelling of petroleum processes," dissertation, University of Manchester, 1999.*
(Continued)

*Primary Examiner* — G. Steven Vanni
(74) *Attorney, Agent, or Firm* — Hamilton, Brook, Smith & Reynolds, P.C.

(57) ABSTRACT

A computer method of characterizing chemical composition of crude oil and crude oil blends, includes determining respective segment type and segment number range of selected classes of hydrocarbon constituent molecules based on physical and chemical property data on each class of hydrocarbon constituent molecules and on crude oil physical and chemical property data. The method determines relative ratio of each class of hydrocarbon constituent molecules that forms a chemical composition representative of the subject crude oil, and therefrom characterizes chemical composition of the subject crude oil. The method/system displays to an end-user, the characterized chemical composition of the subject crude oil. Based on the identified distribution functions and the relative ratio of each class of hydrocarbon constituent molecules, the method estimates chemical composition of the crude oil. Estimates of physical and chemical properties of the crude oil are then based on the estimated chemical composition.

29 Claims, 49 Drawing Sheets

(56) References Cited

U.S. PATENT DOCUMENTS

| | | | |
|---|---|---|---|
| 5,808,180 | A | 9/1998 | Roussis et al. |
| 6,662,116 | B2 | 12/2003 | Brown |
| 8,546,146 | B2 | 10/2013 | Butler et al. |
| 2003/0195708 | A1 | 10/2003 | Brown |
| 2008/0248967 | A1 | 10/2008 | Butler et al. |
| 2009/0105966 | A1 | 4/2009 | Brown et al. |
| 2013/0185044 | A1 | 7/2013 | Chen et al. |
| 2016/0162664 | A1 | 6/2016 | Watanasiri et al. |

FOREIGN PATENT DOCUMENTS

| | | |
|---|---|---|
| JP | H11-508363 A | 7/1999 |
| JP | 2005-512051 A | 4/2005 |
| JP | 2008-513562 A | 5/2008 |
| WO | WO 1997/01096 A | 1/1997 |
| WO | WO 2006/030218 A1 | 3/2006 |
| WO | WO 2003/048759 A1 | 6/2013 |
| WO | WO 2013/106755 | 7/2013 |
| WO | WO 2016/178763 | 11/2016 |

OTHER PUBLICATIONS

Albahri, T. A., "Molecularly Explicit Characterization Model (MECM) for Light Petroleum Fractions," *Ind. Eng. Chem. Res.*, 44:9286-9298 (2005).

Eckert, E. and Vanek, T., "New Approach to the Characterization of Petroleum Mixtures Used in the Modelling of Separation Processes," *Computers & Chem. Eng.*, 30:343-356 (2005).

Gross, J. and Sadowski, G., "Perturbed-Chain SAFT: An Equation of State Based on a Perturbation Theory for Chain Molecules," *Ind. Eng. Chem. Res.* 40: 1244-1260 (2001).

Gross, J. et al., "Modeling Copolymer Systems Using the Perturbed-Chain SAFT Equation of State," *Ind. Eng. Chem. Res.* 42: 1266-1274 (2003).

Jaffe, S. B., et al., "Extension of Structure-Oriented Lumping to Vacuum Residua," *Ind. Eng. Chem. Res.*, 44:9840-9852 (2005).

Pyl, S. P., et al., "Modeling the Composition of Crude Oil Fractions Using Constrained Homologous Series," *Ind. Eng. Chem. Res.* 50: 10850-10858 (2011).

Quann, R. J. and Jaffe, S. B., "Structured-Oriented Lumping: Describing the Chemistry of Complex Hydrocarbon Mixtures," *Ind. Eng. Chem. Res.*, 31: 2483-2497 (1992).

Saine Aye, M. M. and Zhang, N., "A Novel Methodology in Transforming Bulk Properties of Refining Streams into Molecular Information," *Chem. Eng. Sci.*, 60: 6702-6717 (2005).

Klein, et al., "Molecular Modeling in Heavy Hydrocarbon Conversions," *Taylor & Francis*, (2006).

Wu, Y. and Zhang, N., "Molecular Characterization of Gasoline and Diesel Streams," *Ind. Eng. Chem. Res.*, 49: 12773-12782 (2010).

International Preliminary Report on Patentability for Int'l Application No. PCT/US2013/021294 entitled: Method of Characterizing Chemical Composition of Crude Oil for Petroleum Refining Processing; dated Jul. 24, 2014.

Notification of Transmittal of the International Search Report and The Written Opinion of the International Searching Authority, or the Declaration, PCT/US2016/025929, "Method to Represent Metal Content in Crude Oils, Reactor Feedstocks, and Reactor Products", dated Jul. 6, 2016.

Sebor, G., et al., "Effect of the Type of Organometallic Iron and Copper Compounds on the Determination of Both Metals in Petroleum Samples by Flame Atomic-absorption Spectroscopy", Analyst, 107:1350-1355 (Nov. 1982).

McKenna, A., et al. "Unprecedented Ultrahigh Resolution FT-ICR Mass Spectrometry and Parts-Per-Billion Mass Accuracy Enable Direct Characterization of Nickel and Vanadyl Porphyrins in Petroleum from Natural Seeps," *Energy Fuels*, 28: 2454-2464 (2014).

NIST ThermoData Engine (NIST Standard Reference Database 103b, http://trc.nist.gov/tde.html) (several pages from website, printed Feb. 17, 2016).

Oil & Gas Journal Databook, 2006 Edition, PennWell Corporation, Tulsa, Oklahoma, 2006 (cover pages).

Poling, Bruce, E., et al., "Viscosity", *The Properties of Gases and Liquids* McGraw-Hill, 5$^{th}$ Ed., Chapter 9, pp. 9.77-9.90 (2001).

Riazi, M.R., "Characterization and Properties of Petroleum Fractions", *Petroleum Fractions*, ASTM International, Chapter 3, pp. 111-119 (2005).

Watt, Murray, R., et al., "Crude Assay", *Practical Advances in Petroleum Processing*, vol. 1, Chapter 3, Chang S. Hsu & Paul R. Robinson, Eds., Springer, pp. 103-116, (2006).

An, A. and Hao, X., "Generalized Predictive Control for a Precise Crude Oil Blending Process," *Proceedings of the IEEE, International Conference on Automation and Logistics* (2008). p. 7-12.

Hudebine, D., et al.," Statistical Reconstruction of Gas Oil Cuts," *Oil & Gas Science Technology*, 66(3): 461-477 (2009).

Notification of Transmittal of the International Search Report and the Written Opinion of the International Searching Authority, or the Declaration for PCT/US2013/021294, dated Mar. 28, 2013.

Verstraete, J.J., et al., "Molecular Reconstruction of Heavy Petroleum Residue Fractions," *Chemical Engineering Science*, 65(1): 304-312 (2010).

Riazi, M. R.; "Characterization and Properties of Petroleum Fractions;" *Chapter 1—Introduction*, pp. 1-29; American Society for Testing and Materials (2005).

\* cited by examiner

| Structure | —CH₃ | —CH₂— | ⊥ |
|---|---|---|---|
| Formula | CH₃ | CH₂ | CH |
| Structure | ⊥ | ⬡ | ⬡ |
| Formula | C | C₆H₁₂ | C₄H₆ |
| Structure | ⬠ | ⬠ | ⬡ |
| Formula | C₅H₁₀ | C₃H₄ | C₆H₆ |
| Structure | ⬡ | | |
| Formula | C₄H₂ | | |

| SEGMENTS | ⬡ | ⌒ | -CH$_2$- | -CH$_3$ |
|---|---|---|---|---|
| PROBABLE NUMBER IN MOLECULAR SPECIES | 1 | 0~6 | 0~48 | 0, 1, 2, 3, 4, 5, 6, 7 |
| STRUCTURE OF MOLECULAR SPECIES | | | | |

(n = 0~48, TOTAL SIDE CHAIN CARBON NO. UP TO 50)
NOTE THAT HERE STRUCTURES FOR LINEAR RING COMPOUNDS ARE SYMBOLIC ONES.

FIG. 3A

| SEGMENTS | ⬡ | ⟩ | ⌬ | ⌬ | -CH$_2$- | -CH$_3$ |
|---|---|---|---|---|---|---|
| PROBABLE NUMBER IN MOLECULAR SPECIES | 1 | 0~1 | 0~6 | 0~6 | 0~48 | 0, 1, 2, 3, 4, 5, 6, 7 |
| STRUCTURE OF MOLECULAR SPECIES | (chemical structures shown) | | | | | |

(n = 0~48, TOTAL SIDE CHAIN CARBON NO. UP TO 50)
NOTE THAT HERE STRUCTURES FOR LINEAR RING COMPOUNDS ARE SYMBOLIC ONES.

FIG. 4A

| SEGMENTS | ⬡ | ⟩ | ⟨ | ⟩ | -CH$_2$- | -CH$_3$ |
|---|---|---|---|---|---|---|
| PROBABLE NUMBER IN MOLECULAR SPECIES | 1 | 0~1 | 0~6 | 0~6 | 0~48 | 0, 1, 2, 3, 4, 5, 6, 7 |
| STRUCTURE OF MOLECULAR SPECIES | | | | | | |

(n = 0~48, TOTAL SIDE CHAIN CARBON NO. UP TO 50)
NOTE THAT HERE STRUCTURES FOR LINEAR RING COMPOUNDS ARE SYMBOLIC ONES.

| SEGMENTS | ⬡ | ⌬ | ⌬ | -CH$_2$- | -CH$_3$ |
|---|---|---|---|---|---|
| PROBABLE NUMBER IN MOLECULAR SPECIES | 1 | a=0~6 | b=6-a | 0, 6, 12, 18, 24, 30, 36, 42, 48, 54 | 0, 6 |

(n = 1~9)
NOTE THAT HERE STRUCTURES FOR LINEAR RING COMPOUNDS ARE SYMBOLIC ONES.

FIG. 4D

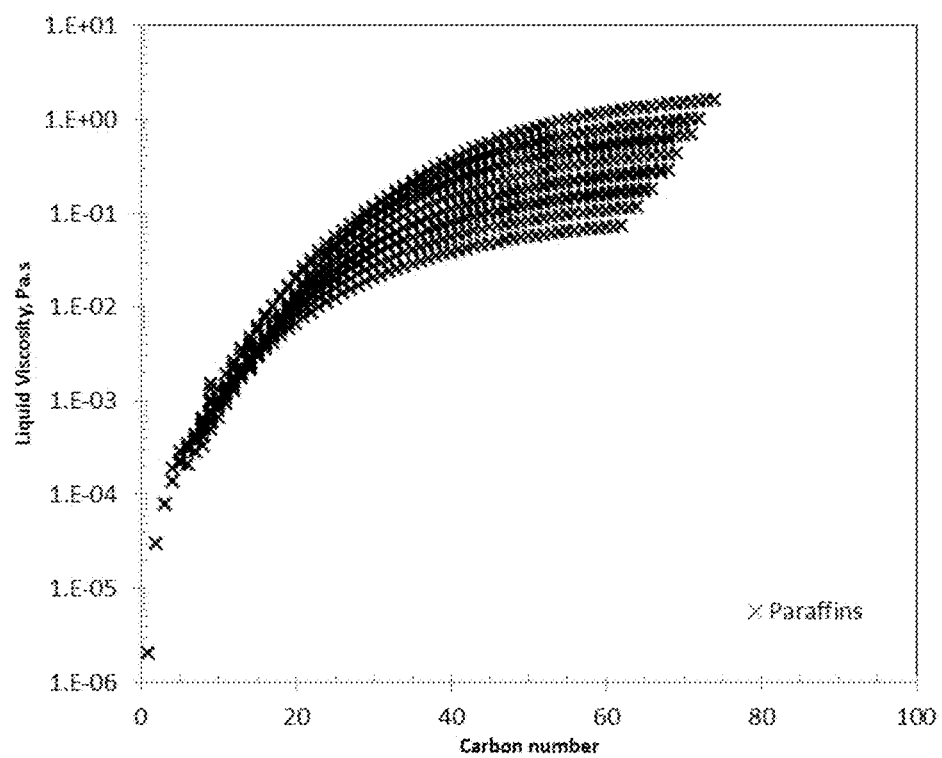
FIG. 7A-1
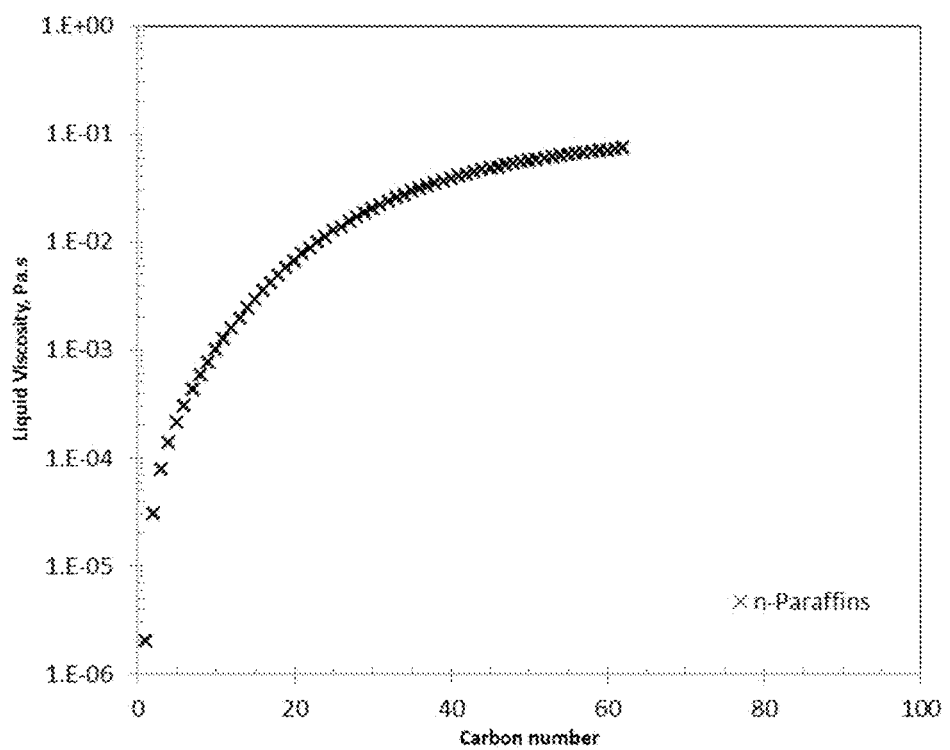
FIB. 7A-2

METHOD OF CHARACTERIZING CHEMICAL COMPOSITION OF CRUDE OIL FOR PETROLEUM PROCESSING

RELATED APPLICATIONS

This application claims the benefit of U.S. Provisional Application No. 61/644,792, filed on May 9, 2012 and U.S. Provisional Application No. 61/586,268, filed on Jan. 13, 2012.

The entire teachings of the above applications are incorporated herein by reference.

BACKGROUND OF THE INVENTION

Each crude oil type has unique molecular characteristics. Crude oil assaying is the physical and chemical evaluation of crude oil feedstock by petroleum testing laboratories. Assays vary considerably throughout the industry, from just a handful of key properties for the whole crude to a full set of physical, chemical, and chromatographic measurements on distilled or blended fractions and residues of the crude oil. See M. Unavane, Statistical Tools for Managing and Manipulating Crude Oil Data, Exploration & Production, 2010, 8:135-138 (hereinafter "Unavane"). Results of crude oil assay testing provide extensive hydrocarbon analysis data for refiners, oil traders and producers. For example, assay data help refineries determine if a specific crude oil feedstock is compatible with a particular petroleum refinery or if the crude oil could cause yield, quality, production, environmental, or other problems.

The determination of a detailed crude oil assay is a lengthy, tedious and costly process. See M. Watt, S. Roussis, Crude Assay, Practical Advances in Petroleum Processing, Chapter 3, 103-116 (2006) (hereinafter "Watt"). The conventional approach to perform an assay consists of a limited set of measurements on the crude oil and its fractions. See Unavane. Most often only a few boiling points, densities, and other physical or chemical property measurements are available for selected distilled fractions or the whole crude oil. Densities are typically reported in American Petroleum Institute (API) gravity degrees. API gravity is a measure of how heavy or light petroleum liquid is compared to water, which has a defined API gravity of 10 degrees. A crude oil having a higher API gravity is lighter (less dense) than water. See Oil & Gas Journal Databook, 2006 Edition, PennWell Corporation, Tulsa, Okla., 2006 (hereinafter "Oil & Gas Databook").

Due to limited available data, it is necessary for crude oil assay experts to predict or estimate missing properties to meet various business needs, such as refinery planning and scheduling and refinery process simulation. Typically, lower order polynomial expressions are used for interpolation, and an arithmetic probability function is used for extrapolation of boiling point curves. See Aspen Technology, Inc., Aspen HYSYS, v7.3, Burlington, Mass. Analytical approaches include the prediction of crude oil properties by correlating the data obtained by rapid surrogate measurements (typically spectroscopic measurements) to existing crude assays. See Watt; J. M. Brown, Method for Analyzing An Unknown Material as A Blend of Known Materials Calculated So As to Match Certain Analytical Data and Predicting Properties of the Unknown Based on the Calculated Blend, U.S. Pat. No. 6,662,116 B2, Dec. 9, 2003. See also J. M. Brown et al., Estimating Detailed Compositional Information from Limited Analytical Data, US Patent Application Publication US2009/0105966 A1, Apr. 23, 2009.

Statistically derived predictive methods have also been extensively used in the industry for the prediction or estimation of crude oil properties and assays. See Unavane. The issues with statistical methods are 1) in cases data are scarce or sporadic, it may not be possible to develop statistically meaningful models, 2) in cases data are abundant but with inconsistent data quality including high uncertainties, the quality of models or correlations can be questionable, 3) in cases data are abundant and with adequate quality, the complexity of petroleum mixtures still makes the statistical model development very difficult and highly subjective especially when developing interrelationships between different properties, and 4) in cases data are not available, there is nothing statistical methods could offer.

Crude oil assays are often used to generate a limited number of "pseudocomponents" or "hypothetical components" and their compositions are then used to represent petroleum mixtures for the purpose of planning, scheduling, and process simulation. These "pseudocomponents," derived from the true boiling point (TBP) characterization curve as "micro boiling point cuts," are not real hydrocarbon components or molecules in the petroleum mixtures. See M. R. Riazi, Characterization and Properties of Petroleum Fractions, $1^{st}$ Ed., ASTM, West Conshohocken, Pa., USA, 2005, p. 111-112. These pseudocomponents are defined to mimic a fraction of the crude assay, that is, the pseudocomponent is defined by a specific boiling point range and by a range of specific gravity, or by a group of pure components from a hydrocarbon family with a specific range of carbon number. In contrast, a petroleum fraction (e.g., fuel oil) is a mixture of real hydrocarbon molecules obtained from fractional distillation of crude oil. A disadvantage of using pseudo-component is that their physical and chemical properties need to be estimated by often inadequate empirical methods.

Therefore, there is a need for an improved crude oil assay method for estimation of crude oil properties and assays.

SUMMARY OF THE INVENTION

The invention generally is directed to a method of assaying by characterizing the chemical composition of crude oil using a selected set of hydrocarbon constituent components or molecules that form a chemical composition representative of the given crude oil or petroleum fraction. The resulting relative amounts of hydrocarbon constituent components or molecules represent an estimate of the actual chemical makeup of the crude oil. The chemical compositions of these hydrocarbon constituent molecules are then used as the molecular basis to interpolate and extrapolate various chemical and physical properties for the crude oil.

In one embodiment, a method of characterizing chemical composition of crude oil includes, given a crude oil having certain crude oil characterization data, in a processor, determining respective segment type and segment number range of selected classes of hydrocarbon constituent molecules based on physical and chemical property data on each class of hydrocarbon constituent molecules and on crude oil physical and chemical property data. Determining segment type and segment number range in a processor can include the processor obtaining pre-specified probability distribution functions or the processor determining probability distribution functions and associated parameters for the segments for each class of hydrocarbon constituent molecules. The method also includes, based on the certain crude oil characterization data, determining the relative ratio of each class of hydrocarbon constituent molecules that forms a chemical composition representative of the given crude oil, such that the chemical composition of the given crude oil is characterized, and displaying, as output to an end-user, the characterized chemical composition of the given crude oil.

The segment type can include, but is not limited to, methyl segment, zero-branch methylene segment, one-branch methylene segment, two-branch methylene segment, cyclohexane segment, cyclohexane side ring segment, cyclopentane segment, cyclopentane side ring segment, aromatic segment, and aromatic side ring segment, or any combination thereof. The step of determining segment type and segment number range is not by use of homologous series. A homologous series requires specification of a particular core structure, and has a variable aliphatic side chain length or a variable number of aliphatic side chains.

The method can include, for each class of hydrocarbon constituent molecules, estimating physical and chemical property values as a function of segment type and segment number range. A segment is a molecular structural repeating unit. Determining the segment type and the segment number range can include, for each class of hydrocarbon constituent molecules, identifying a probability distribution function for the segment type and the segment number range that defines the class of hydrocarbon constituent molecules, including identifying scale and shape parameters of the probability distribution function.

The method can further include, based on the identified probability distribution functions and the relative ratio of each class of hydrocarbon constituent molecules, estimating chemical composition of the given crude oil, and estimating physical and chemical properties of the given crude oil based on the estimated chemical composition.

The estimated physical properties of the given crude oil can include, but are not limited to, any one of boiling point, density, and viscosity, or any combination thereof. The estimated chemical properties of the given crude oil can include, but are not limited to, any one of paraffin content, naphthene content, aromatic content, carbon content, hydrogen content, C/H ratio, asphaltene content, carbon residue, sulfur content, nitrogen content, total acid number, or any combination thereof. Determining the relative ratio of each class of hydrocarbon constituent molecules can include matching the estimated physical and chemical properties of the given crude oil against the certain crude oil characterization data in order to determine the relative ratio of each class of hydrocarbon constituent molecules in the given crude oil. The classes of hydrocarbon constituent molecules can include, but are not limited to, paraffins (including both linear paraffins and iso-paraffins), naphthenes, and aromatic hydrocarbon constituent molecules. The physical property data on the hydrocarbon constituent molecules can include any one of vapor pressure, density, and viscosity, or any combination thereof. The chemical property data on the hydrocarbon constituent molecules can include any one of carbon content, hydrogen content, sulfur content, nitrogen content, oxygen content, or any combination thereof. The certain crude oil characterization data can include any one of boiling point, density, and viscosity, or any combination thereof. In limited other cases, the certain crude oil characterization data can also include any one of paraffin content, naphthene content, aromatic content, carbon content, hydrogen content, C/H ratio, asphaltene content, carbon residue, sulfur content, nitrogen content, total acid number, or any combination thereof. In these limited other cases, the certain crude oil characterization data can be available for a limited number of boiling point cuts. The method can further include using in a computer the characterized chemical composition of the given crude oil to predict physical and chemical properties of the given crude oil. The method can also further include in a computer, using the characterized chemical composition and/or predicted physical and chemical properties of the given crude oil to plan, schedule, simulate, design, optimize, and/or control petroleum refining operations.

In another embodiment, a method of blending crude oil includes, for each of two or more crude oil samples to form a blend, characterizing each of the crude oil samples by chemical composition and predicted physical and chemical properties, said characterizing resulting in respective characterizations of the two or more crude oil samples. The method further includes, based on said characterizations, determining respective ratios of the two or more crude oil samples, such that a resulting blend using the respective ratios of the sample crude oils has certain chemical composition and predicted physical and chemical properties, and forming the blend using amounts of the two or more sample crude oils in the determined respective ratios. The steps of characterizing each of the crude oil samples are as described above.

This invention has many advantages, including a scientific (i.e., molecular) basis for prediction and estimation of assays and properties (e.g., physical and chemical properties) of crude oil and petroleum fractions.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIGS. 3A-3B are illustrations of naphthene (N) hydrocarbon constituent molecules with at least either FIG. 3A: one cyclohexane ring, or FIG. 3B: one cyclopentane ring, up to 6 cyclohexane side rings, and up to 48 zero-branch methylene groups on up to 7 n-alkyl side chains.

Figure 4C:
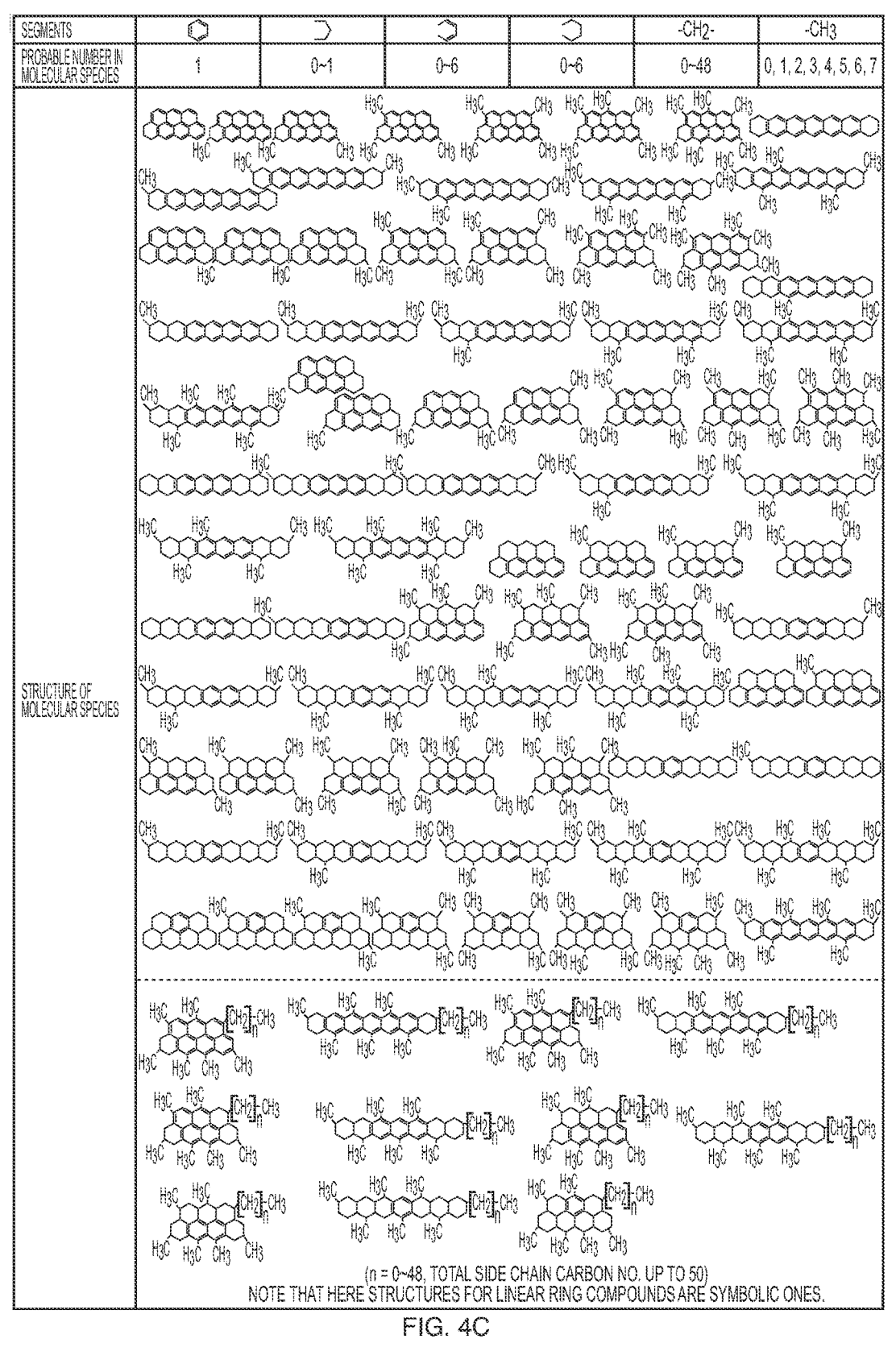

FIGS. 4A-4D are illustrations of aromatic (A) hydrocarbon constituent molecules with at least one aromatic ring, up to 1 cyclopentane side ring, up to 6 aromatic or cyclohexane side rings, and up to 48 zero-branch methylene groups on up to 7 n-alkyl side chains. Also included are asphaltene molecules represented as condensed aromatic molecules with 7 aromatic or cyclohexane rings and 6 n-alkyl side chains with up to 9 zero-branch methylene groups.

FIGS. 7A-7C are graphs of viscosities at 60° F. as a function of carbon number for the P (FIGS. 7A-1, 7A-2), N (FIGS. 7B-1, 7B-2), and A (FIGS. 7C-1, 7C-2) hydrocarbon constituent molecules. Also shown are viscosity curves as a function of carbon number for n-paraffins (FIG. 7A-2), dicyclohexane naphthenes (FIG. 7B-2), and dinuclear aromatics (FIG. 7C-2).

DETAILED DESCRIPTION OF THE INVENTION

Figure 3B:

A description of example embodiments of the invention follows.

Molecular Characterization of Petroleum Fractions

Molecule-based approaches have been extensively investigated as possible alternatives to the "pseudocomponent approach" to characterize crude oil and petroleum fractions in support of process modeling and simulation of refinery processes. See Watt; M. T. Klein, G. Hou, R. J. Bertolacini, L. J. Broadbelt, A. Kumar, Molecular Modeling in Heavy Hydrocarbon Conversions, Taylor & Francis, Boca Raton, Fla., 2006. An example of molecule-based models is Quann and Jaffe's Structured-Oriented Lumping. See R. J. Quann, S. B. Jaffe, Structured-Oriented Lumping: Describing the Chemistry of Complex Hydrocarbon Mixtures, Ind. Eng. Chem. Res. 1992, 31, 2483-2497; S. B. Jaffe, H. Freund, W. N. Olmstead, Extension of Structure-Oriented Lumping to Vacuum Residua, Ind. Eng. Chem. Res. 2005, 44, 9840-9852. Individual hydrocarbon molecules are represented by this model as vectors of incremental structural features that can describe the composition, reactions, and properties of petroleum mixtures. Chemical compositions of the individual hydrocarbon molecules are inferred from analytical measurement results. See Watt; J. M. Brown et al. Eckert and Vaněk, and Albahri proposed methods to simulate petroleum fractions and mixtures in terms of a preselected set of real components. See E. Eckert, T. Vaněk, New Approach to the Characterization of Petroleum Mixtures Used in the Modeling of Separation Processes, Computers & Chem. Eng. 2005, 30, 343-356 (hereinafter "Eckert and Vaněk"); T. A. Albahri, Molecularly Explicit Characterization Model (MECM) for Light Petroleum Fractions, Ind. Eng. Chem. Res. 2005, 44, 9286-9298 (hereinafter "Albahri"). The Molecularly Explicit Characterization Model (MECM) of Albahri uses routinely made measurements of a petroleum fraction's bulk properties such as the ASTM D86 distillation, API gravity, Reid vapor pressure, and the paraffin, naphthene, and aromatic content along with the pure components' properties to define chemical compositions of petroleum fuels suitable for simulation purposes. This approach offers important advantages over the traditional "pseudocomponents" approach in which the physical properties of "pseudocomponents" must be estimated by unreliable empirical methods. See Eckert and Vaněk. While Albahri demonstrated that the complex nature of petroleum fuels can be modeled by a limited set of representative pure components, the number and type of components chosen to represent a petroleum fraction, a key factor in determining the accuracy of the representation, is difficult to determine. See Y. Wu, N. Zhang, Molecular Characterization of Gasoline and Diesel Streams, Ind. Eng. Chem. Res. 2010, 49, 12773-12782. Same Aye and Zhang proposed to capture the molecular information of a petroleum refining stream in the form of Molecular Type Homologous Series (MTHS) matrix representation with structural lumping rules applied to transform the real components into a properly selected number of equivalent "lumped" species. See M. M. Same Aye, N. Zhang, A Novel Methodology in Transforming Bulk Properties of Refining Streams into Molecular Information, Chem. Eng. Sci. 2005, 60, 6702-6717 (hereinafter "Same Aye and Zhang").

Recently, in support of kinetic model development for petroleum conversion processes, Pyl et al., proposed composition modeling using constrained homologous series which permits the derivation of detailed composition of crude oil fractions from a limited set of mixture bulk properties. See S. P. Pyl, Z. Hou, K. M. Van Geem, M.-F. Reyniers, G. B. Marin, M. T. Klein, Modeling the Composition of Crude Oil Fractions Using Constrained Homologous Series, Ind. Eng. Chem. Res. 2011, 50, 10850-10858. A homologous series has a particular core structure, but has a variable aliphatic side chain length or a variable number of aliphatic side chains. The carbon number in each homologous series varies from a minimal carbon number $C_{min}$ to a maximum carbon number $C_{max}$, by varying the side chain length of the homologous series core structure.

In the present invention, a molecule-based approach characterizes crude oil and petroleum fractions for correlation, prediction, and estimation of assays and properties of crude oil, crude oil blends, petroleum fractions, and petroleum mixtures without using user-defined core structures, and without using structural lumping which requires large amounts of analytical data. The present invention approach employs a systematic methodology that determines numbers and types of molecules and their compositions to broadly represent physical and chemical properties of crude oil and petroleum fractions by constructing candidate compositions based on particular cross sections of segment type and segment number range and corresponding probability distribution functions.

It is well recognized that hydrocarbon molecules in crude oil are mainly composed of three classes of hydrocarbon molecules: paraffinic (P), naphthenic (N), and aromatic (A). The paraffins include saturated hydrocarbons with linear chains, i.e., n-paraffins or linear paraffins, and saturated hydrocarbons with branched chains, i.e., iso-paraffins. The naphthenes are saturated hydrocarbons with one or more naphthenic rings plus paraffinic side chains. The paraffins and the naphthenes together are called the saturates. The aromatics are hydrocarbons with aromatic rings, naphthenic rings, and paraffinic side chains. Additionally, sulfur, nitrogen, and oxygen may also be present as hetero-atoms with these hydrocarbon molecules and form various sub-classes such as thiophenes, carbozoles, phenols, naphthenic acids, etc. In the present invention, crude oil and petroleum fractions are similarly defined as mixtures of selected classes of hydrocarbon constituent molecules, i.e., paraffins (P), naphthenes (N), and aromatics (A). For each of the selected classes and sub-classes of hydrocarbon constituent molecules, their probability distribution functions are determined and optimized as described below. The use of probability distribution functions for classes and sub-classes of hydrocarbon constituent molecules in the present invention is less burdensome than traditional methods in terms of the amount of experimental data needed for computations of physical properties of crude oil, and enables easier adjustment of the profile (i.e., composition) of a given crude oil for, e.g., drift in properties due to a different depth from which the crude oil is produced, because the approach in the present invention uses the same profile and may adjust the probability distribution functions to match the change in physical and chemical properties accordingly.

Physical properties of selected classes of hydrocarbon constituent molecules for crude oil and petroleum fractions can be estimated with the segment-based PC-SAFT equation of state that enables rigor, accuracy, and thermodynamic consistency in the calculation of fundamental physical properties such as vapor pressure, boiling point, density, and heat capacity. See J. Gross, G. Sadowski, Perturbed-Chain SAFT: An Equation-of-State Based on a Perturbation Theory for Chain Molecules, Ind. Eng. Chem. Res. 2001, 40, 1244-1260 (hereinafter "Gross 2001"); J. Gross, O, Spuhl, F. Tumakaka, G. Sadowski, Modeling Copolymer Systems Using the Perturbed-Chain SAFT Equation of State, Ind. Eng. Chem. Res. 2003, 42, 1266-1274 (hereinafter "Gross 2003"). Exact makeup of a given crude oil in terms of various classes of hydrocarbon constituent molecules can be adjusted so that calculated physical and chemical properties can best match available physical and chemical property measurements of the crude oil, such as true boiling point, API gravity, viscosity, paraffin content, naphthene content, aromatic content, C/H ratio, etc. Missing properties of the crude oil assay are then estimated from the chemical compositions and the properties of these hydrocarbon constituent molecules. Utilities of this approach are further validated with the extensive crude oil assays available in the public domain. See Oil & Gas Databook.

To refine the molecular characterization for additional critical assay measurements, additional classes or subclasses of hydrocarbon constituent molecules can be optionally introduced on top of the three main classes of hydrocarbon constituent molecules, i.e., P, N, and A. For example, classes of sulfur molecules such as mercaptans, sulfides, and thiophenes, or nitrogen molecules such as carbazoles and quinolines, or oxygen molecules such as phenols and various types of carboxylic acids, can be incorporated to account for "sulfur content," "nitrogen content," or "total acid number," respectively. High molecular weight and highly branched aromatic hydrocarbon oligomers can also be incorporated to account for heavy asphaltenes to account for "asphaltene content". This molecule-based approach offers a much stronger scientific (i.e., molecular) basis, as compared to traditional empirical polynomial expressions, or analytical approaches that require expensive surrogate measurements, or statistical approaches that suffer from statistically weak or at times meaningless correlations, for interpolation and extrapolation of properties and assays of crude oil and petroleum fractions.

A Molecule-Based Approach to Characterizing Crude Oil and Petroleum Fractions

The central premise of the molecule-based approach described herein is that 1) proper selection of classes and sub-classes of model hydrocarbon constituent molecules and practical rules for automatically generating and constructing these model molecules from structural segments for crude oil, 2) recent advances in molecular thermodynamic models that facilitate accurate and thermodynamically consistent physical property calculations for hydrocarbon constituent molecules, and 3) robust algorithm for identification of chemical compositions for model hydrocarbon constituent molecules from regression of assay experimental data. Together they form a comprehensive and practical molecular characterization approach to correlate and estimate physical and chemical properties of crude oil and petroleum fractions. Successful implementation of such a molecular characterization approach offers a highly sought-after molecular insight into complex petroleum mixtures for optimal utilization and processing of such valuable natural resources. In addition, it generates a consistent set of model hydrocarbon constituent molecules and their chemical compositions for planning, scheduling, process simulation, design, optimization, and control of petroleum refining operations.

The key challenges with this molecule-based approach for crude oil properties and assays include: 1) identifying an optimal set of classes and sub-classes of model hydrocarbon constituent molecules, developing practical rules for automatic generation of these hydrocarbon constituent molecules from molecular structural repeating units (or structural "segments"), and determining probability distributions of the structural segments and the resulting chemical compositions required to calculate properties and assays for crude oil or petroleum fractions, 2) applying a thermodynamic framework to calculate physical properties of individual model hydrocarbon constituent molecules and their mixtures accurately and with thermodynamic consistency, and 3) developing a robust regression methodology to facilitate determination of chemical compositions of crude oil or petroleum fractions in terms of model hydrocarbon constituent molecules.

As the carbon number increases, the numbers of possible hydrocarbon constituent molecules in crude oil increase exponentially and they quickly become totally unmanageable. See Saine Aye and Zhang. To minimize the number of model hydrocarbon constituent molecules required to fully characterize physical and chemical properties for crude oil and petroleum fractions, the instant application starts with the knowledge that crude oil in general is mainly composed of three different classes of hydrocarbon molecules: paraffins (P), naphthenes (N), and aromatics (A). In other words, crude oil and petroleum mixtures can be defined alike in terms of combinations of three classes of hydrocarbon constituent molecules, i.e., P, N, and A. For each of the three classes of hydrocarbon constituent molecules, proper segment types, segment number ranges, and their respective probability distribution functions must be determined and optimized with the aim to provide a comprehensive and practical representation of diverse physical and chemical properties of crude oil such as boiling point, density, viscosity, paraffin content, naphthene content, aromatic content, carbon content, hydrogen content, C/H ratio, carbon residue, etc.

Figures 1, 5A:
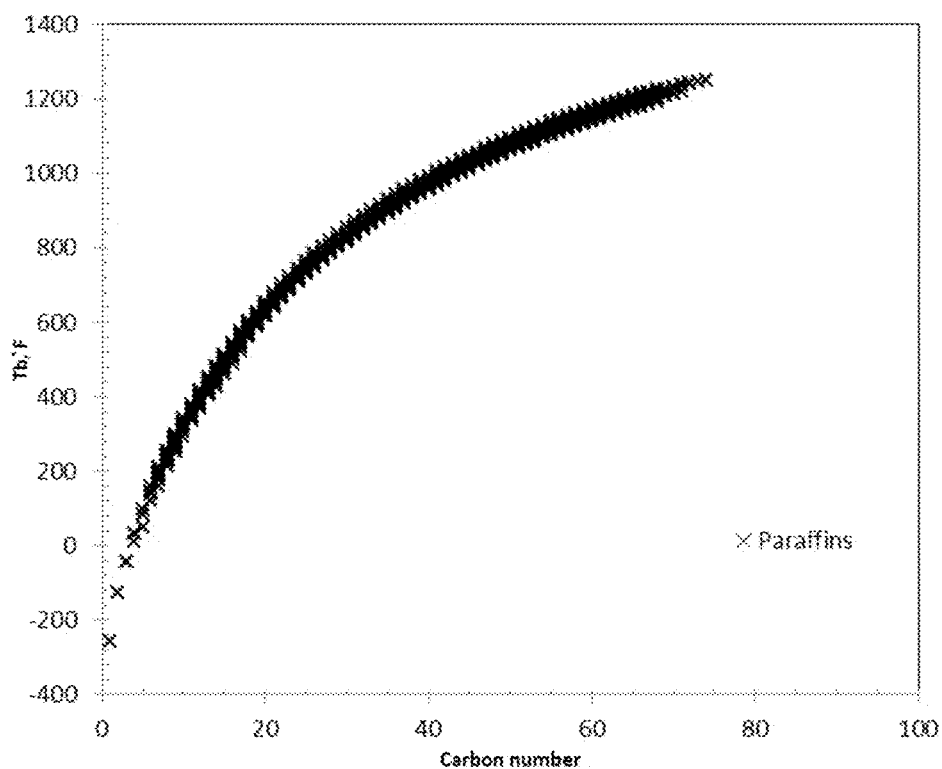
FIG. 1 is an illustration of segments or molecular repeat units that make up the paraffins (P), naphthenes (N), aromatics (A), and other hydrocarbon constituent molecules.
FIGS. 5A-5C are graphs of boiling point as a function of carbon number for the P (FIGS. 5A-1, 5A-2), N (FIGS. 5B-1, 5B-2), and A (FIGS. 5C-1, 5C-2) hydrocarbon constituent molecules. Also shown are boiling point curves as a function of carbon number for n-paraffins (FIG. 5A-2), dicyclohexane naphthenes (FIG. 5B-2), and dinuclear aromatics (FIG. 5C-2).

As an illustration, FIG. 1 shows among others the molecular structural repeating units or "segments" that are selected to make up the model hydrocarbon constituent molecules in P, N, and A. Here, the —CH$_3$ segment is the methyl end group, the —CH$_2$— segment is the zero-branch methylene repeat group, the

segment is the one-branch methylene group, the

segment is the two-branch methylene group, the

segment is the cyclohexane ring group, the

segment is the cyclohexane side ring group for polycyclic naphthenic molecules, the

segment is the cyclopentane ring group, the

segment is the cyclopentane side ring group, the

segment is the aromatic ring group, and the

segment is the aromatic side ring group. Note that the

segment, the

segment, and the

Figures 2, 5A:
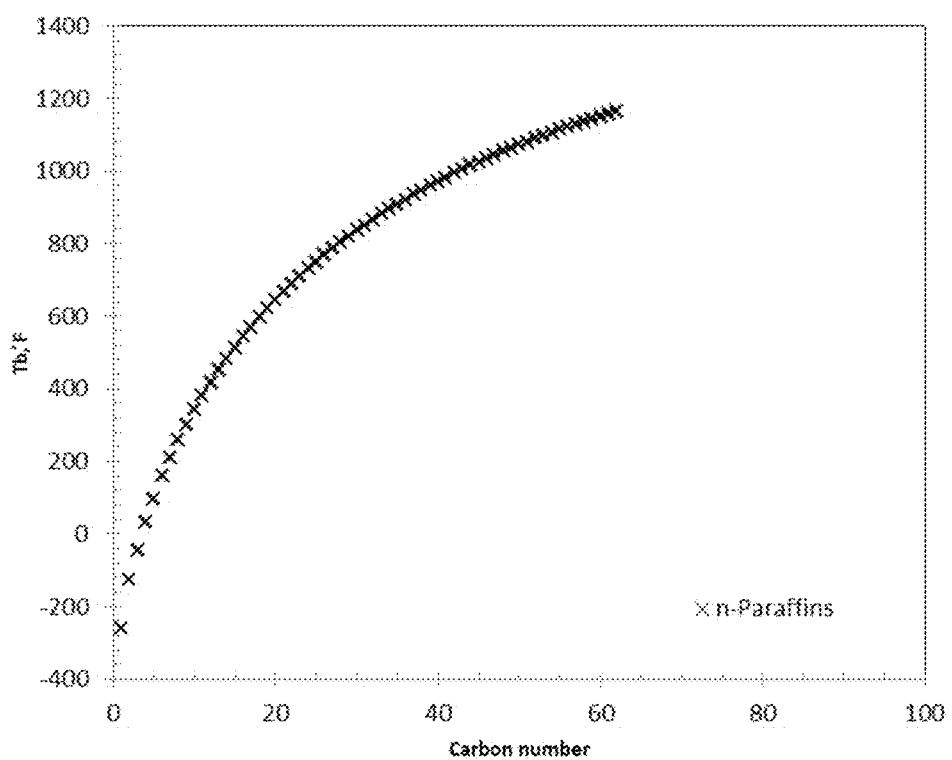
FIG. 2 is an illustration of paraffins (P) hydrocarbon constituent molecules with carbon numbers from 2 to 74, with up to 60 zero-branch methylene groups, up to 3 one-branch methylene groups, and up to 2 two-branch methylene groups.
Figures 1, 5B:
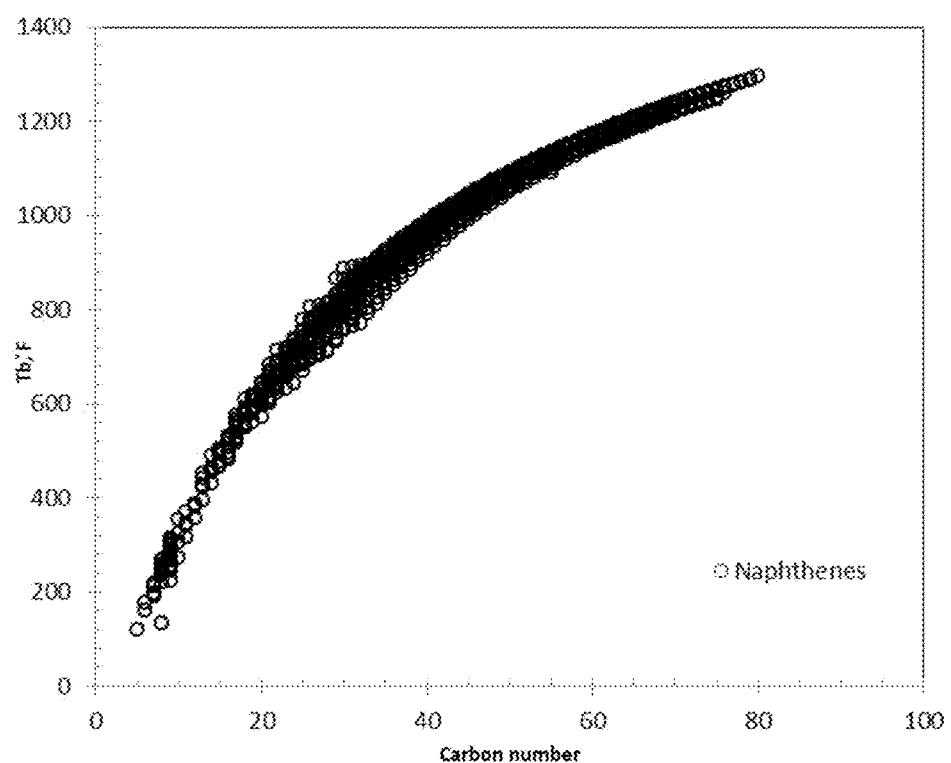
Figures 2, 5B:
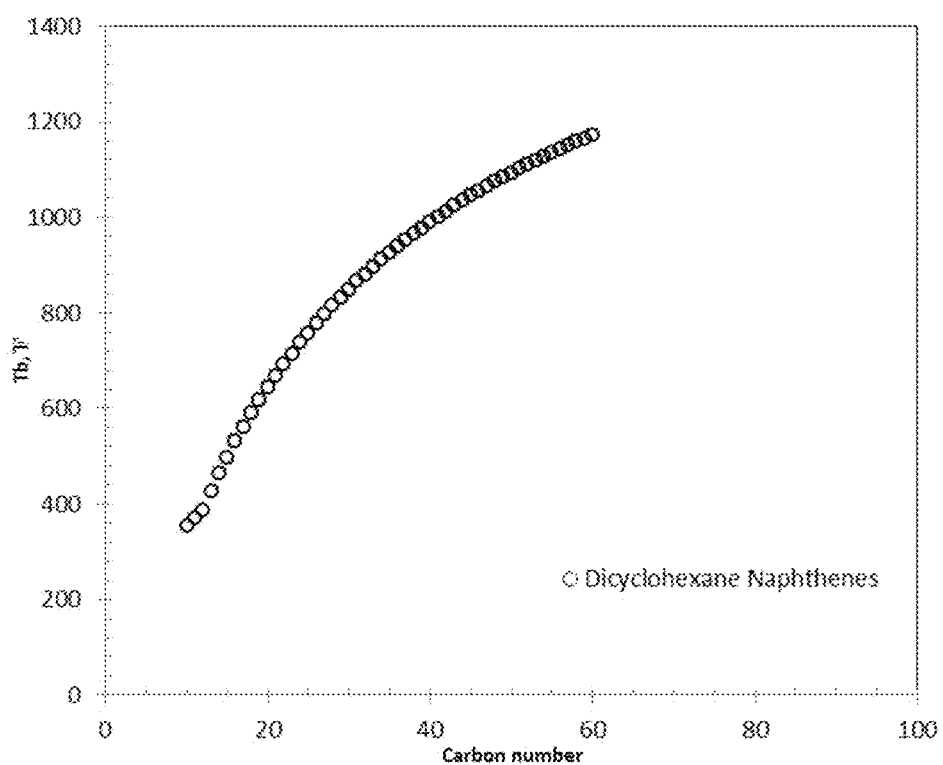
Figures 1, 5C:
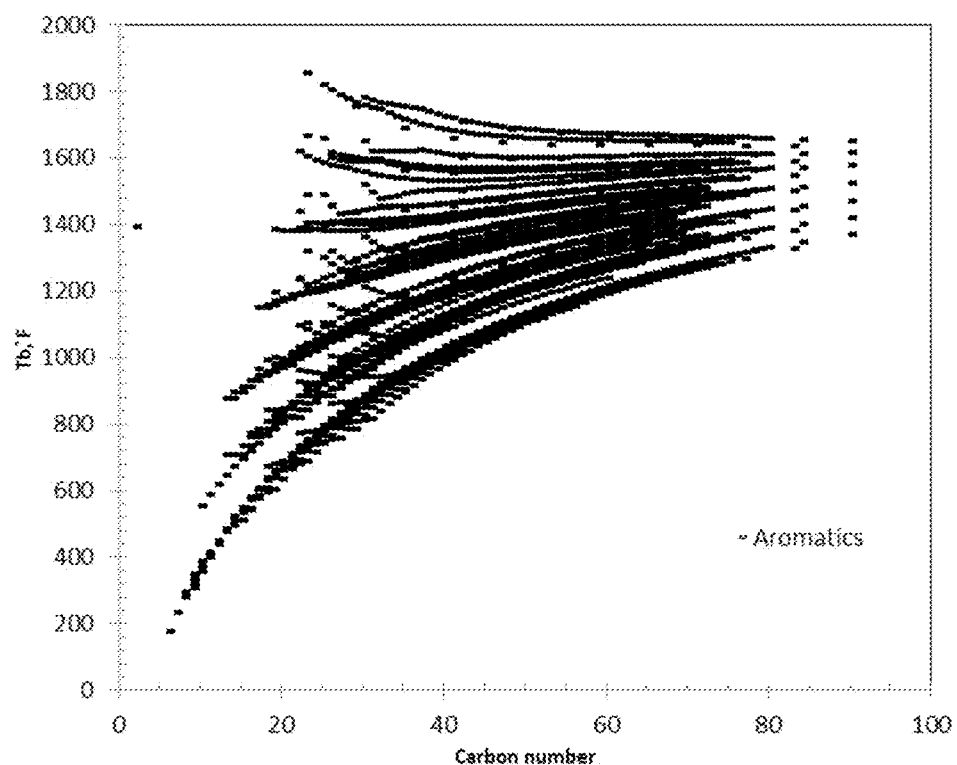
Figures 2, 5C:
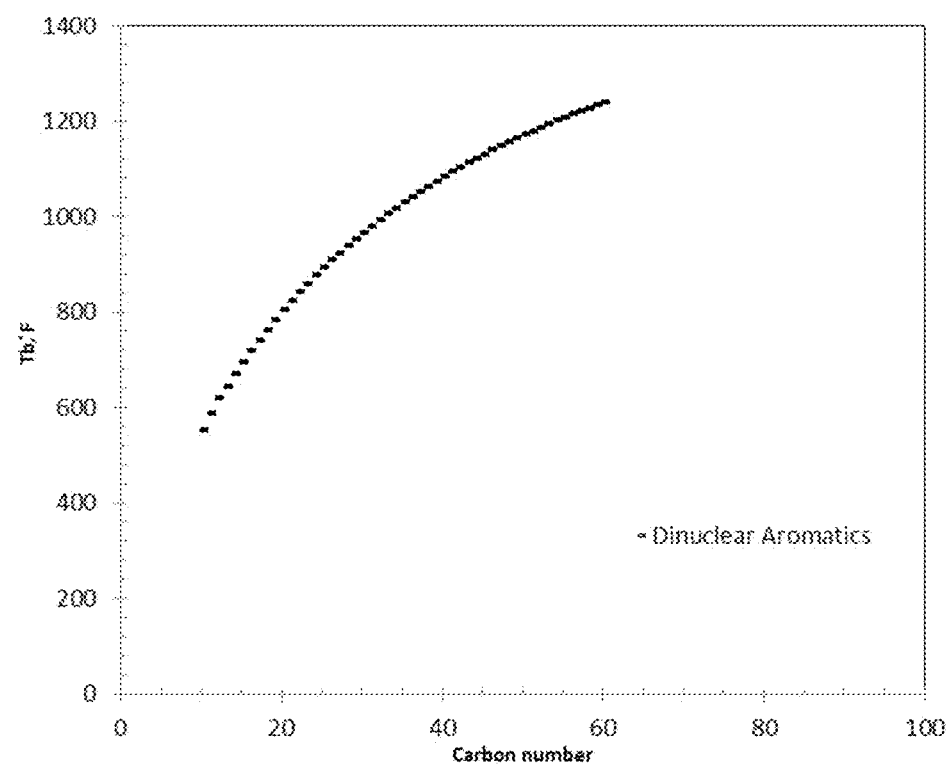
Figures 1, 6A:
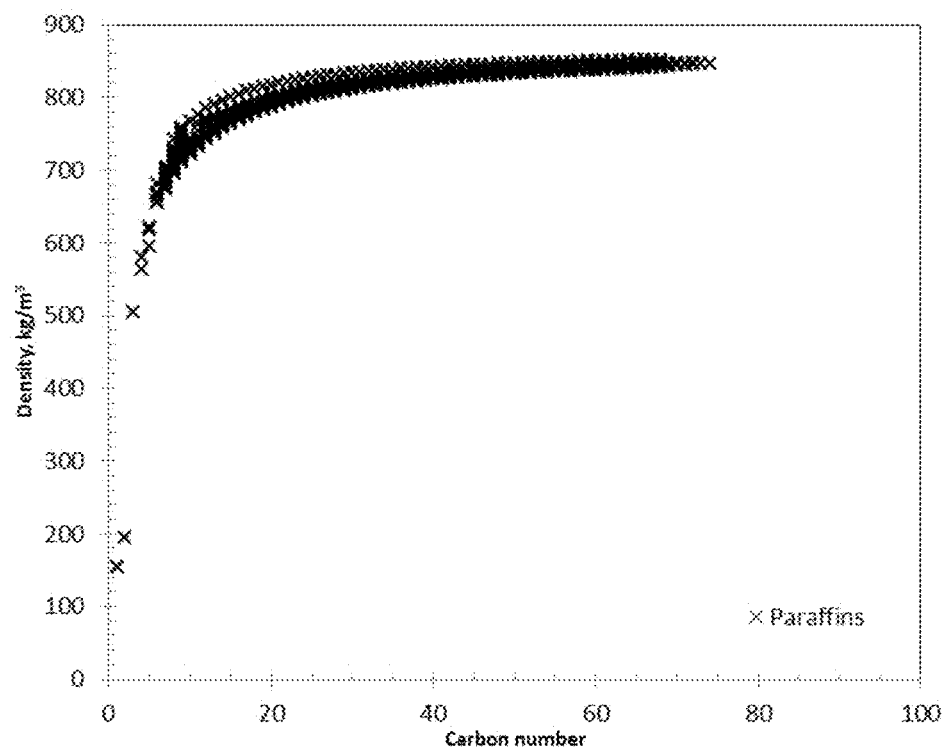
FIGS. 6A-6C are graphs of density as a function of carbon number for the P (FIGS. 6A-1, 6A-2), N (FIGS. 6B-1, 6B-2), and A (FIGS. 6C-1, 6C-2) hydrocarbon constituent molecules. Also shown are density curves as a function of carbon number for n-paraffins (FIG. 6A-2), dicyclohexane naphthenes (FIG. 6B-2), and dinuclear aromatics (FIG. 6C-2).
Figures 2, 6A:
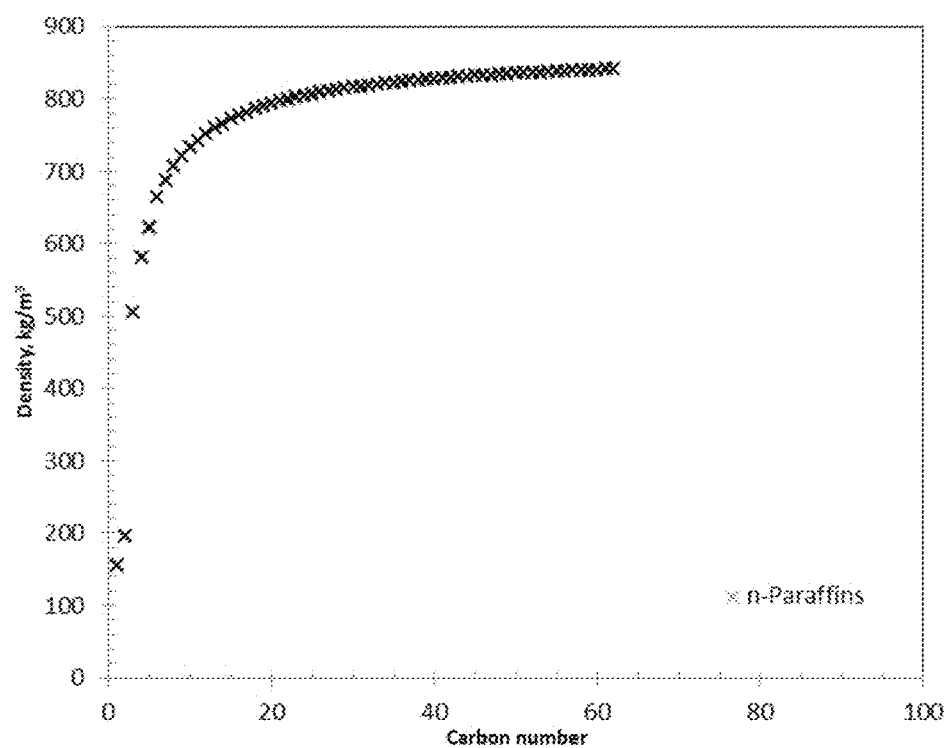
Figures 1, 6B:
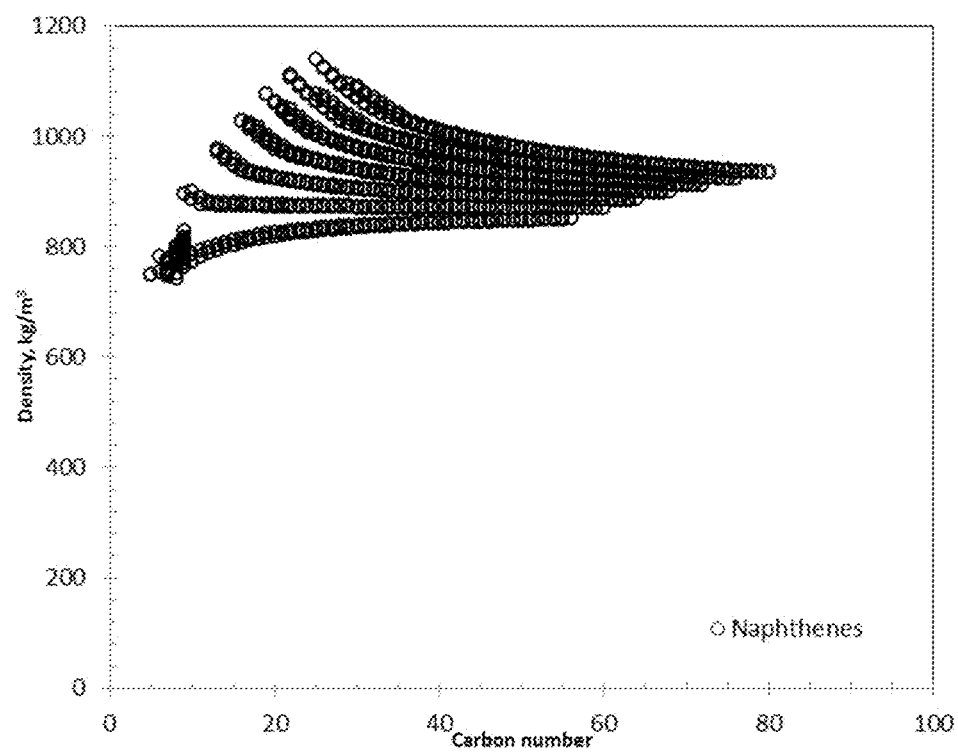
Figures 2, 6B:
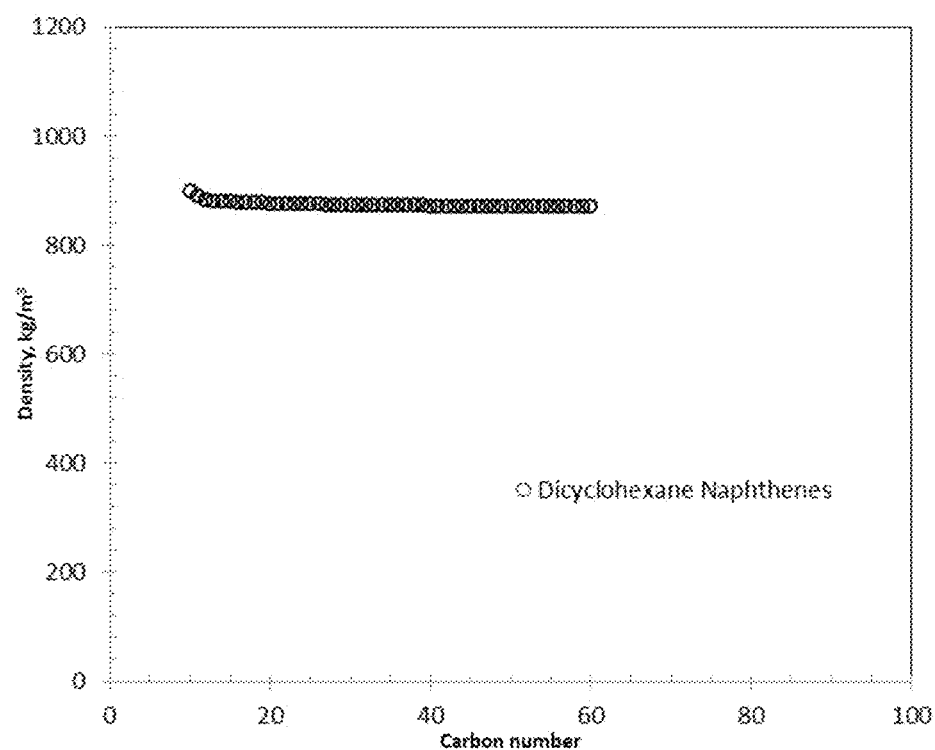
Figures 1, 6C:
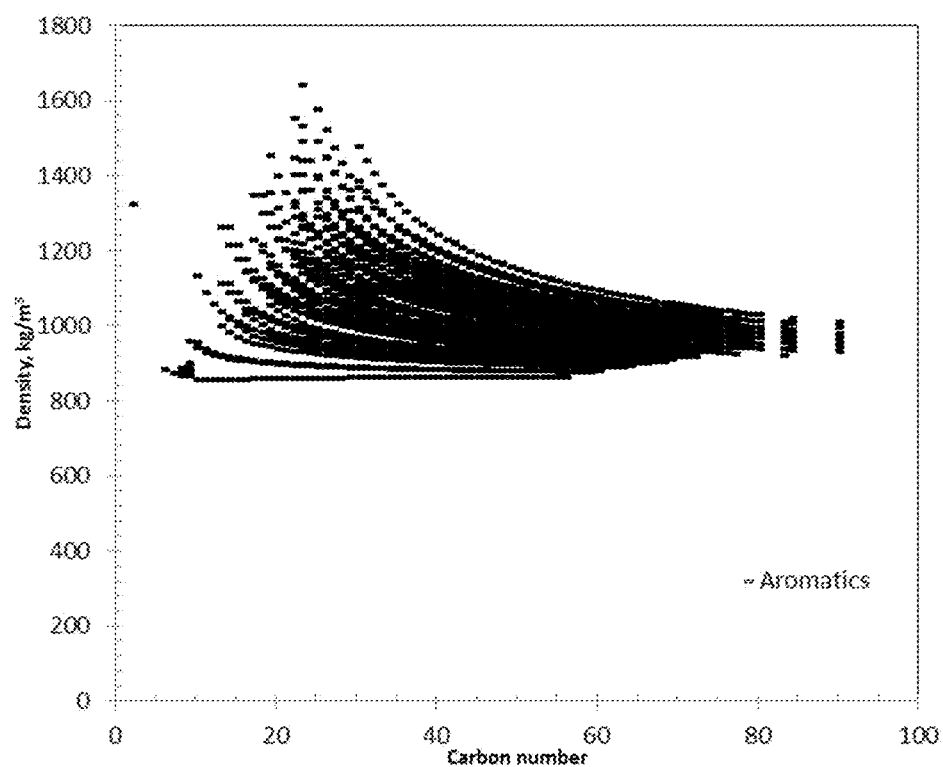
Figures 2, 6C:
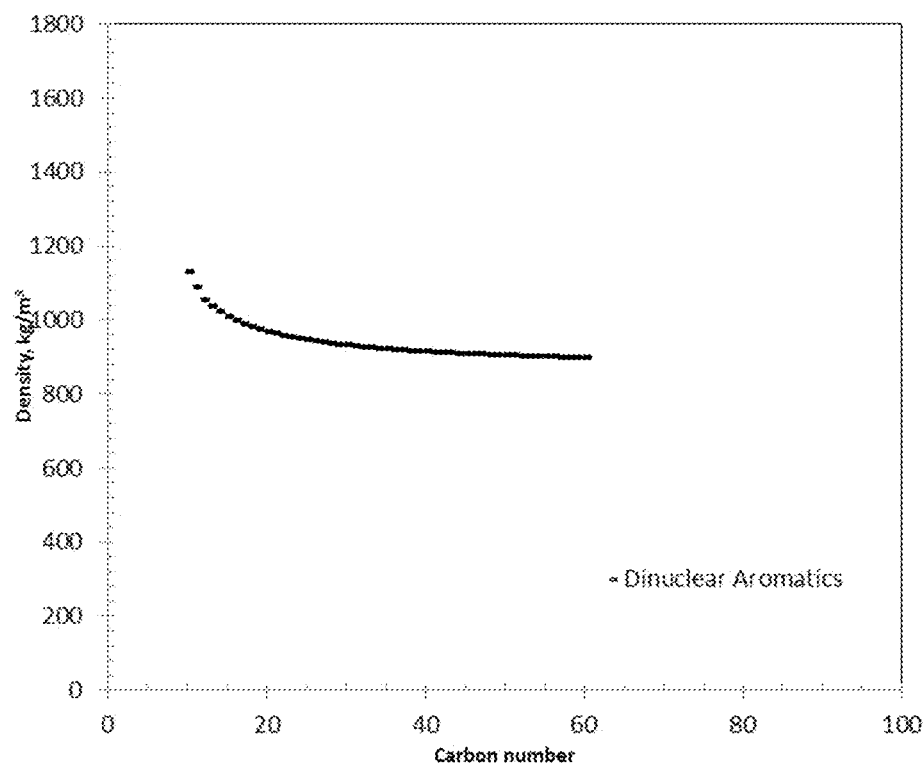
Figures 1, 7B:
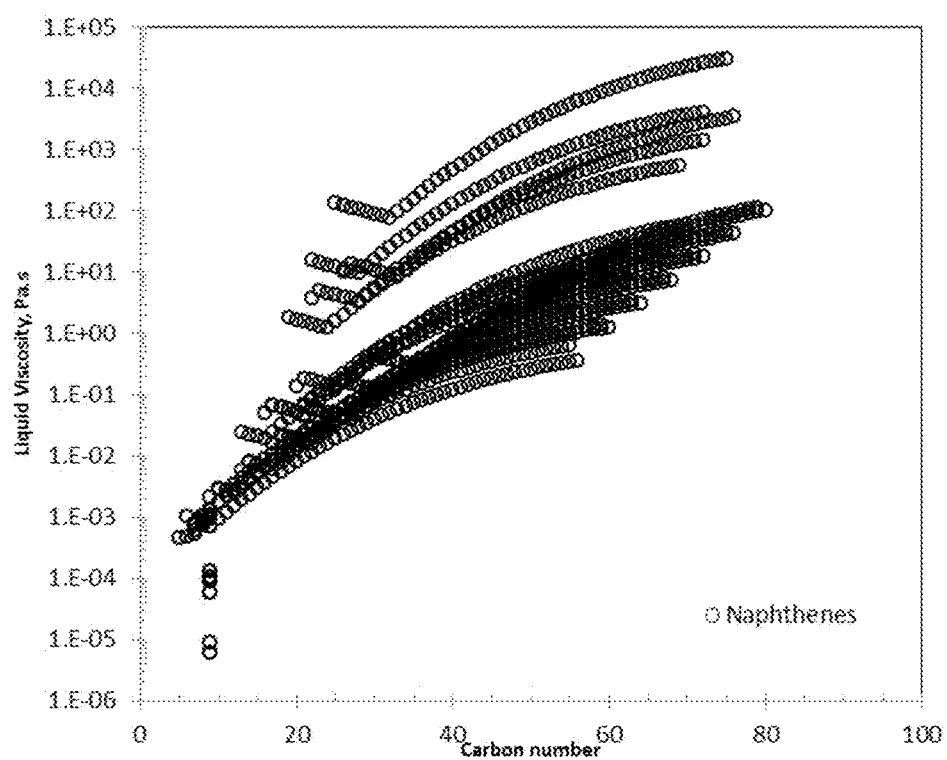
Figures 2, 7B:
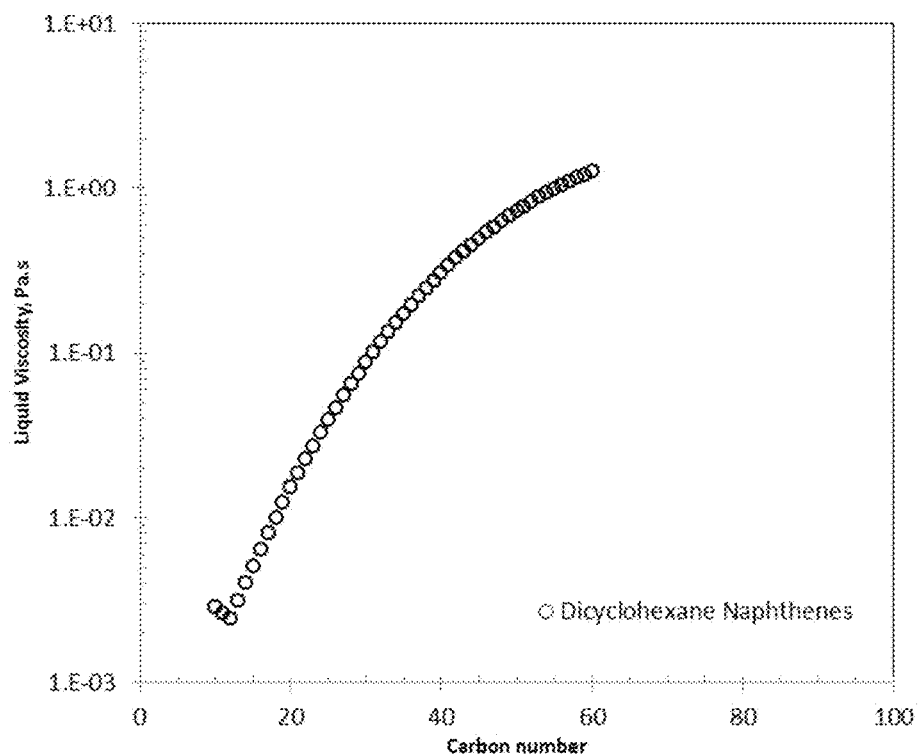
Figures 1, 7C:
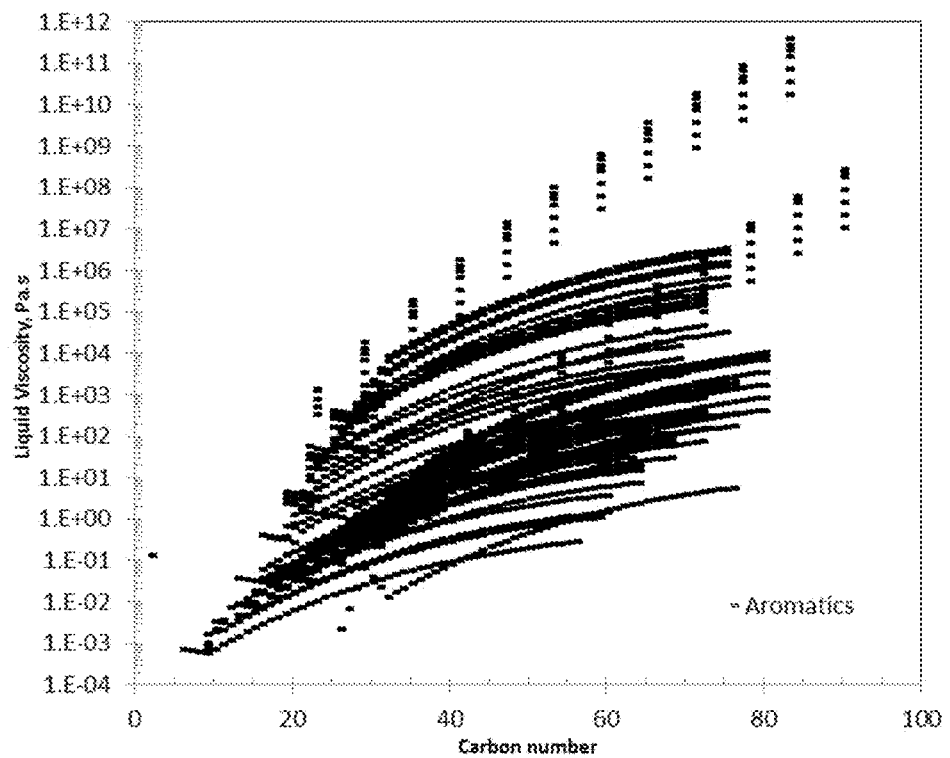
Figures 2, 7C:
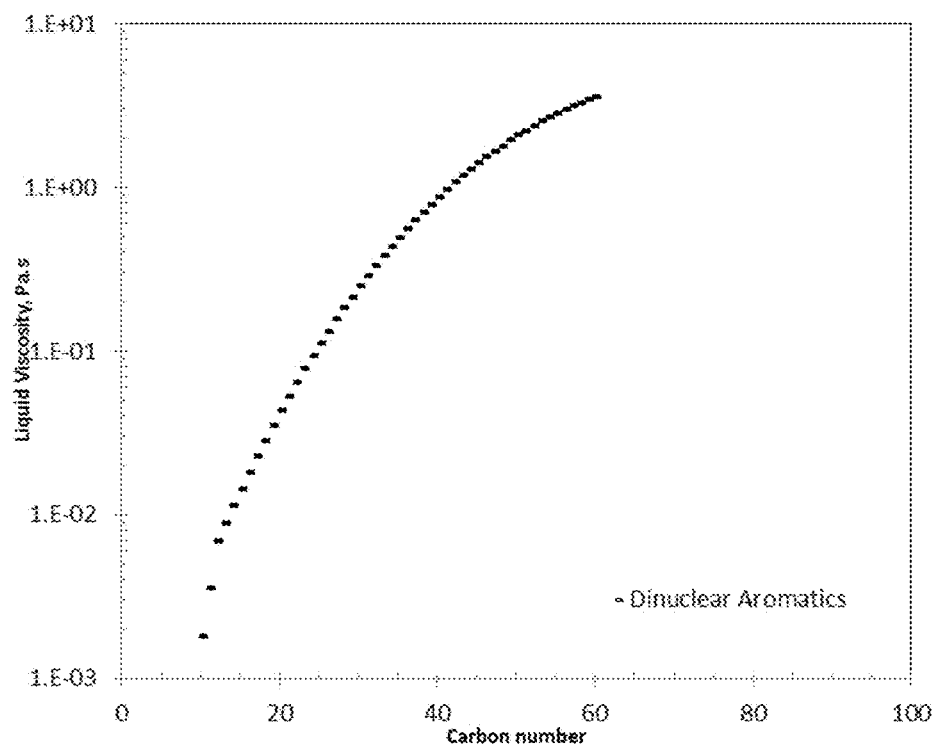

segment are used to construct polycyclic naphthenic and aromatic molecules. These ring molecules can include both linear ring and condensed ring molecules. The chemical formulas for the various side ring segments are adjusted to satisfy the atom number balance depending on whether and how the linear rings or the condensed rings are formed. FIG. 2 shows paraffinic molecules that make up the paraffin (P) class of hydrocarbon constituent molecules with up to sixty zero-branch methylene group, up to three one-branch methylene group, and up to two two-branch methylene groups, for a total of up to seventy-four carbons. FIG. 3 shows naphthenic molecules that make up the naphthenic (N) class of hydrocarbon constituent molecules. These naphthenic molecules may have at least either one cyclohexane ring or one cyclopentane ring, and up to six linear or condensed cyclohexane side rings. FIG. 4 shows aromatic molecules that make up the aromatic (A) class of hydrocarbon constituent molecules. These aromatic molecules may have at least one aromatic ring, up to one cyclopentane side ring, and up to six linear or condensed cyclohexane or aromatic side rings. In addition, these ring molecules can have one or multiple n-alkyl side chains. Both linear rings and condensed rings are considered for these naphthenic and aromatic molecules. A condensed ring arrangement of three or more aromatic or cyclohexane rings, as shown in FIGS. 3 and 4, includes at least one carbon atom that is part of three rings. A linear ring arrangement of three or more aromatic or cyclohexane rings, by contrast, includes no carbon atoms that are part of more than two rings, that is, the rings are arranged linearly in a row, side by side. Table 1 summarizes the numbers of components considered for these hydrocarbon constituent molecules.

TABLE 1

Numbers of molecules considered for various classes of hydrocarbon constituent molecules.

| Molecules | Number | Carbon number range |
| --- | --- | --- |
| n-Paraffins | 61 | C2-C62 |
| iso-Paraffins | 723 | C4-C74 |
| Naphthenes | 1230 | C5-C80 |
| Aromatics | 2918 | C6-C90 |
| Total | 4932 | C2-C90 |

To show the broad ranges of physical properties represented by these hydrocarbon constituent molecules, the corresponding boiling points, densities, and viscosities of these components are shown in FIGS. 5-7, respectively. The boiling points and densities are estimated with the segment-based PC-SAFT equation-of-state (EOS), while the viscosities are estimated by employing group contribution methodology. See Gross 2001; Gross 2003; B. E. Poling, J. M. Prausnitz, J. P. O'Connell, The Properties of Gases and Liquids, 5th Ed., McGraw-Hill, New York, 2001, pp. 9.77-9.90.

Sulfur molecules such as mercaptans, sulfides, and thiophenes can be present in crude oil in significant amounts. Nitrogen molecules such as carbozoles and quinolones, oxygen molecules such as phenols and naphthenic acids, and asphaltene molecules can also be present in certain crude oil. Additional classes or subclasses of hydrocarbon constituent molecules and corresponding structural segments may be added in addition to the P, N, and A molecules and their structural segments in order to provide sufficient fidelity for crude oil properties and assays.

In one illustrative embodiment, each molecule is considered, as discussed above, as one of three classes of hydrocarbon constituent molecules, i.e., paraffins (P), naphthenes (IV), and aromatics (A). Molecular structural repeating units or structural "segments" are selected to make up the molecules in these three classes of molecules. For example, n-paraffin P molecules are considered as molecules made up of four types of segments: $-CH_3$, $-CH_2-$, $-CH-$, and $-C-$, wherein the number of $-CH_3$ segments is always two, the number of $-CH-$ segments is always zero, and the number of $-C-$segments is always zero in order to construct realistic n-paraffin P molecules from these four types of segments. Therefore, for a n-paraffin P molecule with $l$ $-CH_2-$ segments, m $-CH-$ segments (m=0), and n $-C-$ segments (n=0), the component mole fractions $y_l^P$ are defined as the product of four quantities: (1) the class P molecule mole fraction $y_p^{class}$, (2) the $-CH_2-$ segment number probability $p_p^{-CH2-}$ ($l$) for class P molecules, (3) the $-CH-$ segment number probability $p_p^{-CH-}$ (m=0) for class P molecules, and (4) the $-C-$ segment number probability $p_p^{-C-}$ (n=0) for class P molecules.

$$y_{l,m=0,n=0}^P = y_p^{class} \cdot p_p^{-CH2-}(l) \cdot p_p^{-CH-}(m=0) \cdot p_p^{-C-}(n=0) \quad (1)$$

As another example, iso-paraffin P molecules are molecules made of four types of segments: $-CH_3$, $-CH_2-$, $-CH-$, and $-C-$. Certain constraints are imposed to construct realistic molecules from these four types of segments. Specifically, the number of $-CH_3$ segments is not an independent variable, because it is dependent on the numbers of the other three types of segments. For an iso-paraffin P molecule with $l$ $-CH_2-$ segments, m $-CH-$ segments, and n $-C-$ segments, the component mole fraction $y_{l,m,n}^P$ is defined as the product of four quantities: (1) the class P molecule mole fraction $y_p^{class}$, (2) the $-CH_2-$ segment number probability $p_p^{-CH2-}$ ($l$) for class P molecules, (3) the $-CH-$ segment number probability $p_p^{-CH-}$ (m) for class P molecules, and (4) the $-C-$ segment number probability $p_p^{-C-}$ (n) for class P molecules.

$$y_{l,m,n}^P = y_p^{class} \cdot p_p^{-CH2-}(l) \cdot p_p^{-CH-}(m) \cdot p_p^{-C-}(n) \quad (2)$$

With the segment approach, all the components that are associated with the segments for the classes of molecules can be generated a priori and their concentrations are normalized from distributions computed with the assumed distribution functions for appropriate segments.

The regression calculations minimize the residual root-mean-square error (RRMSE) defined as:

$$RRMSE = \sqrt{\frac{\sum_{i=1}^{k} \sum_{j=1}^{m} \left(\frac{Z_{ij} - ZM_{ij}}{\sigma_{ij}}\right)^2}{k - n}} \quad (3)$$

where ZM=measured (experimental) value, Z=calculated value, σ=standard deviation, i=data point number, k=total number of data points, j=measured variable for a data point (such as temperature, density, viscosity, or vol %), m=number of measured variables for a data point, n=total number of adjustable parameters.

Figure 8:
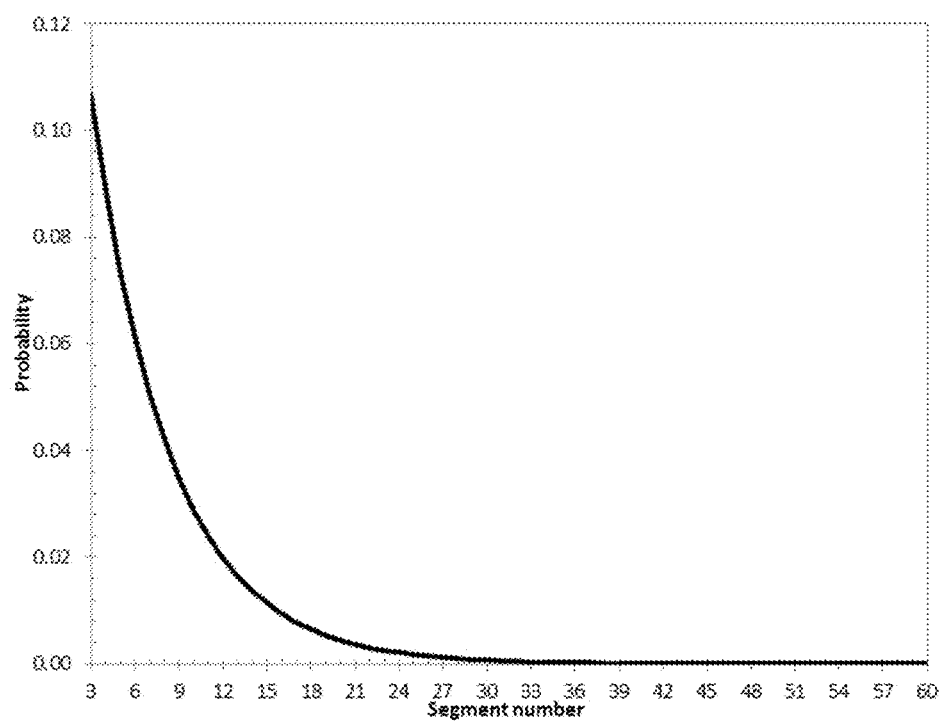
FIG. 8 is a graph of a gamma probability distribution function as a function of segment number for n-paraffinic molecules with a scale parameter of 11 and a shape parameter of 1.

To identify compositions of the selected molecules, probability distribution functions and associated parameters for the structural segments for each class of molecules, i.e., P, N, and A, are established through systematic investigation. A variety of probability distribution functions can be considered. For example, a gamma distribution function is a two parameter family of probability distributions of the form $$p(n) = \frac{(n-L)^{\alpha-1} \cdot e^{-\frac{n-L}{\beta}}}{\beta^\alpha \cdot \Gamma(\alpha)} \quad (4)$$

where p(n) is the probability of the sample value n; L is the location, the starting point of the probability distribution function; α is the shape factor; β is the scale parameter; and Γ(α) is the gamma function. FIG. 8 shows the gamma probability distribution function chosen for the $-CH_2-$ segment of P with scale parameter of 11 and shape parameter of 1. The relative contents of the three classes of hydrocarbon constituent molecules are then identified from regression against assay physical and chemical data such as true boiling point, API gravity, viscosity, paraffin content, naphthene content, and aromatic content of selected distilled fractions as described below.

The segment-based PC-SAFT equation-of-state (EOS) is used to develop a thermodynamically consistent framework to accurately calculate physical properties for the model hydrocarbon constituent molecules and their mixtures. See Gross 2001; Gross 2003. Segment-based parameters required to characterize the segments that build up the P, N, and A molecules used to represent crude oil are thereby obtained with PC-SAFT. These segment-based PC-SAFT parameters include segment ratio, segment size, and segment energy parameters. See Gross 2003. These parameters are identified from regression of experimental data on vapor pressure, liquid density and liquid heat capacity of hundreds of hydrocarbon compounds made up of these segments. Table 2 summarizes the PC-SAFT segments and corresponding segment parameter values.

These segment parameters together with the PC-SAFT EOS provide a rigorous and predictive thermodynamic framework based on principles of statistical mechanics This thermodynamic framework enables systematic exploration of different classes of molecules with various types of segments and segment number ranges. Of particular significance is the unique ability of the PC-SAFT EOS to accurately correlate and predict vapor pressure and liquid density simultaneously. In contrast, typical cubic equations of state such as Peng-Robinson and Redlich-Kwong-Soave are only capable of calculating vapor pressure accurately. These cubic equations of state are incapable of calculating liquid density accurately.

TABLE 2

PC-SAFT segments and segment parameter values

| Segment Name | Structure | PCSFTR[a], mol/g | PCSFTU[b], K | PCSFTV[c], Å |
|---|---|---|---|---|
| CH3 | —CH$_3$ | 5.12E−02 | 213.467 | 3.574 |
| CH2CH2 | —CH$_2$—CH$_2$— | 2.85E−02 | 253.397 | 3.912 |
| CH | (structure) | 2.29E−03 | 371.065 | 7.773 |
| C | (structure) | −1.25E−01 | 68.802 | 1.408 |

TABLE 2-continued

PC-SAFT segments and segment parameter values

| Segment Name | Structure | PCSFTR[a], mol/g | PCSFTU[b], K | PCSFTV[c], Å |
|---|---|---|---|---|
| CHCH | (structure) | 1.83E−03 | 567.588 | 7.749 |
| CC | (structure) | −1.02E−01 | 55.808 | 1.785 |
| CHC | (structure) | 2.52E−05 | 750.208 | 24.432 |
| N6 | (hexane ring) | 2.67E−02 | 304.985 | 4.018 |
| N5 | (pentane ring) | 2.93E−02 | 302.102 | 3.927 |
| A6 | (benzene ring) | 3.28E−02 | 281.715 | 3.583 |
| AC | (structure) | 6.59E−04 | 1510.012 | 11.352 |
| ACO | (structure) | 1.18E−03 | 1676.895 | 8.649 |
| PACC | (structure) | 3.93E−03 | 6136.912 | 4.249 |

Notes:
[a]PCSFTR is the segment ratio parameter in the polymer PC-SAFT equation of state
[b]PCSFTU is the segment energy parameter in the polymer PC-SAFT equation of state
[c]PCSFTV is the segment diameter parameter in the polymer PC-SAFT equation of state The group contribution parameters for the viscosity model are summarized in Table 3.

TABLE 3

Group contribution parameters for the viscosity model

| Group | Structure | $a_j$ | $b_j$ | $c_j$ | Note |
|---|---|---|---|---|---|
| CH3 | —CH$_3$ | −5.481 | 213.6 | 0 | |
| CH2CH2 | —CH$_2$—CH$_2$— | −0.138 | 272.8 | 0 | Used for paraffins |
| CH2CH2 | —CH$_2$—CH$_2$— | −9.955 | 747.5 | 1.391 | Used for naphthenes and aromatics |
| CH | (structure) | 5.175 | 8.3 | 0 | |

TABLE 3-continued

Group contribution parameters for the viscosity model

| Group | Structure | $a_j$ | $b_j$ | $c_j$ | Note |
|---|---|---|---|---|---|
| C | 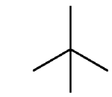 | 9.982 | 102.6 | 0 | |
| CHCH | 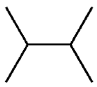 | 9.585 | 263.383 | 0 | |
| CHC | 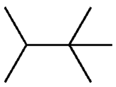 | 14.111 | 530.432 | 0 | |
| CC | 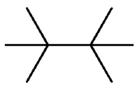 | 21.648 | −168.8 | 0 | |
| N5 | 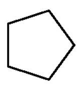 | −1.712 | 558.0 | −1.394 | |
| N6 | 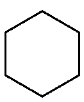 | 3.023 | 751.9 | −2.206 | |
| CH—NP1 | 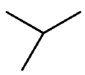 | −13.368 | 524.5 | 2.614 | CH shared by C5/C6 ring and one linear alkyl group |
| CH—NP2 | 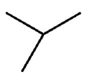 | 3.771 | −87.1 | 0 | CH shared by C5/C6 ring and multi linear alkyl groups |
| C—N | 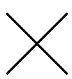 | 8.217 | −702.8 | 0 | C shared by two alkyl rings |
| CH—N | 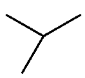 | 3.701 | −215.1 | 0 | CH shared by two alkyl rings |
| CHCH—N5 | 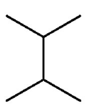 | 2.905 | 35.4 | 0 | CHCH shared by one C5 ring and one C6 ring |
| CHCH—N6 | 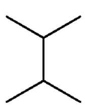 | 4.122 | −238.3 | 0 | CHCH shared by two C6 rings |
| CH-MNP1 | 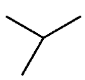 | −33.605 | 1733.4 | 5.493 | CH shared by multiple C6 rings and one linear alkyl group |
| A6 | 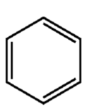 | 8.320 | 280.6 | −2.925 | |
| C-AP | 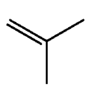 | 1.996 | 0.0 | 0.256 | shared by benzene ring and linear alkyl group |
| C-AOP | 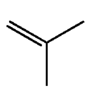 | 1.578 | 64.1 | 0.325 | C shared by benzene ring and ortho-position linear alkyl group |

TABLE 3-continued

Group contribution parameters for the viscosity model

| Group | Structure | $a_j$ | $b_j$ | $c_j$ | Note |
|---|---|---|---|---|---|
| C-AN5 | 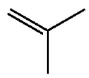 | 1.109 | 0.0 | 0.070 | C shared by benzene ring and C5 ring |
| C-AN6 | 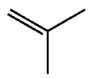 | 2.988 | 0.0 | −0.202 | C shared by benzene ring and C6 ring |
| CC-A | 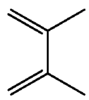 | −2.886 | 0.0 | 1.106 | C=C shared by two benzene rings |
| C-A2N | 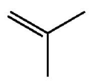 | 3.404 | 0.0 | −0.526 | C shard by two benzene rings and one C6 ring |
| C-MAP | 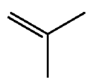 | 1.161 | 875.8 | 0 | C shared by multiple benzene rings and one linear alkyl group |

Notes:

$$\ln(\eta(Pa \cdot s)) = \sum_i w_i \ln \eta_i + w_{P1} \cdot w_{NA} \cdot C \quad (5)$$

$$\ln(\eta_i(Pa \cdot s)) = \sum_j N_{ij}^e \left( a_j + \frac{b}{T(K)} + c_j \ln(T(K)) \right) \quad (6)$$

where η is the viscosity of the mixture; $w_i$ is the mass fraction of component i; $\eta_i$ is the viscosity of the pure component i; $w_{P1}$ is the summation of the mass fraction of all the normal paraffin components and all the iso-paraffin components; $w_{NA}$ is the summation of all the naphthenic components and all the aromatics components; C is the interaction parameter between paraffin components and naphthenic components or aromatic components; $a_j$, $b_j$ and $c_j$ are model parameters for group j used to calculate group contribution to component viscosity; and T is the temperature; $N_{ij}^e$ is the effective group number of group j in the component i. For all groups except the group $CH_2CH_2$, the actual group number is the effective group number. The effective group number for $CH_2CH_2$ is estimated as follows, $$N_{ij}^e = N_{ij} \times \exp\left( \frac{-N_{ij}}{C_1 + C_2 N_{ij}} \right) \quad (7)$$

where $N_{ij}$ is the actual group number of $CH_2CH_2$, and $C_1$ and $C_2$ are the parameters determined for a particular class. For paraffins, $C_1$ and $C_2$ are identified to be 16.382 and 0.247, respectively. For naphathenes and aromatics, $C_1$ and $C_2$ are identified to be 35.341 and 0, respectively.

Identifying Molecular Distribution Parameters

Figure 9:
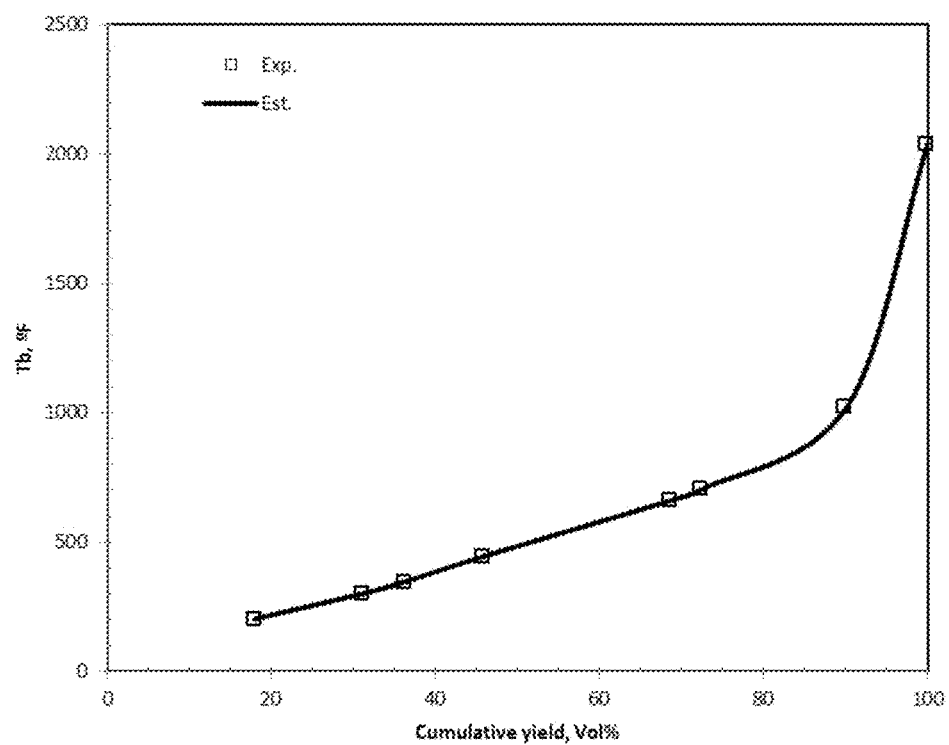
FIG. 9 is a graph of true boiling point experimental assay data and model results as a function of volume distilled (vol %) for UK Brent crude (the Forties blend).
Figure 10:
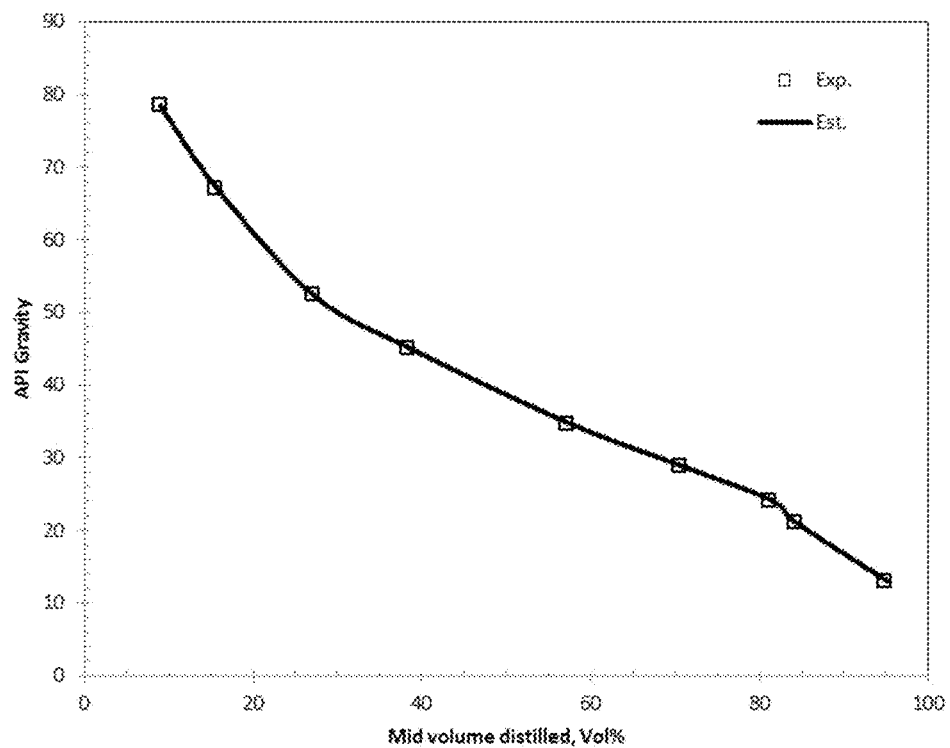
FIG. 10 is a graph of API gravity experimental assay data and model results as a function of volume distilled (vol %) for UK Brent crude (the Forties blend).
Figure 11:
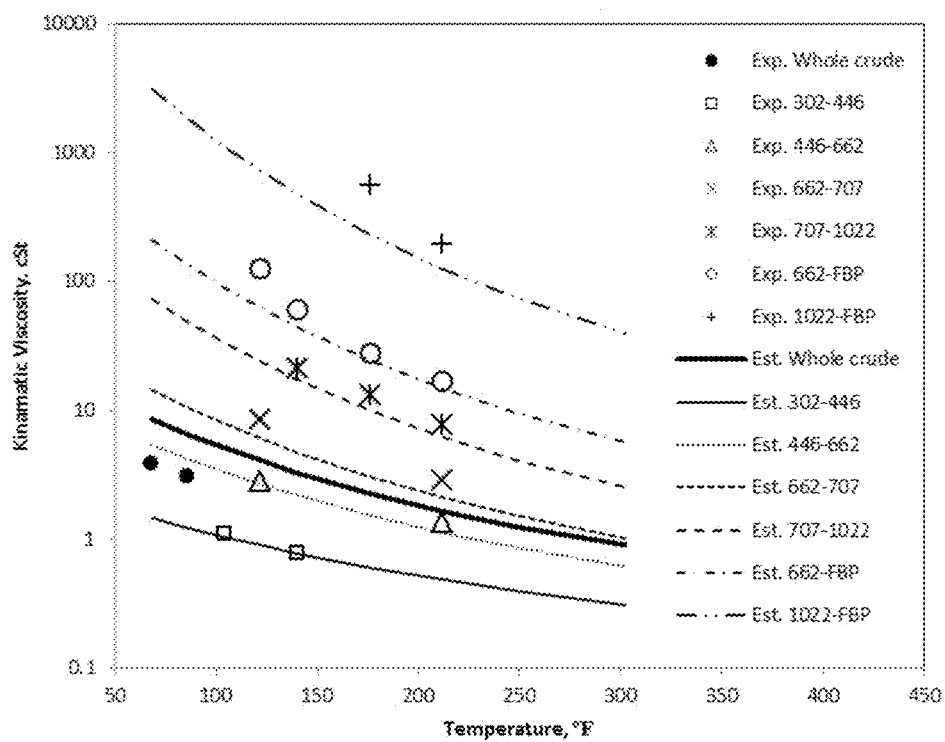
FIG. 11 is a graph of viscosity experimental assay data and model results as a function of temperature (° F.) for UK Brent crude (the Forties blend).
Figure 12:
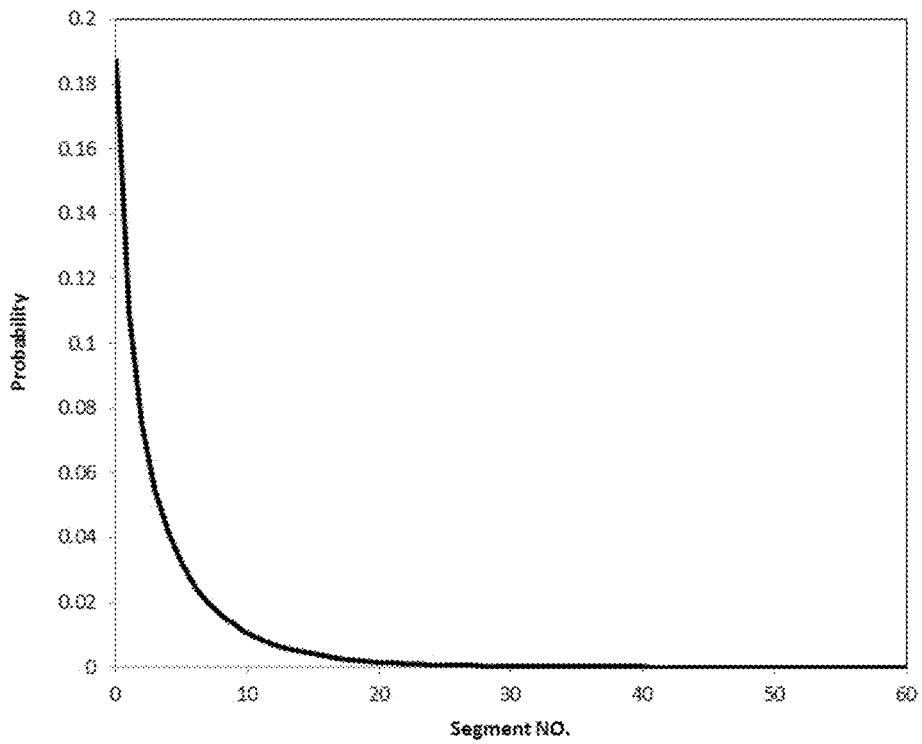
FIG. 12 is a graph of a gamma probability distribution function as a function of segment number illustrating probability of the sample values as a function of number of —$CH_2$— segments in normal paraffins.
Figure 13:
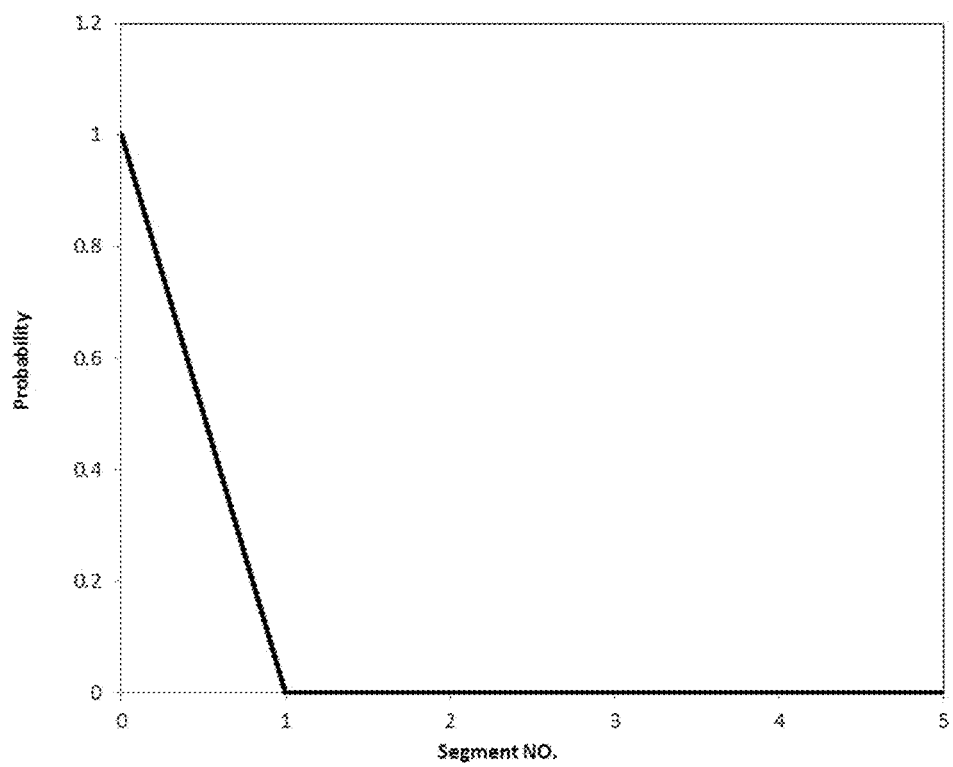
FIG. 13 is a graph of a gamma probability distribution function as a function of segment number illustrating probabilities of the sample values as a function of the number of cyclohexane side rings in naphthenes.
Figure 14:
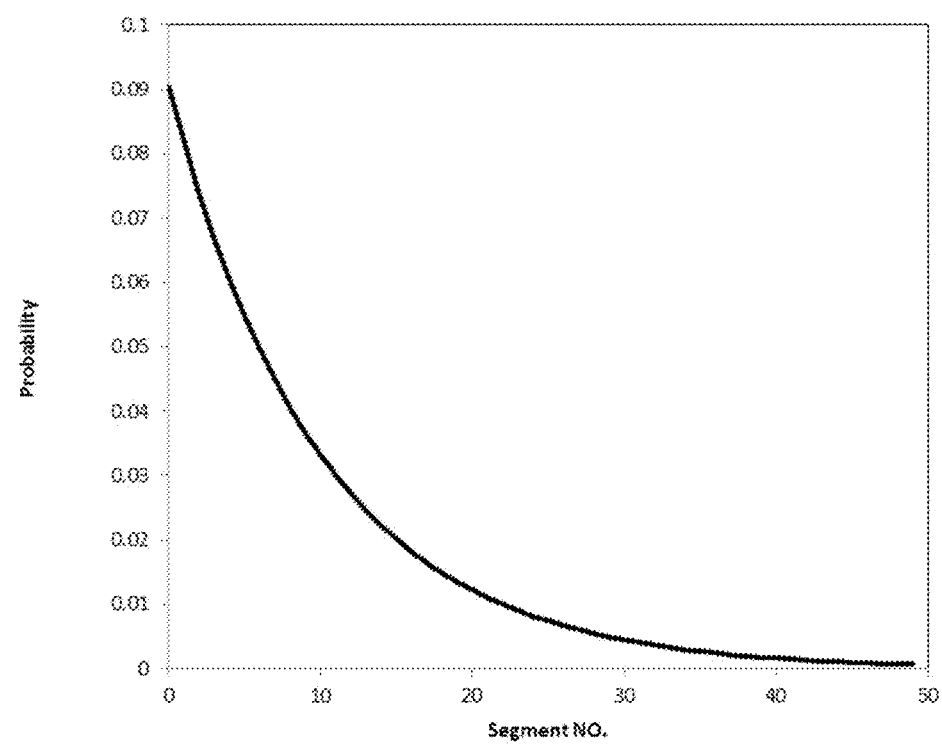
FIG. 14 is a graph of a gamma probability distribution function as a function of segment number illustrating probabilities of the sample values as a function of the number of —$CH_2$— segments in the n-alkyl side chain of the naphthenes.
Figure 15:
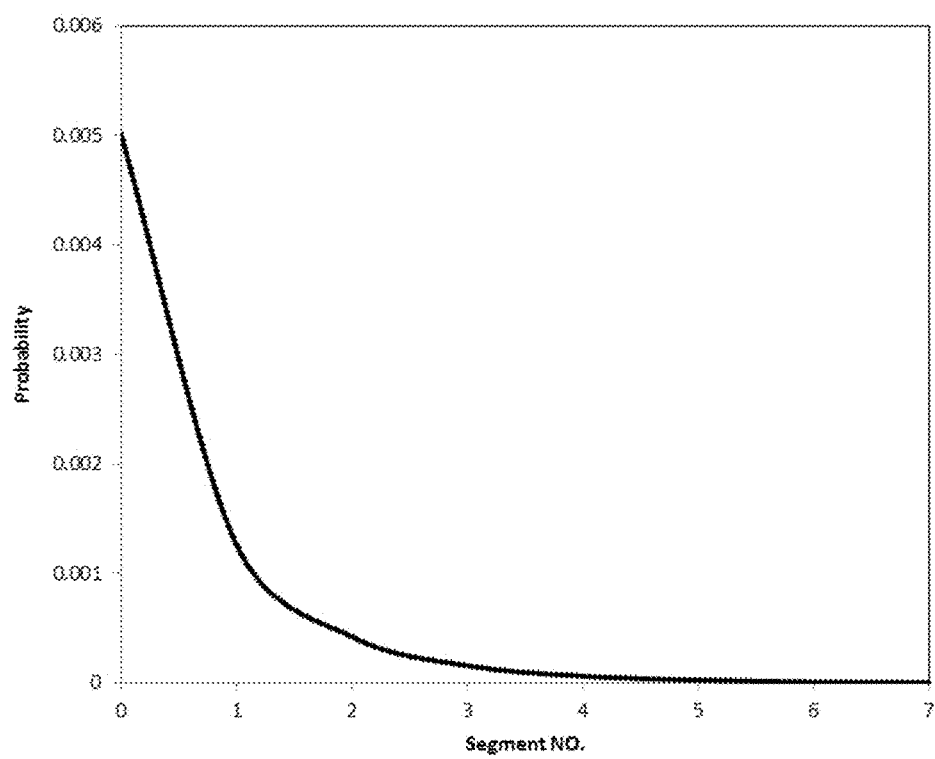
FIG. 15 is a graph of a gamma probability distribution function as a function of segment number illustrating probabilities of the sample values as a function of the number of aromatic side rings in aromatics.
Figure 16:
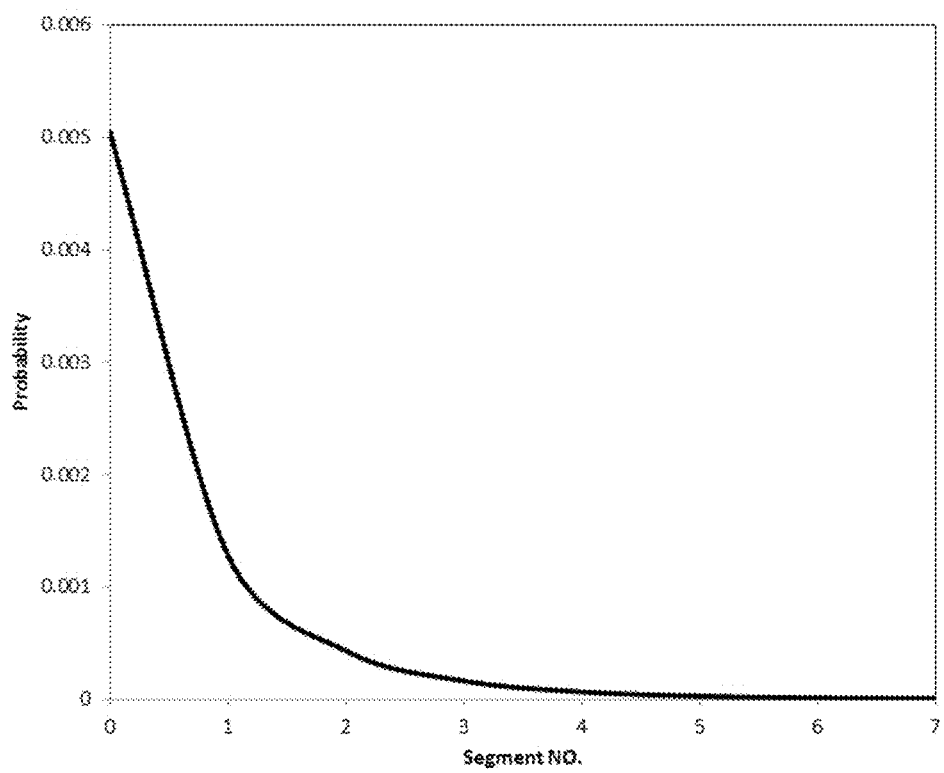
FIG. 16 is a graph of a gamma probability distribution function as a function of segment number illustrating probabilities of the sample values as a function of the number of cyclohexane side rings in aromatics.
Figure 17:
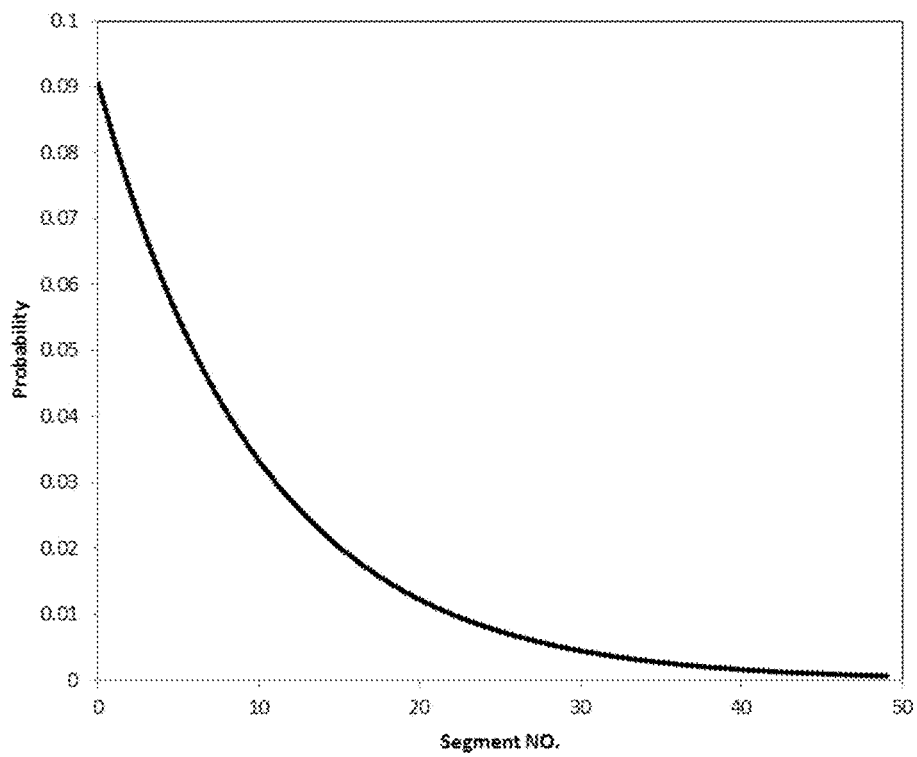
FIG. 17 is a graph of a gamma probability distribution function as a function of segment number illustrating probabilities of the sample values as a function of the number of —$CH_2$— segments in the n-alkyl side chain of the aromatics.

To illustrate by an example of a specific crude oil, FIGS. 9-11 show a set of true boiling point data, API gravity data, and crude viscosity data, respectively, for UK Brent crude (the Forties blend). See Oil & Gas Databook. These experimental assay data are regressed simultaneously to identify the hydrocarbon constituent molecule segment probability distribution function parameters, including the relative P, N, and A contents and the probability distribution function parameters for the structural segments for each class of molecules. The resulting model results of the true boiling point curve, API gravity curve, and viscosity curve are shown as solid lines in FIGS. 9, 10, and 11, respectively. Additional experimental assay data can also be included in the regression. In this specific example, the probability distribution functions and associated parameters for the structural segments and the P, N, and A contents are simultaneously adjusted in the regression to fit the true boiling point data, the API gravity data, and the viscosity data. The optimized values of these P, N, and A contents and the associated segment probability distribution functions and function parameters for the UK Brent crude (the Forties blend) are given in Table 4. Note that the interaction parameter $k_0$ for the mixture viscosity correlation (see Eq. 5 in Table 3) was also adjusted. In practice, depending on the nature of the available experimental assay data, the P, N, and A contents and the probability distribution function parameters can be sequentially or simultaneously adjusted in the regression to provide an optimal fit to the experimental assay data. The standard deviations for experimental assay data on true boiling points, densities, viscosities, and P, N, and A contents are typically about 1%, about 10%, and about 10%, respectively.

TABLE 4

Optimized values of P, N, and A contents and the associated distribution functions and function parameters for UK Brent crude (the Forties blend)

| Compound Classes | wt % | Segments | Distribution Function | Scale | Shape |
|---|---|---|---|---|---|
| P | 34.51 | —$CH_2$— | Gamma | 6.53 | 0.44 |
|  |  |  | Uniform | — | — |

TABLE 4-continued

Optimized values of P, N, and A contents and the associated distribution functions and function parameters for UK Brent crude (the Forties blend)

| Compound Classes | wt % | Segments | Distribution Function | Scale | Shape |
|---|---|---|---|---|---|
| | | (iso-paraffin branch) | Gamma | 0.024 | 94.66 |
| N | 13.14 | (cyclohexane ring) | Gamma | 0.01 | 0.06 |
| | | —CH$_2$—$^a$ | Gamma | 10 | 1 |
| | | —CH$_2$—$^b$ | Uniform | — | — |
| | | —CH$_3$ | Uniform | — | — |
| | | N6/(N5 + N6)$^c$ | Value | 0.12 | |
| A | 52.35 | (aromatic ring) | Gamma | 1.44 | 0.01 |
| | | (cyclohexene ring) | Gamma | 1.46 | 0.01 |
| | | —CH$_2$— | Gamma | 10 | 1 |
| | | —CH$_3$ | Uniform | — | — |
| Viscosity Parameters | | k$_0$ | | −0.71 | |

Figure 18:
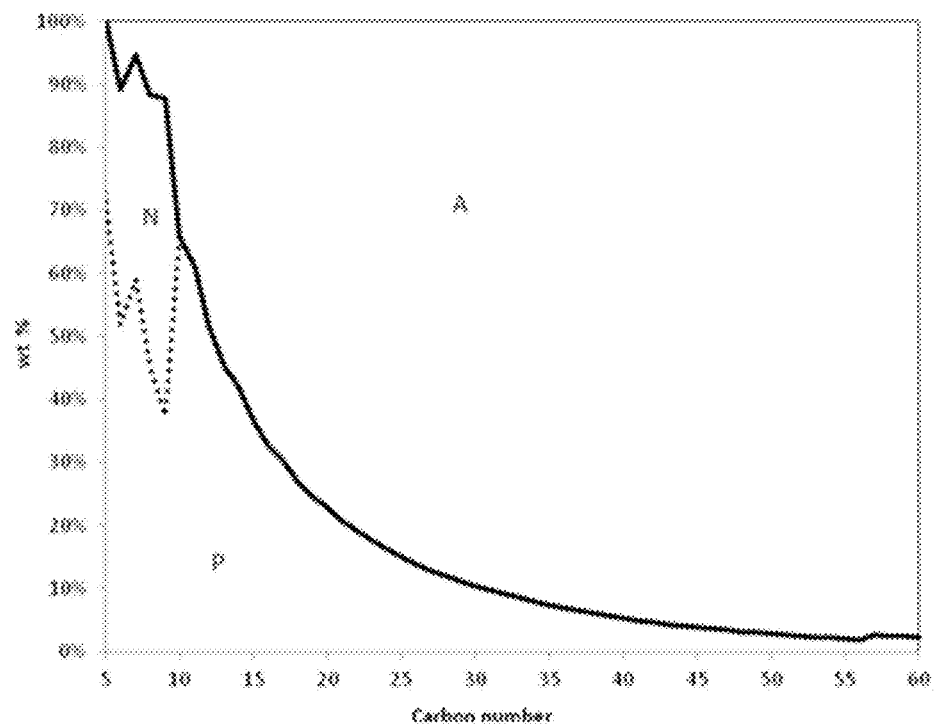
FIG. 18 is a graph of normalized weight percentages as a function of carbon number illustrating the distribution of paraffins, naphthenes, and aromatics as a function of carbon number.
Figure 19:
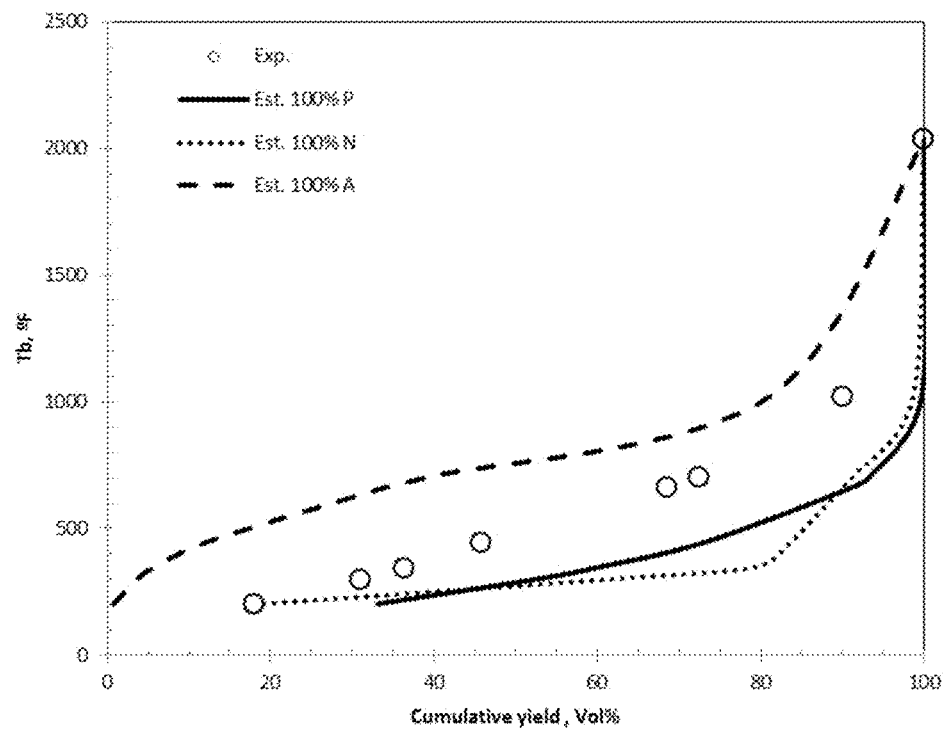
FIG. 19 is a graph of true boiling point (° F.) as a function of cumulative distilled (vol %) showing model results of true boiling points for UK Brent crude (the Forties blend) by 100% paraffin, 100% naphthene, and 100% aromatics.
Figure 20:
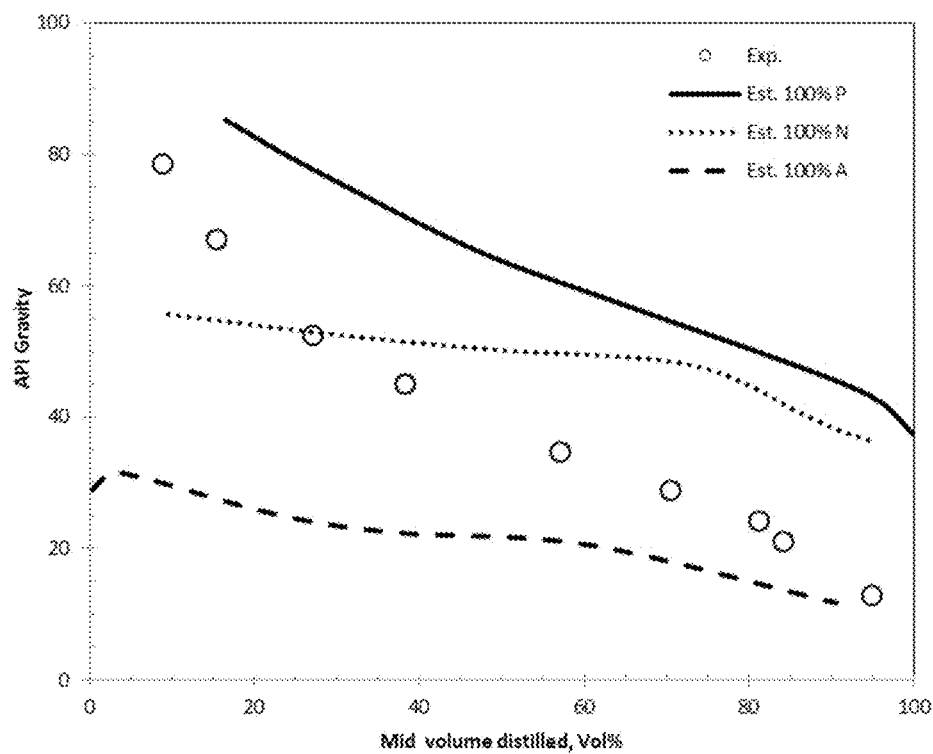
FIG. 20 is a graph of API gravity as a function of mid volume distilled (vol %) showing model results of API gravities for UK Brent crude (the Forties blend) by 100% paraffin, 100% naphthene, and 100% aromatics.

Notes:
$^a$The —CH$_2$— segment in the side chains on cyclohexane naphthenic molecules
$^b$The —CH$_2$— segment in the side chains on cyclopentane naphthenic molecules
$^c$N6/(N5 + N6) is the mole ratio of cyclohexane naphthenic molecules over all the naphthenic molecules FIGS. 12-17 show the probability distribution functions of the sample values for the number of the segments for which the gamma distribution is applied. The probabilities are based on the gamma distribution function parameters reported in Table 4. FIG. 18 shows the distributions of normalized weight percentages of different classes of molecules as a function of the total carbon number in the molecules. FIGS. 19 and 20 show the model results of the true boiling point curves and API gravity curves for the hypothetical 100% P, 100% N, and 100% A crude oils as calculated with the specific segment probability distribution function parameters summarized in Table 4. Together with the relative P, N, and A contents, one can obtain the true boiling point curve, the API gravity curve, and the viscosity curve shown in FIGS. 9, 10, and 11, respectively, for the Forties blend crude. The same methodology described above for identifying the molecular distribution parameters can be applied directly to petroleum fractions which have limited boiling point ranges.

Generating Complete Assays and Properties

Given the molecular distribution parameters for crude oil, various molecular thermodynamic models such as PC-SAFT EOS, group contribution methods, and other methods can be applied to predict a wide variety of physical and chemical properties for crude oil including vapor pressure, density, viscosity, paraffin content, naphthene content, aromatic content, carbon content, hydrogen content, C/H ratio, asphaltene content, carbon residue, sulfur content, nitrogen content, total acid number, molecular weight, heat capacity, heating value, heat of vaporization, cloud point, aniline point, wax content, etc. Conversely, if data are available for these physical and chemical properties, they can be used in the regression methodology described above to identify optimal molecular distribution parameters.

Figure 21:
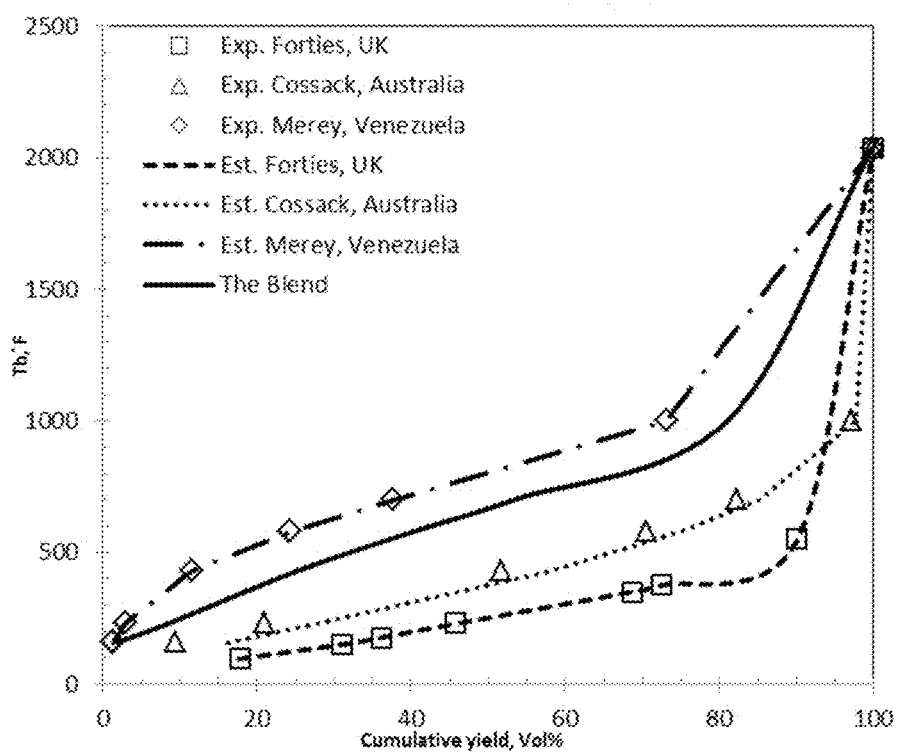
FIG. 21 is a graph of true boiling point data from three crude assays and model predictions as a function of volume distilled (vol %) for a blended crude assay.
Figure 22:
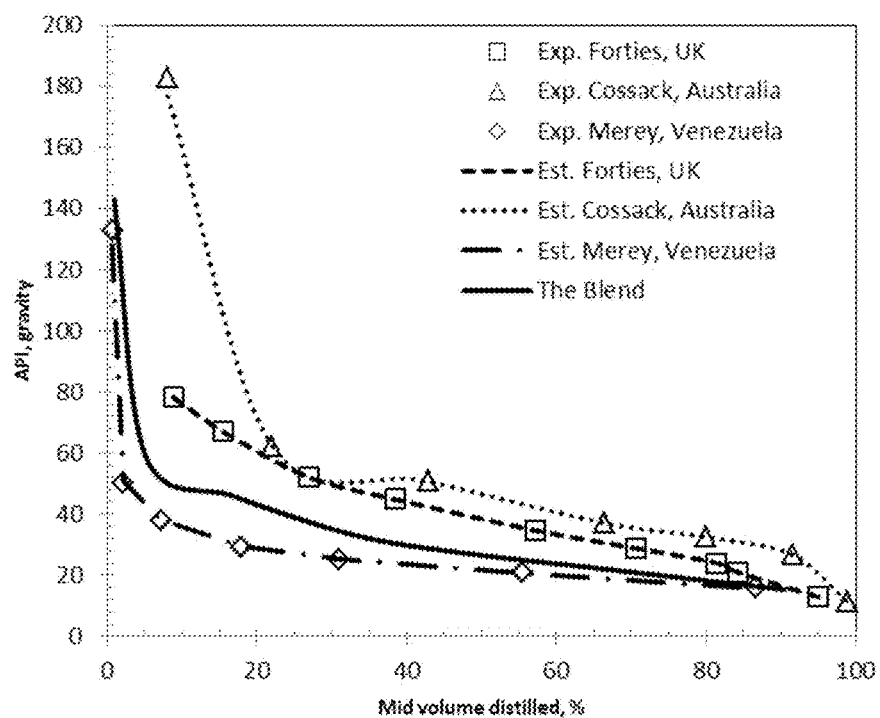
FIG. 22 is a graph of API gravity measurement data from three crude assays and model predictions as a function of volume distilled (vol %) for a blended crude assay.

The molecular distribution parameters for crude oil further provide the molecular basis for crude oil blending calculations. Traditionally, an arbitrary set of pseudocomponents is applied to all crude oil to be blended, and crude blending is then performed on the pseudocomponent level. See Aspen HYSYS v7.3. In contrast, no such pseudocomponents are required for crude blending with the molecule-based approach. Here, the chemical compositions of blended crude oil are simply the sum of the chemical compositions of individual crude oils. Assay properties of a blend can be rigorously computed based on its molecular representation without the need to go through the artificial step of generating pseudocomponents. FIGS. 21 and 22 show the model-predicted true boiling point and API gravity, respectively, for a blend made from three crude oils. The same methodology described above for modeling crude oil assays and their blends can be applied directly to blending petroleum fractions which have limited boiling point ranges.

Molecule-Based Methodology for Planning, Scheduling, and Process Simulation

As mentioned earlier, crude assays are often used to generate a certain limited number of "pseudocomponents" or "hypothetical components" and their compositions are then used to represent the petroleum mixtures for the purpose of planning, scheduling, and process simulation of petroleum refining processes such as fractionations and reactions. Properties of pseudocomponents are defined to mimic a fraction of the crude assay, i.e., with specific ranges of boiling point and specific gravity. The molecular characterization approach offers not only a superior methodology to correlate and predict full assays that subsequently can be used to generate "pseudocomponents," it also offers an important new alternative to this traditional "pseudocomponent" approach for planning, scheduling and process simulation. Specifically, the model molecules and their compositions associated with the molecular distribution parameters can be used directly to represent crude oil and petroleum fractions in planning, scheduling, and process simulation of petroleum refining operations.

Computer Implementation

Figure 23A:
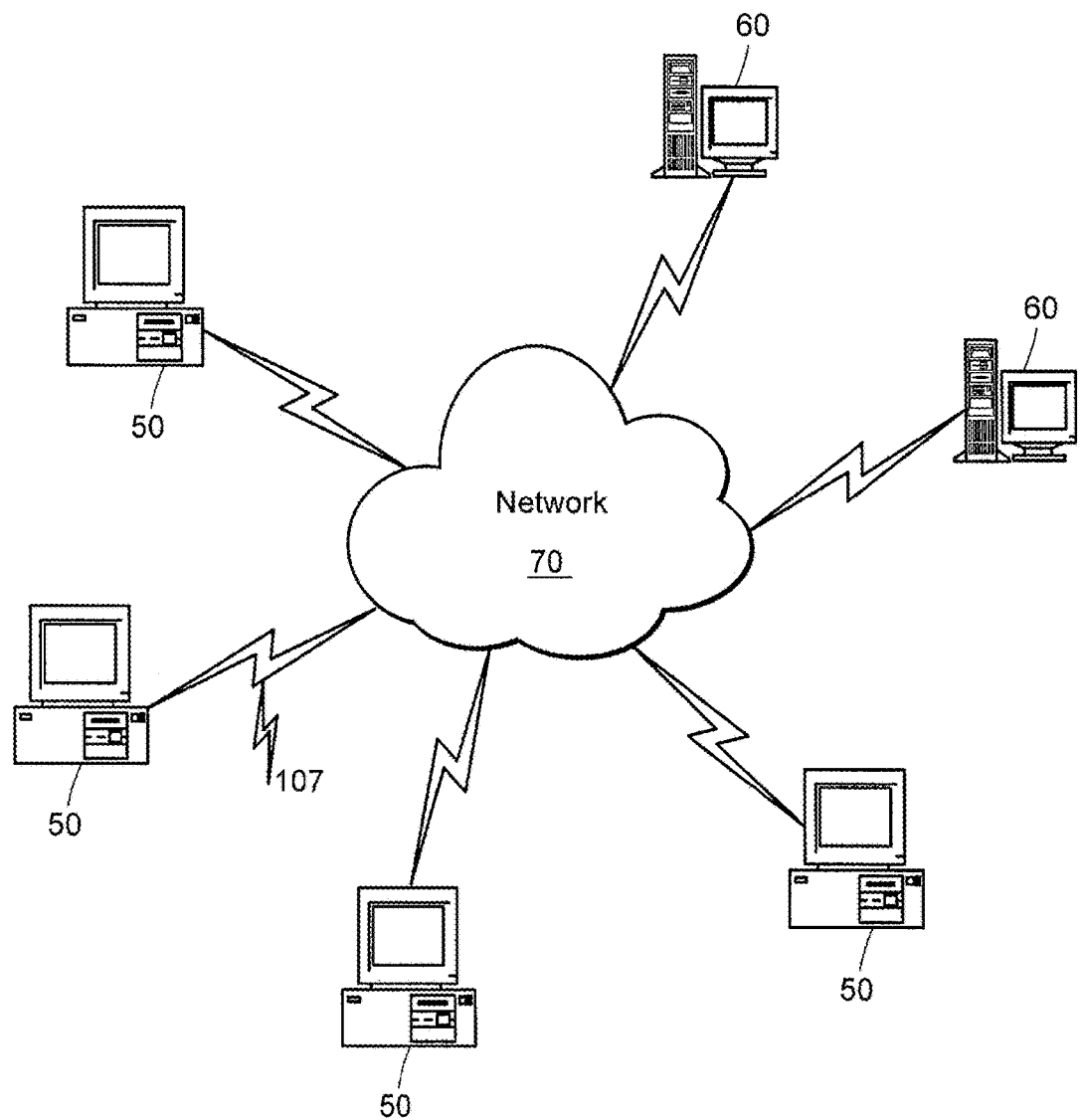
FIGS. 23A and 23B are schematic views of a computer system and network implementation of the present invention.
Figure 23B:
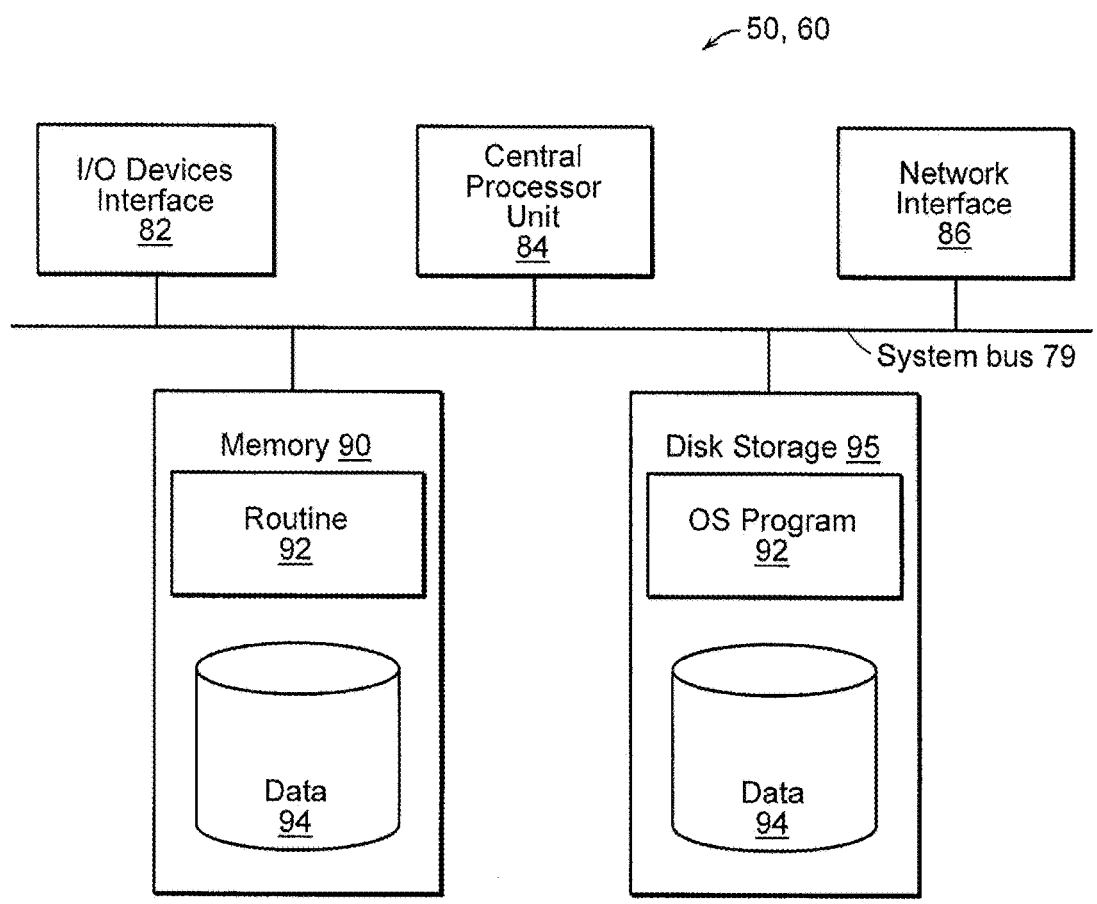
Figure 24:
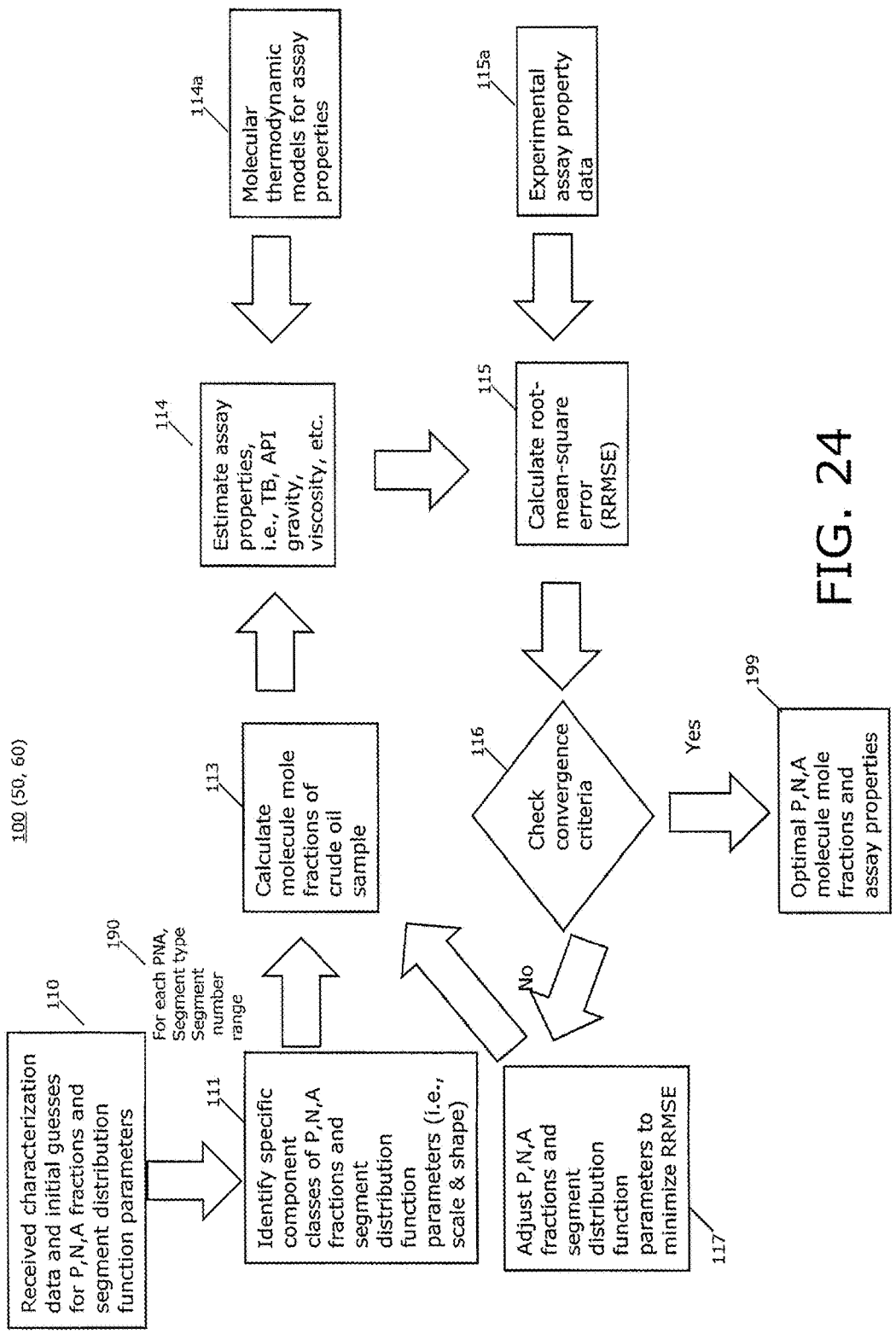
FIG. 24 is a flow diagram of one embodiment of the present invention.
Figure 25:
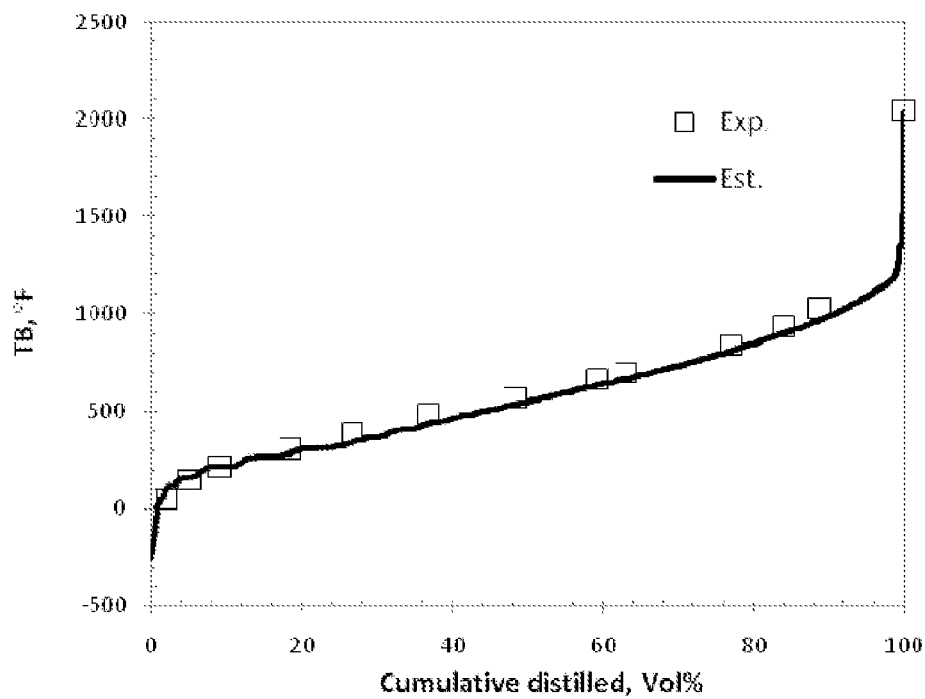
FIG. 25 is an illustration of model results for true boiling points for the crude oil Azeri BTC 2009 01.
Figure 26:
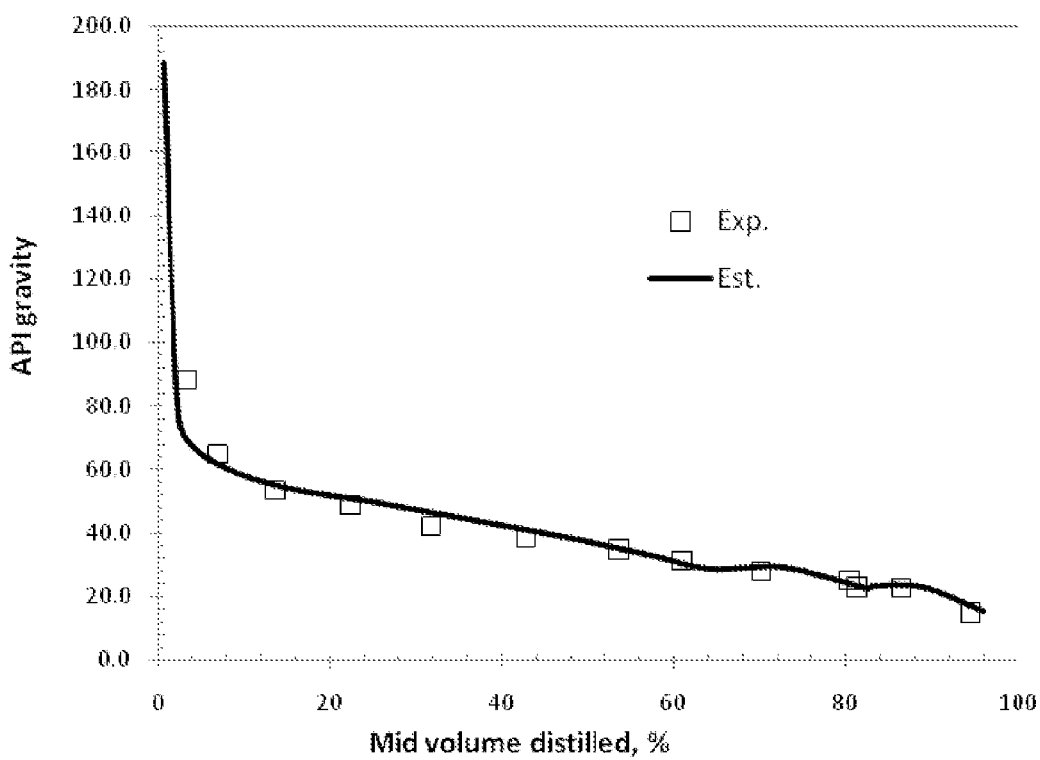
FIG. 26 is an illustration of model results for API gravities for the crude oil Azeri BTC 2009 01.
Figure 27:
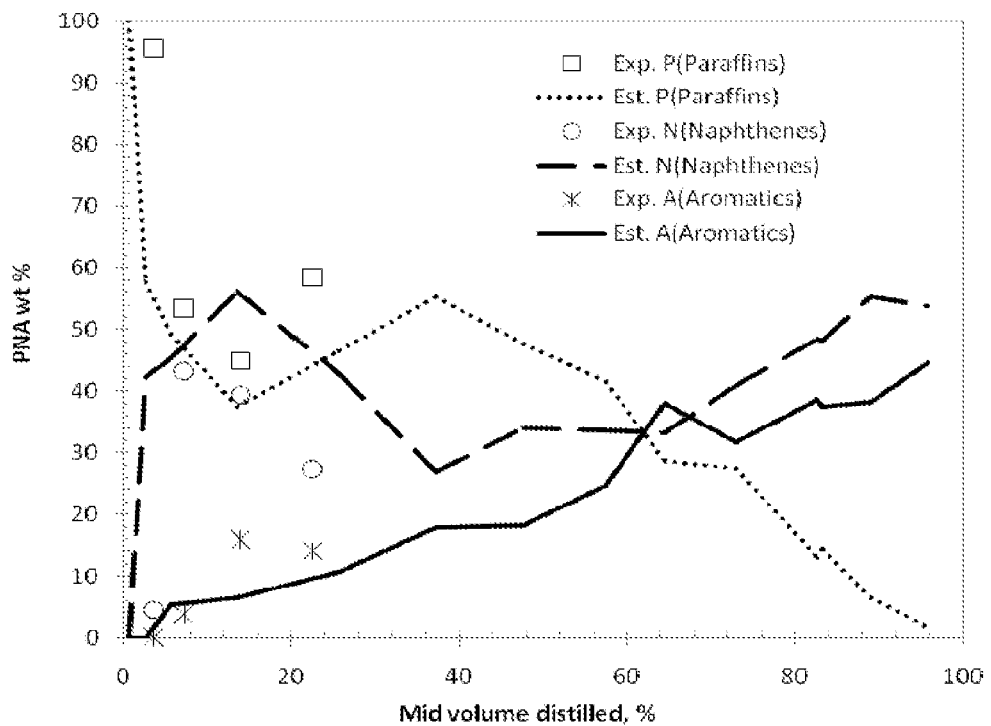
FIG. 27 is an illustration of model results for normalized PNA distributions for the crude oil.
Figure 28:
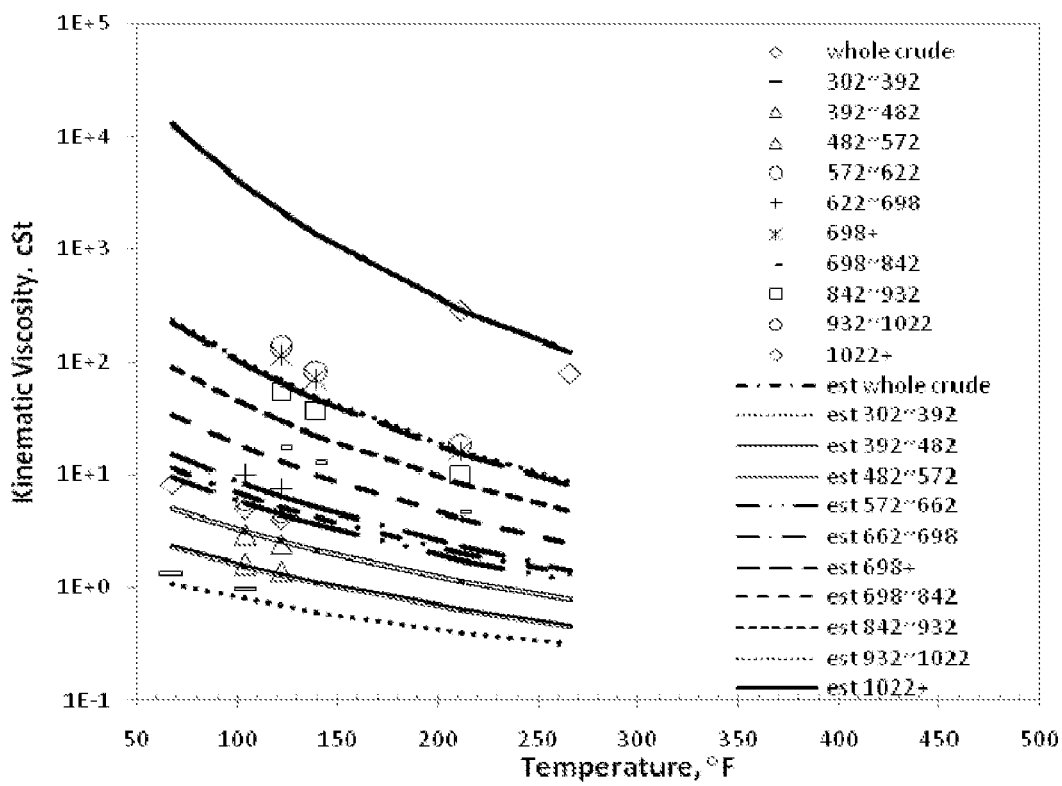
FIG. 28 is an illustration of model results for viscosities for the crude oil Azeri BTC 2009 01.
Figure 29:
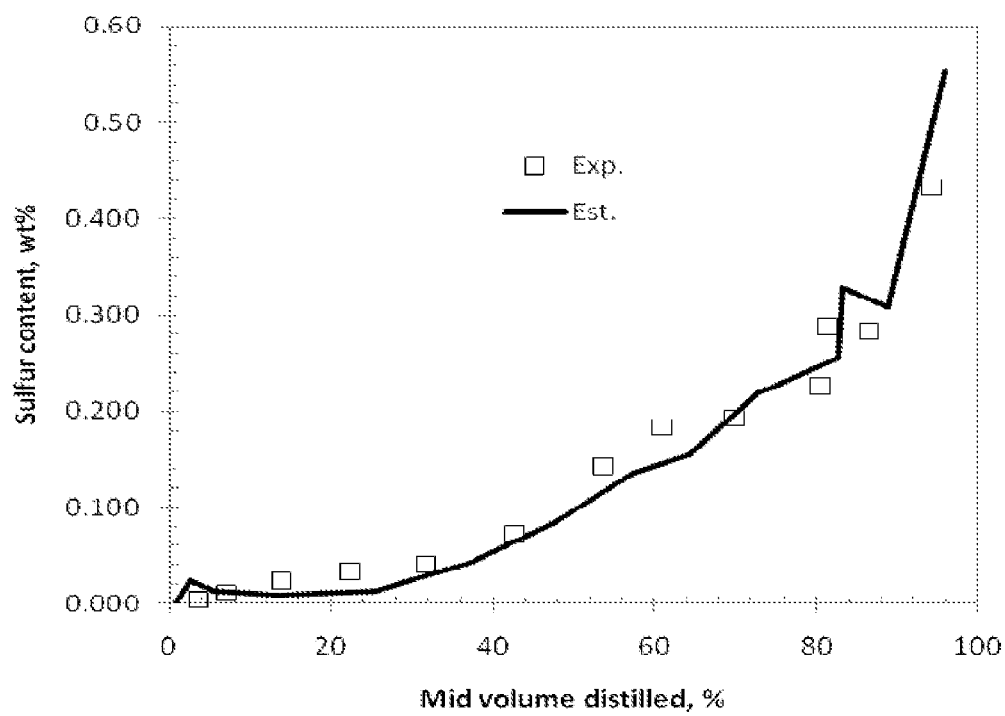
FIG. 29 is an illustration of model results for sulfur content for the crude oil Azeri BTC 2009 01.
Figure 30:
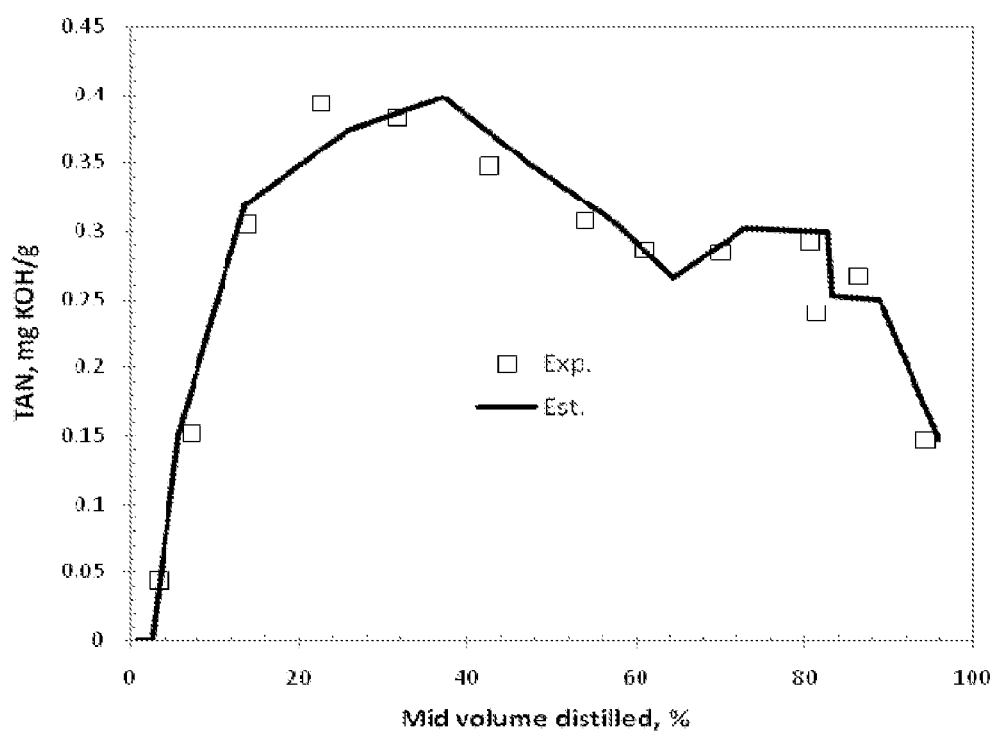
FIG. 30 is an illustration of model results for total acid number for the crude oil Azeri BTC 2009 01.

Turning now to FIGS. 23A, 23B and 24, a computer system embodying the present invention is shown and described. It is understood that other computer architectures and configurations are suitable and in the purview of one skilled in the art given this description.

FIG. 23A illustrates a computer network or similar digital processing environment in which the present invention may be implemented.

Client computer(s)/devices 50 and server computer(s) 60 provide processing, storage, and input/output devices executing application programs and the like. Client computer(s)/devices 50 can also be linked through communications network 70 to other computing devices, including other client devices/processes 50 and server computer(s) 60. Communications network 70 can be part of a remote access network, a global network (e.g., the Internet), a worldwide collection of computers, Local area or Wide area networks, and gateways that currently use respective protocols (TCP/IP, Bluetooth, etc.) to communicate with one another. Other electronic device/computer network architectures are suitable.

FIG. 23B is a diagram of the internal structure of a computer (e.g., client processor/device 50 or server computers 60) in the computer system of FIG. 23A. Each computer 50, 60 contains system bus 79, where a bus is a set of hardware lines used for data transfer among the components of a computer or processing system. Bus 79 is essentially a shared conduit that connects different elements of a computer system (e.g., processor, disk storage, memory, input/output ports, network ports, etc.) that enables the transfer of information between the elements. Attached to system bus 79 is I/O device interface 82 for connecting various input and output devices (e.g., keyboard, mouse, displays, printers, speakers, etc.) to the computer 50, 60. Network interface 86 allows the computer to connect to various other devices attached to a network (e.g., network 70 of FIG. 23A). Memory 90 provides volatile storage for computer software instructions 92 and data 94 used to implement an embodiment of the present invention (e.g., virtual assay engine, crude oil assay modeler, and supporting code 100 detailed above and below). Disk storage 95 provides non-volatile storage for computer software instructions 92 and data 94 used to implement an embodiment of the present invention. Central processor unit 84 is also attached to system bus 79 and provides for the execution of computer instructions.

In one embodiment, the processor routines 92 and data 94 are a computer program product (generally referenced 92), including a computer readable medium (e.g., a removable storage medium such as one or more DVD-ROM's, CD-ROM's, diskettes, tapes, etc.) that provides at least a portion of the software instructions for the invention system. Computer program product 92 can be installed by any suitable software installation procedure, as is well known in the art. In another embodiment, at least a portion of the software instructions may also be downloaded over a cable, communication and/or wireless connection. In other embodiments, the invention programs are a computer program propagated signal product 107 embodied on a propagated signal on a propagation medium (e.g., a radio wave, an infrared wave, a laser wave, a sound wave, or an electrical wave propagated over a global network such as the Internet, or other network(s)). Such carrier medium or signals provide at least a portion of the software instructions for the present invention routines/program 92.

In alternate embodiments, the propagated signal is an analog carrier wave or digital signal carried on the propagated medium. For example, the propagated signal may be a digitized signal propagated over a global network (e.g., the Internet), a telecommunications network, or other network. In one embodiment, the propagated signal is a signal that is transmitted over the propagation medium over a period of time, such as the instructions for a software application sent in packets over a network over a period of milliseconds, seconds, minutes, or longer. In another embodiment, the computer readable medium of computer program product 92 is a propagation medium that the computer system 50 may receive and read, such as by receiving the propagation medium and identifying a propagated signal embodied in the propagation medium, as described above for computer program propagated signal product.

Generally speaking, the term "carrier medium" or transient carrier encompasses the foregoing transient signals, propagated signals, propagated medium, storage medium and the like.

Illustrated in FIG. 24 is an exemplary flow diagram of a virtual assay or crude oil assay modeler of the present invention (generally indicated as engine or modeler 100). The flow of data and processor 84 control is provided for purposes of illustration and not limitation. It is understood that processing may be in parallel, distributed across multiple processors, in different order than that shown or otherwise programmed to operate in accordance with the principles of the present invention.

Virtual assay engine/assay modeler 100 begins with receipt (110) of data indicative of a crude oil sample or subject petroleum fraction. Included is certain characterization data (of the type common in the industry) of the crude oil sample/petroleum fraction, for example boiling point, density and viscosity. Step 110 initializes engine/modeler 100 with the received data.

In turn, for each crude, step 111 identifies the specific classes of hydrocarbon constituent molecules (i.e., P, N, A fractions) and identifies the probability distribution function of the identified classes. In particular, step 111 identifies the scale and shape parameters of each probability distribution function (see e.g., Eq. 4). As a result, step 111 outputs for each P, N, A class, a segment type and segment number range (generally 190) of the hydrocarbon constituent molecules useable by, for example, PC-SAFT. Step 111 outputs the segment type and segment number range without the use of homologous series.

Next, steps 113-117 optimize the identified classes of hydrocarbon constituent molecules (i.e., candidate compositions) to fit the crude oil sample/petroleum fraction characterization data received at step 110. Step 113 calculates the molecule mole fractions of the crude oil sample/petroleum fraction. As described above, the PC-SAFT equation-of-state and/or similar molecular thermodynamic models for assay properties 114a are then used, at step 114, to estimate the physical properties of hydrocarbon constituent molecules for the crude oils and their mixtures. The resulting molecular composition produces an outcome crude oil/petroleum fraction with physical properties closely matching those stated in the characterization data of the crude oil sample/subject petroleum fraction. Step 115 calculates the difference between the estimated and experimental assay property data 115a. The resulting relative ratio of P, N, A fractions (hydrocarbon constituent molecules) is checked against convergence criteria at step 116 and adjusted, if necessary, at step 117, followed by another iteration of the optimization steps 113-117. The resulting optimized assay output 199 represents or otherwise characterizes the chemical composition of the sample crude oil/subject petroleum fraction. In this way, output 199 serves as a molecular model of the sample crude oil/subject petroleum fraction that more comprehensively characterizes its properties (e.g., boiling point, density, and viscosity) and other assay results (e.g., composition).

This assay output 199 (characterization of the chemical composition of the sample crude oil/subject petroleum fraction) is in turn useable by other software programs and applications to predict physical properties of the sample crude oil/subject petroleum fraction, and thus to plan, schedule, simulate, design, optimize and/or control petroleum refining operations thereof.

EXEMPLIFICATION

The molecule-based characterization methodology has been developed for correlation and prediction of assays and properties for crude oil and petroleum fractions. The approach allows identification of representative chemical compositions of pre-selected model hydrocarbon constituent molecules for crude oil and petroleum fractions from regression of limited assay data. It also allows prediction of assays and related physical and chemical properties for crude oil and petroleum fractions from such chemical compositions.

The following three crude oil characterization examples illustrate how the molecule-based characterization approach works. The first example is a light crude Azeri BTC 2009 01 with API gravity of 36.6 and the second one is a heavy crude Grane 2003 11 with API gravity of 18.7. The third example is a blend crude composed of 60% Azeri BTC 2009 01 and 40% Grane 2003 11.

1. Light Crude Oil—Azeri BTC 2009 01

1.1 General Information

Azeri BTC 2009 01 is the assay, available from Statoil, for a light crude from Azerbaijan. (Statoil, Stamford Conn.). Assay data for wide varieties of properties are available, including Distillation Yield, Density, Universal Oil Products (UOP) K Factor (UOPK), Molecular Weight, Total Sulfur, Mercaptan Sulfur, Total Nitrogen, Basic Nitrogen, Total Acid Number (TAN), Viscosity, PNA distributions, RON & MON, Pour Point, Cloud Point, Freeze Point, Smoke Point, Cetane Index, Aniline Point, Wax Content, Hydrogen Content, Asphaltene Content, and Micro Carbon Residue.

In the example, assay data for Distillation Yield, Density, Viscosity, PNA distributions, Asphaltene Content, Total Sulfur, and Total Acid Number properties are regressed to identify the optimal molecular distribution parameters and the chemical compositions of hydrocarbon constituent molecules designed to best correlate the available crude oil characterization data and to predict missing data.

Table 1 shows the bulk properties of this crude oil.

TABLE 1

| Bulk properties for Azeri BTC 2009 01 | | | | | | | | | |
|---|---|---|---|---|---|---|---|---|---|
| API Gravity | Sulfur, % | TAN., mg KOH/g | Kin. Vis, cSt | | | Paraffins, wt % | Naphthenes, wt % | Aromatics, wt % | Asphaltene, wt % |
| | | | 20 | 40 | 50 | | | | |
| 36.6 | 0.155 | 0.312 | 8.21 | 4.99 | 4.04 | 33.5 | 44.3 | 22.2 | 0.0285 |

1.2 Experimental Data Used in Regression

Table 2 shows the regressed experimental data from the Statoil assay for the whole crude, gas, and boiling point cuts 1-13 for Distillation Yield, API Gravity data, PNA Distributions, Viscosity, Sulfur Content, Asphaltene Content, and Total Acid Number for Azeri BTC 2009 01.

TABLE 2

| Experimental data used in regression for Azeri BTC 2009 01 | | | | | | | | | | | | | | | | |
|---|---|---|---|---|---|---|---|---|---|---|---|---|---|---|---|---|
| Cuts | Whole crude | Gas | Cut 1 | Cut 2 | Cut 3 | Cut 4 | Cut 5 | Cut 6 | Cut 7 | Cut 8 | Cut 9 | Cut 10 | Cut 11 | Cut 12 | Cut 13 |
| IBP[a] (° F.) | | C1 | 48 | 149 | 212 | 302 | 392 | 482 | 572 | 662 | 698 | 698 | 842 | 932 | 1022 |
| FBP[b] (° F.) | | 48 | 149 | 212 | 302 | 392 | 482 | 572 | 662 | 698 | FBP[b] | 842 | 932 | 1022 | FBP[b] |
| Yield, vol % | | 2.03 | 3.2 | 4.1 | 9.1 | 8.3 | 10.3 | 11.6 | 10.6 | 3.8 | 37.0 | 14.2 | 6.8 | 4.9 | 11.1 |
| Gravity (API) | 36.6 | | 88.1 | 65.1 | 53.7 | 48.8 | 42.2 | 38.4 | 34.4 | 31.3 | 22.5 | 28.0 | 25.1 | 22.8 | 14.5 |
| Paraffins, wt % | 33.5 | | 95.5 | 53.3 | 45.0 | 58.4 | | | | | | | | | |
| Naphthenes, wt % | 44.3 | | 4.5 | 43.0 | 39.2 | 27.4 | | | | | | | | | |
| Aromatics, wt % | 22.2 | | 0.0 | 3.7 | 15.8 | 14.2 | | | | | | | | | |
| Sulfur, wt % | 0.155 | | 0.005 | 0.011 | 0.023 | 0.033 | 0.041 | 0.072 | 0.141 | 0.184 | 0.287 | 0.193 | 0.225 | 0.283 | 0.433 |
| Kin. Vis, cSt @ 20° C. | 8.21 | | | | | 1.31 | | | | | | | | | |
| Kin. Vis, cSt @ 40° C. | 4.99 | | | | | 0.97 | 1.59 | 2.90 | 5.70 | 10.1 | | | | | |
| Kin. Vis, cSt @ 50° C. | 4.04 | | | | | | 1.37 | 2.41 | 4.52 | 7.58 | 112 | 17.1 | 54.6 | 133 | |
| Kin. Vis, cSt @ 60° C. | | | | | | | | | | | 69.1 | 12.5 | 35.8 | 80.5 | |
| Kin. Vis, cSt @ 100° C. | | | | | | | | | | | 16.3 | 4.65 | 10.1 | 18.2 | 283 |
| Kin. Vis, cSt @ 130° C. | | | | | | | | | | | | | | | 78.2 |
| Asphaltene, wt % | 0.0285 | | | | | | | | | | 0.1 | | 0.0 | 0.0 | 0.2 |
| TAN., mg KOH/g | 0.312 | | 0.043 | 0.152 | 0.305 | 0.394 | 0.383 | 0.347 | 0.308 | 0.286 | 0.240 | 0.284 | 0.291 | 0.267 | 0.147 |

Notes:
[a] Initial boiling point for each cut;
[b] Final boiling point for each cut.

1.3 Molecular Characterization Results
1.3.1 Optimized Values

All the data in Table 2 (obtained from the Statoil assay) are regressed to identify the relative weights of various classes of hydrocarbon constituent molecules including paraffins, naphthenes, aromatics, sulfides, mercaptans, naphthenic sulfides, thiophenes, paraffinic acids, naphthenic acids, and aromatic acids listed in Table 3. Also identified in Table 3 are the probability distribution function parameters for each class of these molecules. The interaction parameter $k_0$ and asphaltene related parameters $k_1$, $k_2$ and $k_3$ for the mixture viscosity correlation are also adjusted. Depending on the nature of the available experimental data, the individual molecule class weight content, the probability distribution function parameters, and the viscosity correlation parameters can be simultaneously or sequentially regressed to obtain an optimal fit to the data.

The optimized values for the molecular distribution parameters for crude oil Azeri BTC 2009 01 are given in Table 3. Note that, in the regression, values of probability distribution parameters for sulfides and mercaptans are set to be same as those for paraffin molecules. Also, values for naphthenic sulfides distribution parameters are set the same as those for naphthene molecules.

TABLE 3

Optimized values for the molecular distribution parameters for Azeri BTC 2009 01

| Molecule Classes | wt % | Segments | Distribution Function | Scale | Shape |
|---|---|---|---|---|---|
| Paraffins | 34.08 | —CH$_2$— | Gamma | 5.014 | 1.352 |
|  |  | (branch) | Uniform | N/A | N/A |
|  |  | (branch) | Uniform | N/A | N/A |
| Naphthenes | 42.06 | (ring) | Gamma | 1.744 | 0.477 |
|  |  | —CH$_2$—$^{(a)}$ | Gamma | 20.312 | 0.525 |
|  |  | —CH$_2$—$^{(b)}$ | Uniform | N/A | N/A |
|  |  | —CH$_3$ | Uniform | N/A | N/A |
|  |  | N6/(N5 + N6)$^{(c)}$ | Alternative | 0.794 |  |
| Aromatics | 23.03 | (aromatic ring) | Gamma | 0.785 | 2.049 |
|  |  | (ring) | Gamma | 0.01 | 0.481 |
|  |  | —CH$_2$— | Gamma | 5.360 | 1.457 |
|  |  | —CH$_3$ | Uniform | N/A | N/A |
| Sulfides | 0 | —CH$_2$— | Gamma | Set the same value as paraffins |  |
| Mercaptans | 0.0125 | —CH$_2$— | Gamma | Set the same value as paraffins |  |
| Naphtenic sulfides | 0.00 | (ring) | Gamma | set the same value as naphthenes |  |
|  |  | —CH$_2$—$^{(a)}$ | Gamma | set the same value as naphthenes |  |
|  |  | —CH$_2$—$^{(b)}$ | Gamma | set the same value as naphthenes |  |
|  |  | —CH$_3$ | Uniform | N/A | N/A |
|  |  | N6/(N5 + N6)$^{(c)}$ | Alternative | set the same value as naphthenes |  |

TABLE 3-continued

Optimized values for the molecular distribution parameters for Azeri BTC 2009 01

| Molecule Classes | wt % | Segments | Distribution Function | Scale | Shape |
|---|---|---|---|---|---|
| Thiophenes | 0.6826 |  | Gamma | 0.819 | 2.672 |
| | | —$CH_2$— | Gamma | 1.325 | 8.361 |
| | | —$CH_3$ | Uniform | N/A | N/A |
| Paraffinic acids | 0.0253 | —$CH_2$— | Gamma | 0.798 | 6.904 |
| Naphthenic acids | 0.0795 |  | Gamma | 0.01 | 13.980 |
| | | Side chain carbon no. | Gamma | 8.830 | 1.834 |
| Aromatic acids | 0.0190 |  | Gamma | 3.468 | 0.01 |
| | |  | Gamma | 0.01 | 0.948 |
| | | Side chain carbon no. | Gamma | 0.0915 | 93.112 |
| Viscosity parameters | $k_0$ | −1.398 | | | |
| | $k_1$ | 27.695 | | | |
| | $k_2$ | 27148.7 | | | |
| | $k_3$ | 10000 | | | |

Notes:
(1)
[a]The —$CH_2$— segment in the side chains on cyclohexane-based naphthenic molecules.
[b]The —$CH_2$— segment in the side chains on cyclopentane-based naphthenic molecules.
[c]N6/(N5 + N6) is the mole ratio of cyclohexane-based naphthenic molecules over all the naphthenic molecules.
(2) Gamma distribution function is applied to calculate the probabilities of the number of segments selected to make up the molecules for all classes.
(3) Parameter of location in gamma distribution function is fixed at −1 for all segments.
(4) $k_0$, $k_1$, $k_2$, and $k_3$ are parameters for mixture viscosity correlation. $k_0$ represents the interaction between paraffins, naphthenes, and aromatics. $k_1$, $k_2$, and $k_3$ are related to asphaltene content. $k_1$ is a first order asphaltene content-dependent parameter. $k_2$ is a temperature-dependent parameter. $k_3$ is a second order asphaltene content-dependent parameter.

1.3.2 Properties Plots

Calculated with the optimized molecular distribution parameters summarized in Table 3, FIGS. 25-30 show the model-predicted true boiling point curve, API gravity curve, PNA distributions curves, viscosity curves for whole crude and its fractions, sulfur content curve, and total acid number curve for the crude oil Azeri BTC 2009 01, respectively

1.3.3 Molecule Distribution Plots

The optimized molecular distribution parameters further provide a basis to determine the chemical compositions of the crude oil in terms of the model hydrocarbon constituent molecules.

Figure 31:
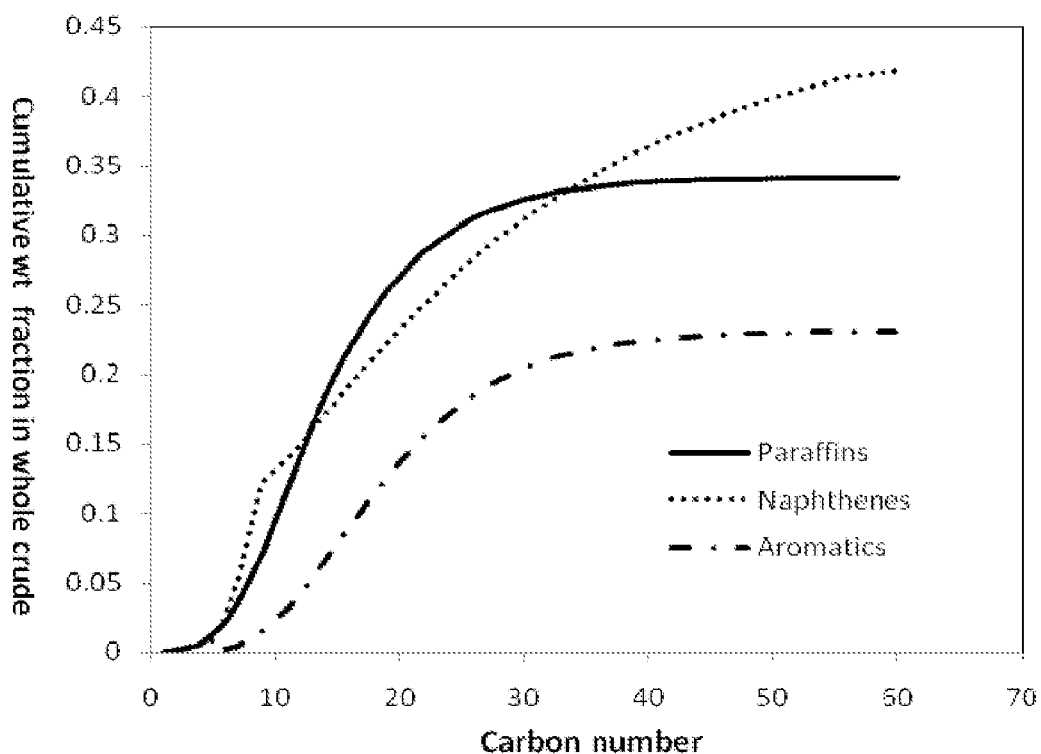
FIG. 31 is an illustration of model results for cumulative weight fractions of paraffins, naphthenes, and aromatics in whole crude versus carbon number for the crude oil Azeri BTC 2009 01.
Figure 32:
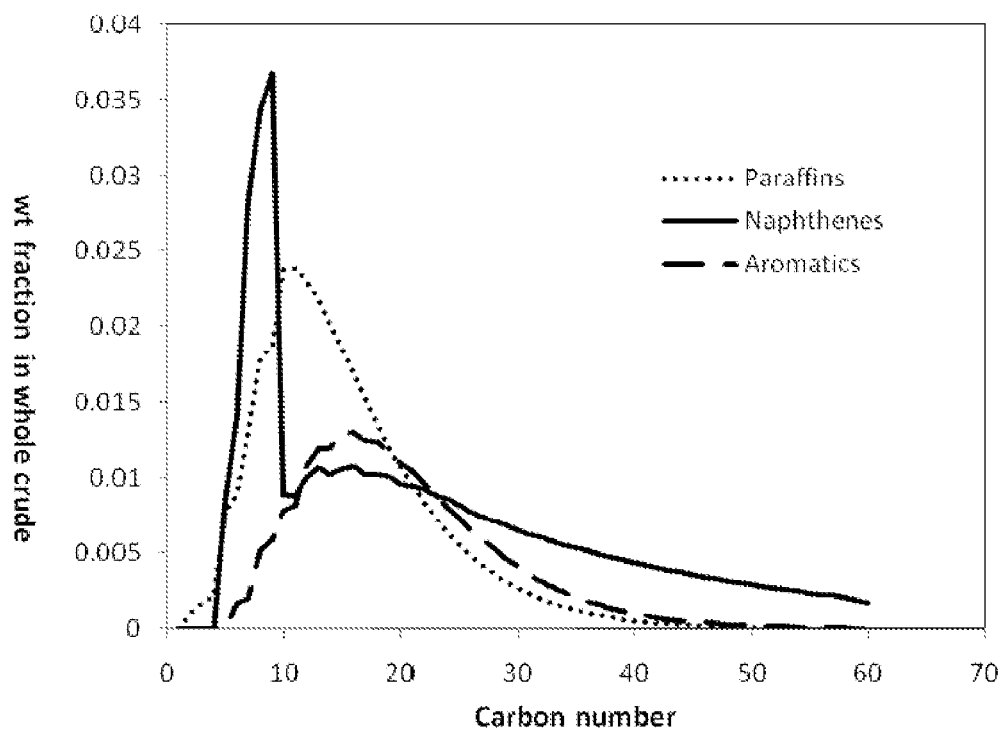
FIG. 32 is an illustration of model results for differential weight fractions of paraffins, naphthenes, and aromatics in whole crude versus carbon number for the crude oil Azeri BTC 2009 01.
Figure 33:
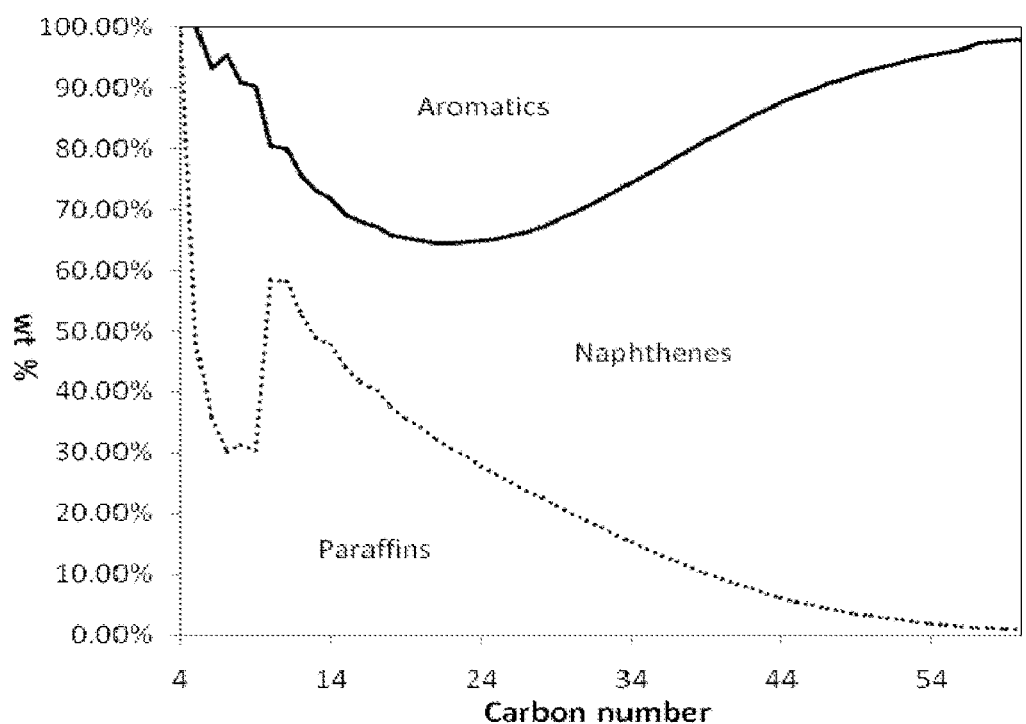
FIG. 33 is an illustration of model results for normalized weight percentage distributions of paraffins, naphthenes, and aromatics in whole crude versus carbon number for the crude oil.
Figure 34:
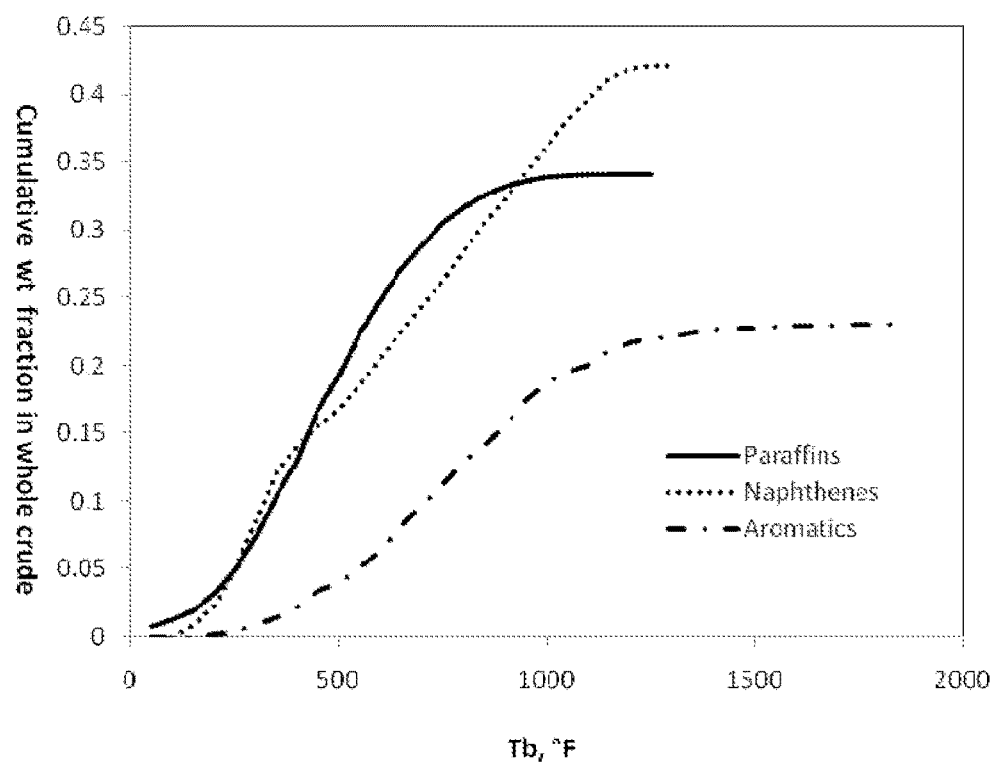
FIG. 34 is an illustration of model results for cumulative weight fractions of paraffins, naphthenes, and aromatics in whole crude versus true boiling point for the crude oil Azeri BTC 2009 01.
Figure 35:
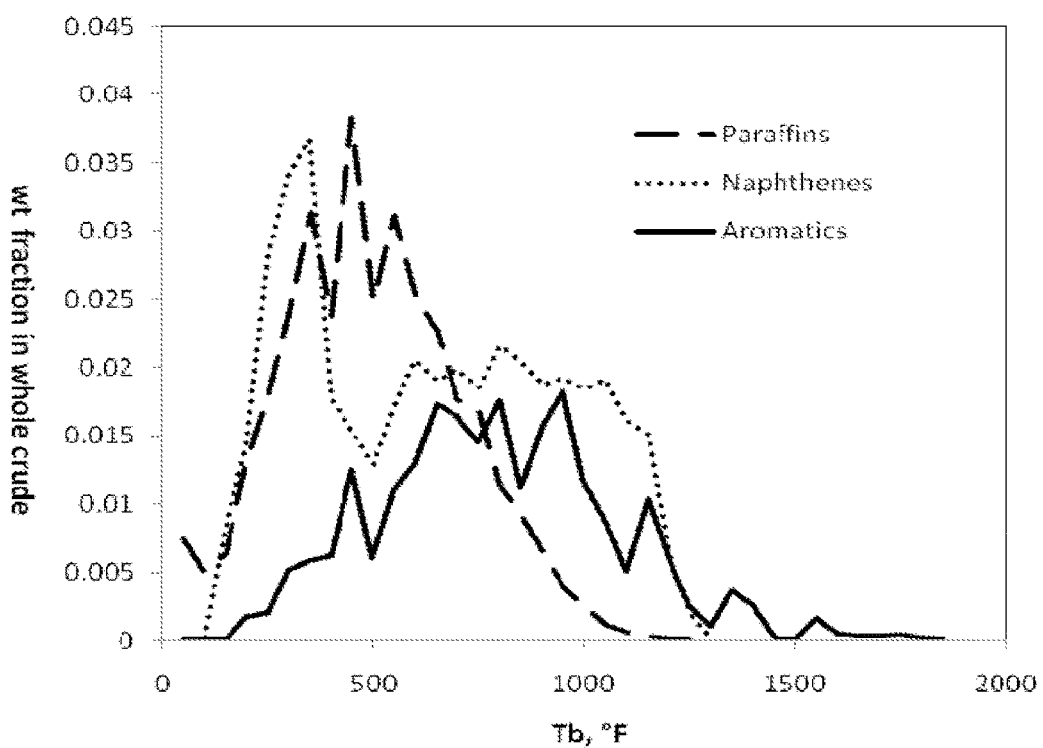
FIG. 35 is an illustration of model results for differential weight fractions of paraffins, naphthenes, and aromatics in whole crude versus true boiling point for the crude oil Azeri BTC 2009 01.
Figure 36:
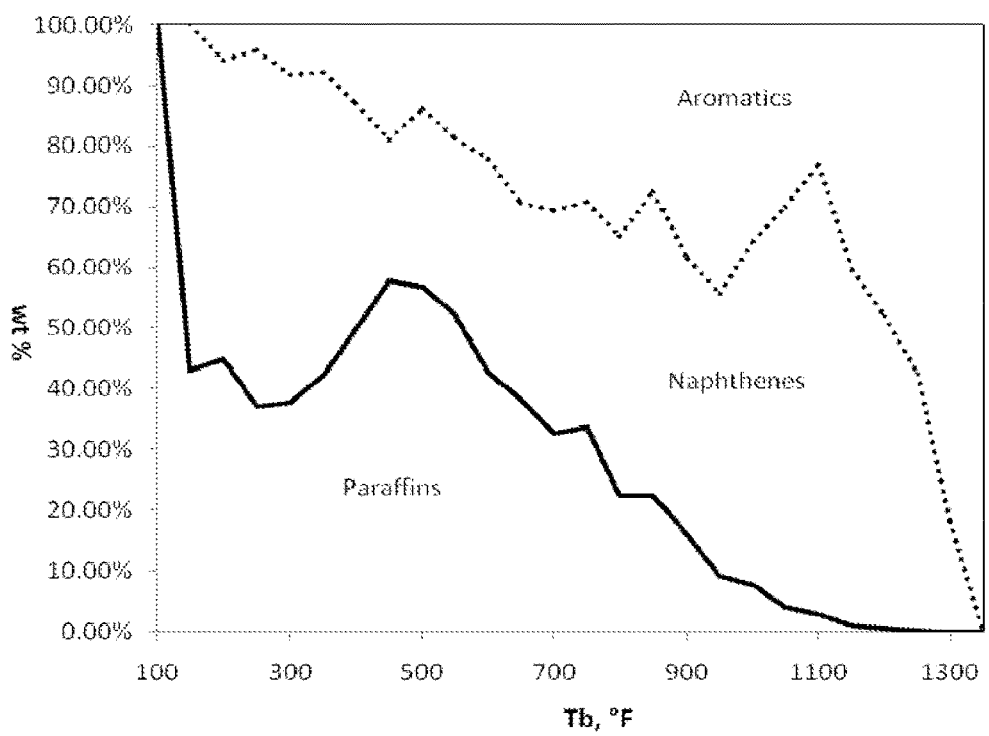
FIG. 36 is an illustration of model results for normalized weight percentage distributions of paraffins, naphthenes, and aromatics in whole crude versus true boiling point for the crude oil.
Figure 37:
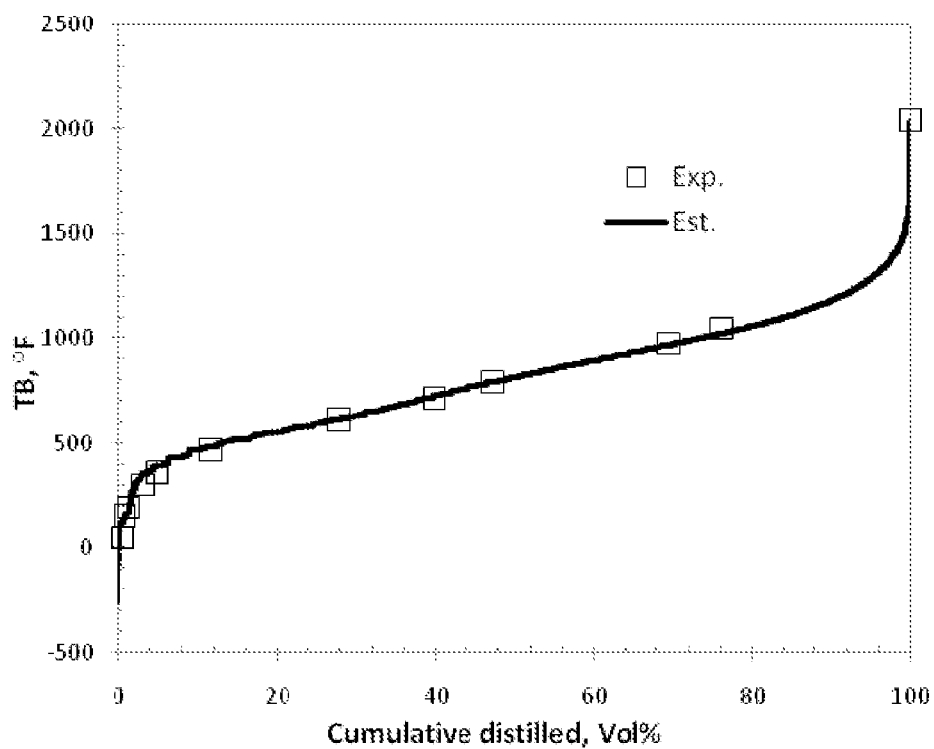
FIG. 37 is an illustration of model results for true boiling points for the crude oil Grane 2003 11.
Figure 38:
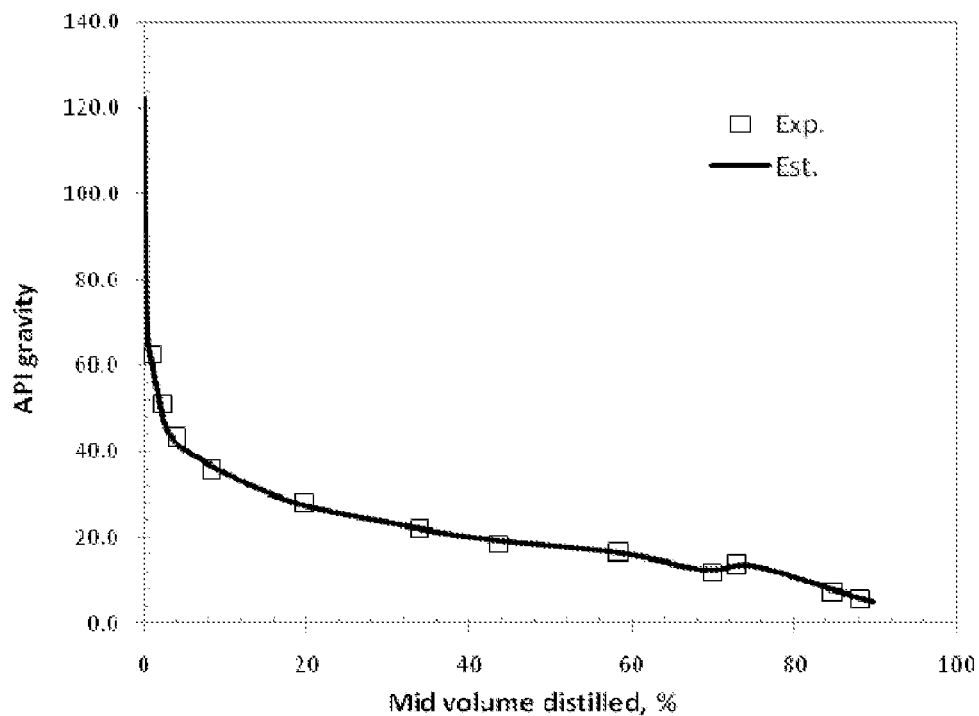
FIG. 38 is an illustration of model results for API gravities for the crude oil Grane 2003 11.
Figure 39:
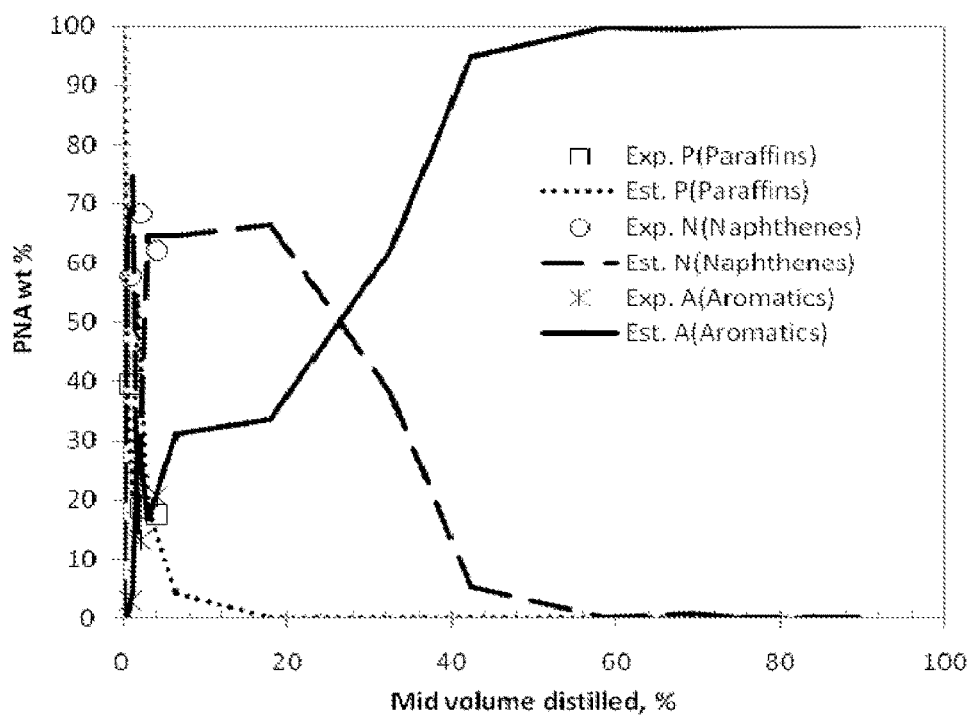
FIG. 39 is an illustration of model results for normalized PNA distributions for the crude oil Grane 2003 11.
Figure 40:
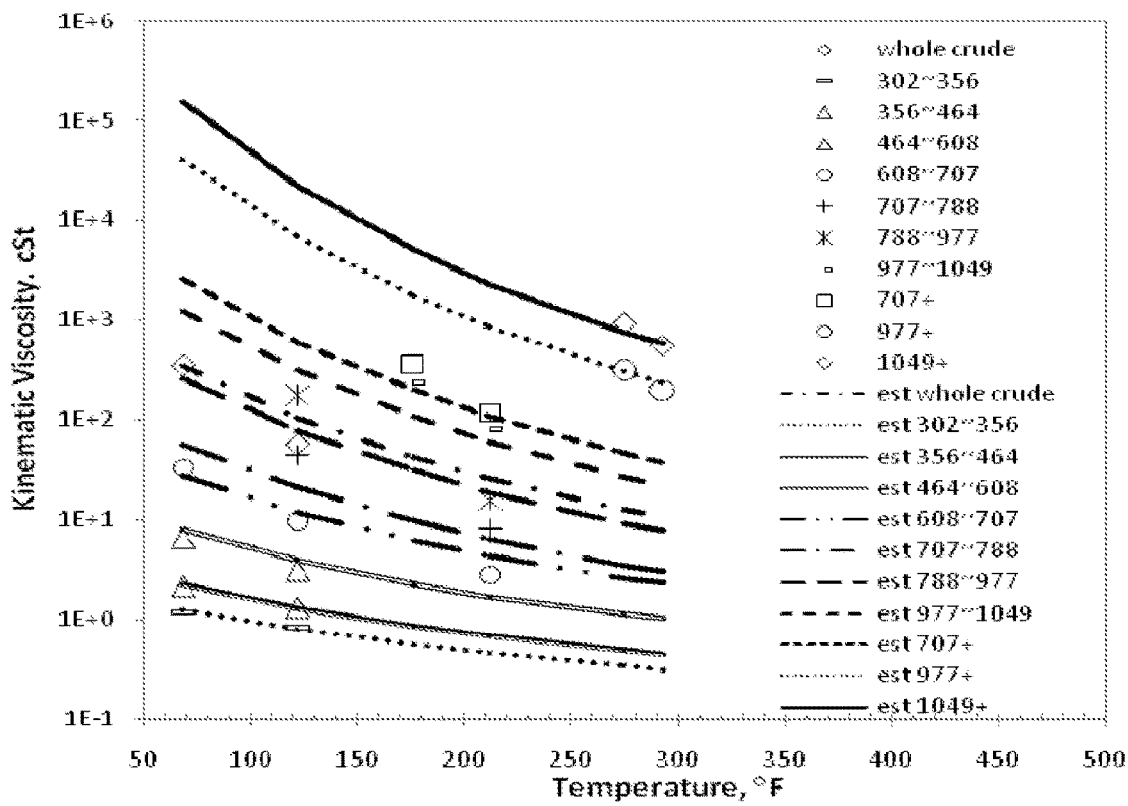
FIG. 40 is an illustration of model results for viscosities for the crude oil Grane 2003 11.
Figure 41:
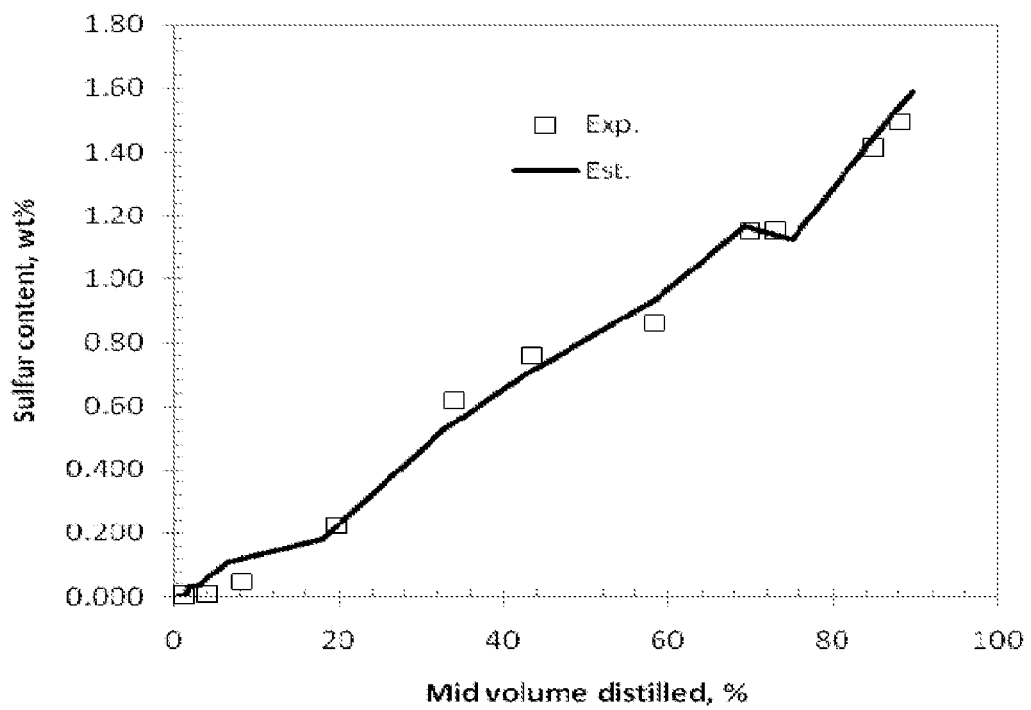
FIG. 41 is an illustration of model results for sulfur content for the crude oil Grane 2003 11.
Figure 42:
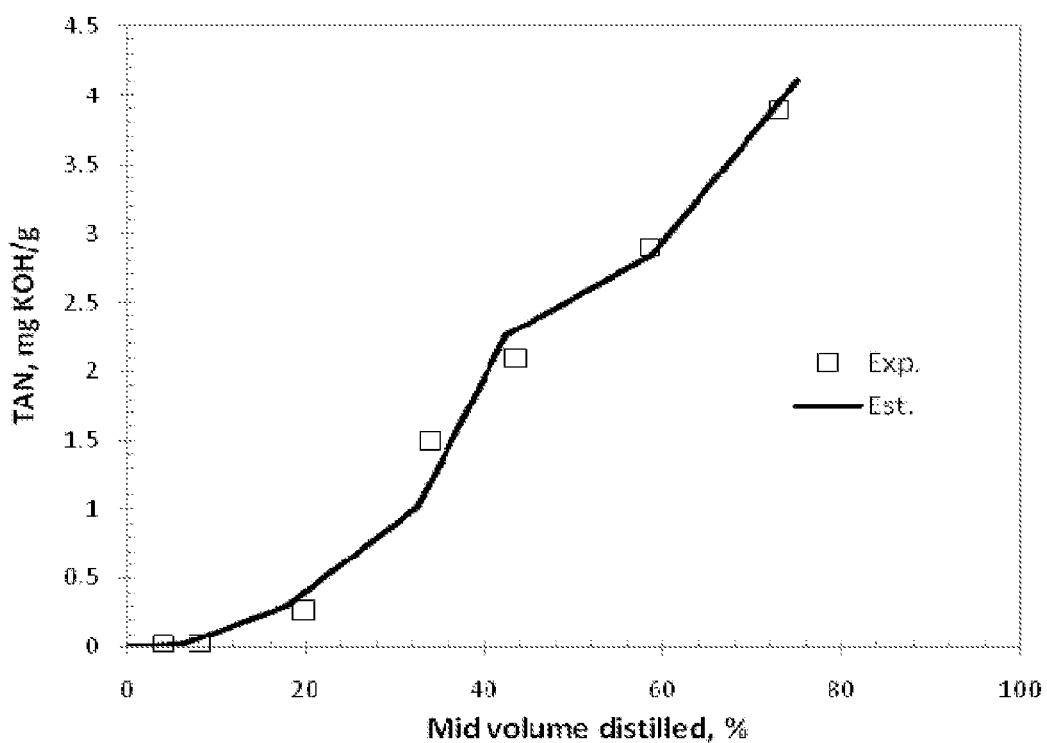
FIG. 42 is an illustration of model results for total acid number for the crude oil Grane 2003 11.

As illustrations, FIG. 31 shows cumulative weight fractions of paraffins, naphthenes, and aromatics in whole crude versus carbon number. FIG. 32 shows differential weight fractions of paraffins, naphthenes, and aromatics in whole crude versus carbon number. FIG. 33 shows normalized weight percentage distributions of paraffins, naphthenes, and aromatics in whole crude versus carbon number. FIG. 34 shows cumulative weight fractions of paraffins, naphthenes, and aromatics in the whole crude versus true boiling point. FIG. 35 shows differential weight fractions of paraffins, naphthenes, and aromatics in whole crude versus true boiling point. FIG. 36 shows normalized weight percentage distributions of paraffins, naphthenes, and aromatics in whole crude versus true boiling point.

2. Heavy Crude Oil—Grane 2003 11

2.1 General Information

Grane 2003 11 is the assay, available from Statoil, for a heavy crude oil from the North Sea. The reported assay data includes Distillation Yield, Density, UOPK, Total Sulfur, Mercaptan Sulfur, Total Nitrogen, Basic Nitrogen, Total Acid Number, Viscosity, PNA distributions, Vapor Pressure, Pour Point, Cloud Point, Freeze Point, Smoke Point, Cetane Index, Aniline Point, Wax Content, Hydrogen Content, Asphaltene Content, Refractive Index, and Conradson Carbon Residue.

In this example, assay data for Distillation Yield, Density, Viscosity, PNA distributions, Asphaltene Content, Total Sulfur, and Total Acid Number are regressed to identify the optimal molecular distribution parameters and the chemical compositions of hydrocarbon constituent molecules designed to best correlate available crude oil characterization data and to predict missing data.

Table 4 shows a set of bulk properties for this crude oil.

TABLE 4

Bulk properties for Grane 2003 11

| API Gravity | Sulfur, wt % | TAN., mg KOH/g | Kin. Vis, cSt @ 20° C. | Kin. Vis, cSt @ 50° C. |
|---|---|---|---|---|
| 18.7 | 0.83 | 2.2 | 354 | 57.5 |

2.2 Experimental Data Used in Regression

The available experimental data from the Statoil assay for the whole crude, gas, and boiling point cuts 1-13 selected for regression are shown in Table 5.

TABLE 5

Experimental data used in regression for Grane 2003 11

| Cuts | Whole crude | Gas | Cut 1 | Cut 2 | Cut 3 | Cut 4 | Cut 5 | Cut 6 | Cut 7 | Cut 8 | Cut 9 | Cut 10 | Cut 11 | Cut 12 | Cut 13 |
|---|---|---|---|---|---|---|---|---|---|---|---|---|---|---|---|
| IBP (° F.) | | C1 | 48 | 149 | 194 | 302 | 356 | 464 | 608 | 707 | 788 | 977 | 707 | 977 | 1049 |
| FBP (° F.) | | 48 | 149 | 194 | 302 | 356 | 464 | 608 | 707 | 788 | 977 | 1049 | FBP | FBP | FBP |
| Yield, vol % | | 0.64 | 0.11 | 0.57 | 1.92 | 1.64 | 6.85 | 16.27 | 11.76 | 7.61 | 22.29 | 6.66 | 60.24 | 30.34 | 23.68 |
| Gravity (API) | 18.7 | | | 62.7 | 51.1 | 43.1 | 35.6 | 28.2 | 22.2 | 18.6 | 16.5 | 13.4 | 12.0 | 7.4 | 5.7 |
| Paraffins, | | | | 39.3 | 18.5 | 17.4 | | | | | | | | | |
| Naphthenes, wt % | | | | 57.7 | 68.4 | 62.0 | | | | | | | | | |
| Aromatics, wt % | | | | 2.9 | 13.1 | 20.6 | | | | | | | | | |
| Sulfur, wt % | 0.826 | | | 0.002 | | 0.010 | 0.044 | 0.225 | 0.620 | 0.761 | 0.859 | 1.149 | 1.151 | 1.410 | 1.496 |
| Kin. Vis, cSt @ 20° C. | 354.1 | | | | | 1.2 | 2.2 | 6.6 | 33.5 | | | | | | |
| Kin, Vis, cSt @ 50° C. | 57.5 | | | | | 0.8 | 1.3 | 3.0 | 9.5 | 44.8 | 173.1 | | | | |
| Kin. Vis, cSt @ 80° C. | | | | | | | | | | | | 231.5 | 351.8 | | |
| Kin. Vis, cSt @ 100° C. | | | | | | | | 2.8 | 8.2 | 15.9 | 78.9 | 117.6 | | | |
| Kin. Vis, cSt @ 135° C. | | | | | | | | | | | | | | 306.6 | 932.2 |
| Kin. Vis, cSt @ 145° C. | | | | | | | | | | | | | | 198.1 | 560.8 |
| Asphaltene, wt % | | | | | | | | | | | | | 1.6 | 3.9 | 5.2 |
| TAN., mg KOH/g | 2.2 | | | | | 0.03 | 0.03 | 0.26 | 1.5 | 2.1 | 2.9 | 3.9 | 2.4 | | |

2.3 Molecular Characterization Results
2.3.1 Optimized Values

The optimized values for the molecular distribution parameters for crude oil Grane 2003 11 are shown in Table 6. Note that, during regression, values of probability distribution parameters for sulfides, mercaptans, and paraffinic acids are set to be same as those for paraffin molecules. Also, values for naphthenic sulfides and naphthenic acids distribution parameters are set to be same as those for naphthene molecules.

TABLE 6

Optimized values for the molecular distribution parameters for Grane 2003 11

| Molecule Classes | wt % | Segments | Distribution Function | Scale | Shape |
|---|---|---|---|---|---|
| Paraffins | 1.13 | —CH$_2$— | Gamma | 0.031 | 81.144 |
| | | ![Y-shape] | Uniform | N/A | N/A |
| | | ![Y-shape] | Uniform | N/A | N/A |

TABLE 6-continued

Optimized values for the molecular distribution parameters for Grane 2003 11

| Molecule Classes | wt % | Segments | Distribution Function | Scale | Shape |
|---|---|---|---|---|---|
| Naphthenes | 20.50 |  | Gamma | 0.302 | 6.156 |
|  |  | —CH$_2$—[a] | Gamma | 0.458 | 12.931 |
|  |  | —CH$_2$—[b] | Gamma | 0.370 | 1 |
|  |  | —CH$_3$ | Uniform | N/A | N/A |
|  |  | N6/(N5 + N6)[c] | Alternative | 0.643 |  |
| Aromatics | 72.53 |  | Gamma | 1.144 | 1.160 |
|  |  |  | Gamma | 1.00 | 1.977 |
|  |  | —CH$_2$— | Gamma | 5.035 | 2.460 |
|  |  | —CH$_3$ | Uniform | N/A | N/A |
| Sulfides | 0 | —CH$_2$— | Gamma | Set the same value as paraffins | |
| Mercaptans | 0 | —CH$_2$— | Gamma | Set the same value as paraffins | |
| Naphthenic sulfides | 0 |  | Gamma | Set the same value as naphthenes | |
|  |  | —CH$_2$—[a] | Gamma | Set the same value as naphthenes | |
|  |  | —CH$_2$—[b] | Gamma | Set the same value as naphthenes | |
|  |  | —CH$_3$ | Uniform | N/A | N/A |
|  |  | N6/(N5 + N6)[c] | Alternative | Set the same value as naphthenes | |
| Thiophenes | 4.2673 |  | Gamma | 0.631 | 3.929 |
|  |  | —CH$_2$— | Gamma | 3.495 | 4.465 |
|  |  | —CH$_3$ | Uniform | N/A | N/A |
| Paraffinic acids | 0 | —CH$_2$— | Gamma | Set the same value as paraffins | |
| Naphthenic acids | 0 |  | Gamma | Set the same value as naphthenes | |
|  |  | Side chain carbon no. | Gamma | Seth the same value as —CH$_2$—[a] of naphthenes | |
| Aromatic acids | 1.5731 |  | Gamma | 0.01 | 0.01 |
|  |  |  | Gamma | 1.853 | 0.395 |

TABLE 6-continued

Optimized values for the molecular distribution parameters for Grane 2003 11

| Molecule Classes | wt % | Segments | Distribution Function | Scale | Shape |
|---|---|---|---|---|---|
| | | Side chain carbon no. | Gamma | 4.572 | 5.550 |
| Viscosity parameters | $k_0$ | −1.463 | | | |
| | $k_1$ | 4.822 | | | |
| | $k_2$ | 934.043 | | | |
| | $k_3$ | 27.531 | | | |

Notes:
(a) The —$CH_2$— segment in the side chains on cyclohexane-based naphthenic molecules.
(b) The —$CH_2$— segment in the side chains on cyclopentane-based naphthenic molecules.
(c) N6/(N5 + N6) is the mole ratio of cyclohexane-based naphthenic molecules over all the naphthenic molecules.

Properties Plots

Calculated with the optimized molecular distribution parameters summarized in Table 6, FIGS. 37-42 show the model-predicted true boiling point curve, API gravity curve, PNA distributions curves, viscosity curves for whole crude and its fractions, sulfur content curve, and total acid number curve, respectively, for the crude oil Grane 2003 11.

Molecule Distribution Plots

The optimized molecular distribution parameters further provide a basis to determine the chemical compositions of the crude oil in terms of the model hydrocarbon constituent molecules.

Figure 43:
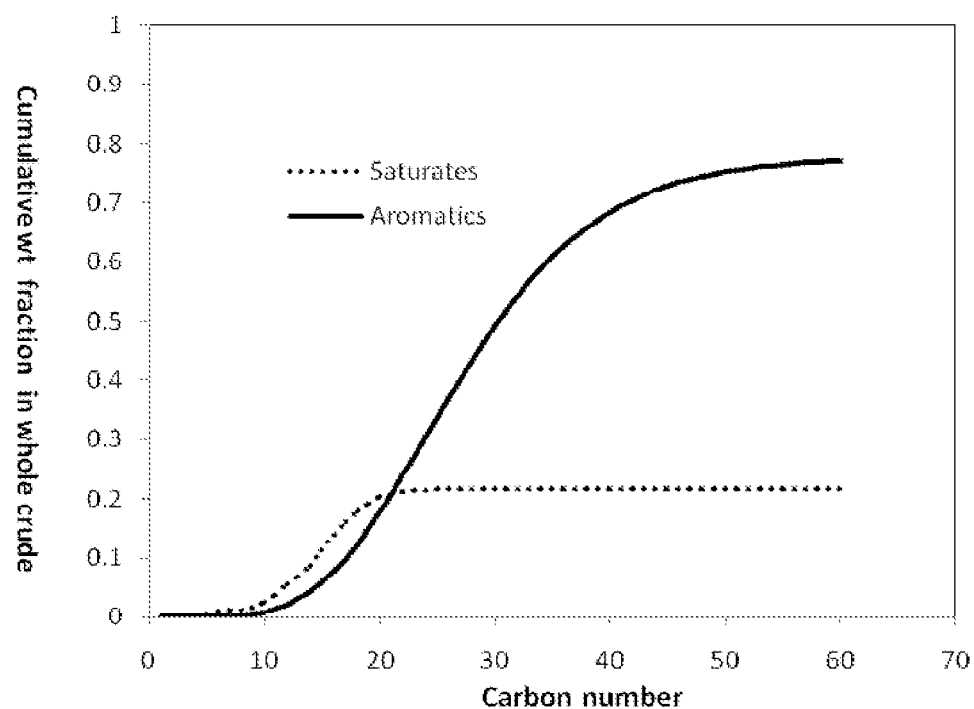
FIG. 43 is an illustration of model results for cumulative weight fractions of saturates and aromatics in the whole crude versus carbon number for the crude oil Grane 2003 11.
Figure 44:
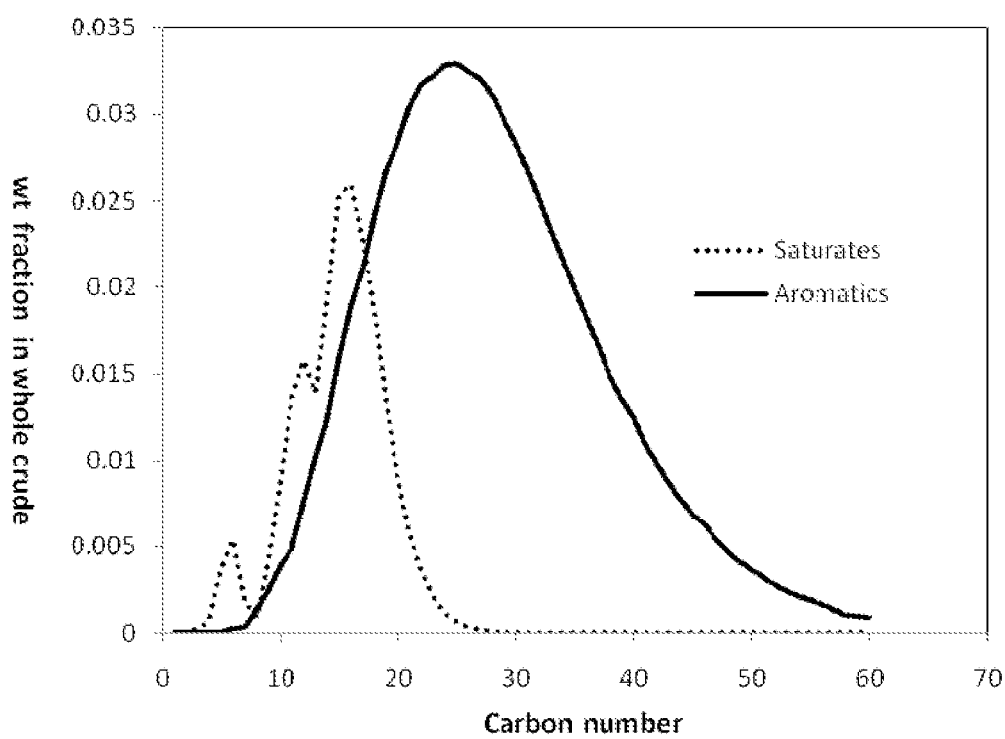
FIG. 44 is an illustration of model results for differential weight fractions of saturates and aromatics in the whole crude versus carbon number for the crude oil Grane 2003 11.
Figure 45:
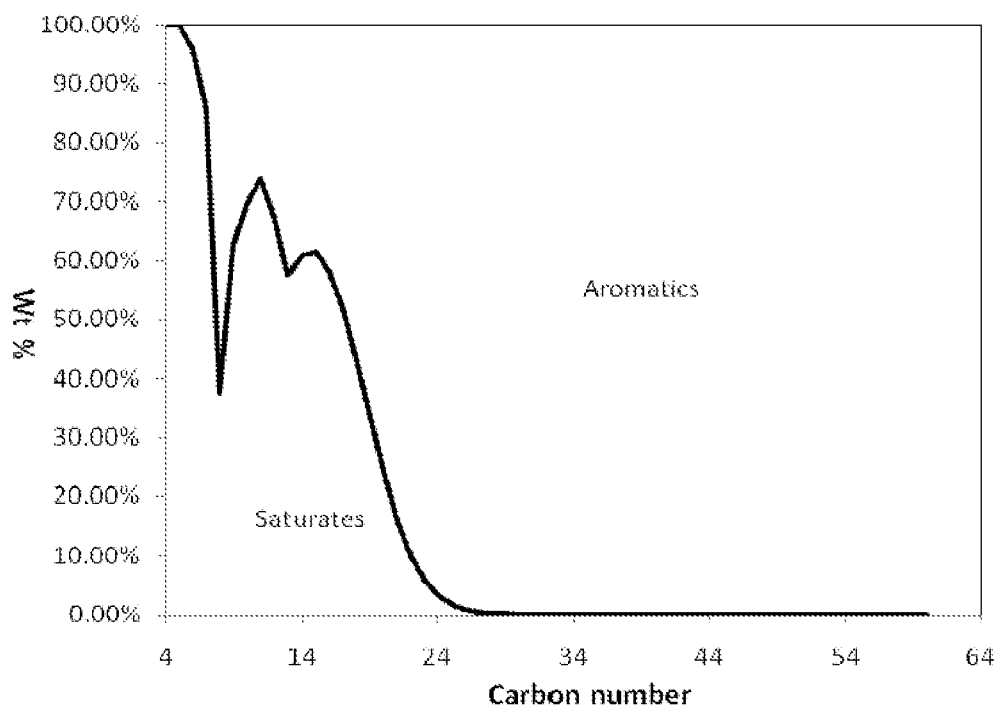
FIG. 45 is an illustration of model results for normalized weight percentage distributions of saturates and aromatics in the whole crude versus carbon number for the crude oil Grane 2003 11.
Figure 46:
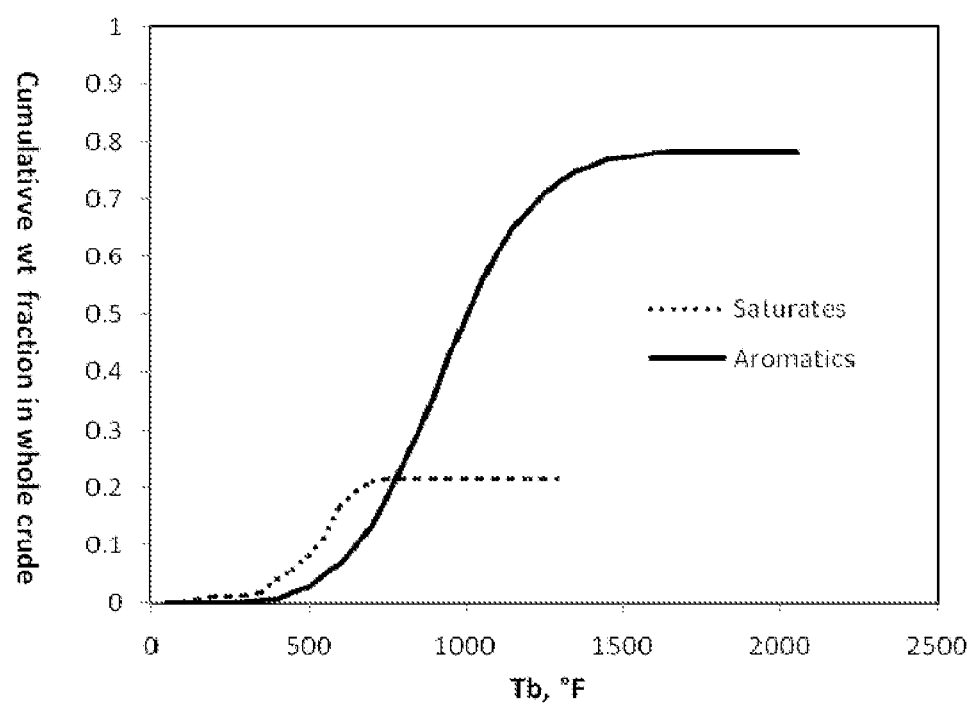
FIG. 46 is an illustration of model results for cumulative weight fractions of saturates and aromatics in the whole crude versus true boiling point for the crude oil Grane 2003 11.
Figure 47:
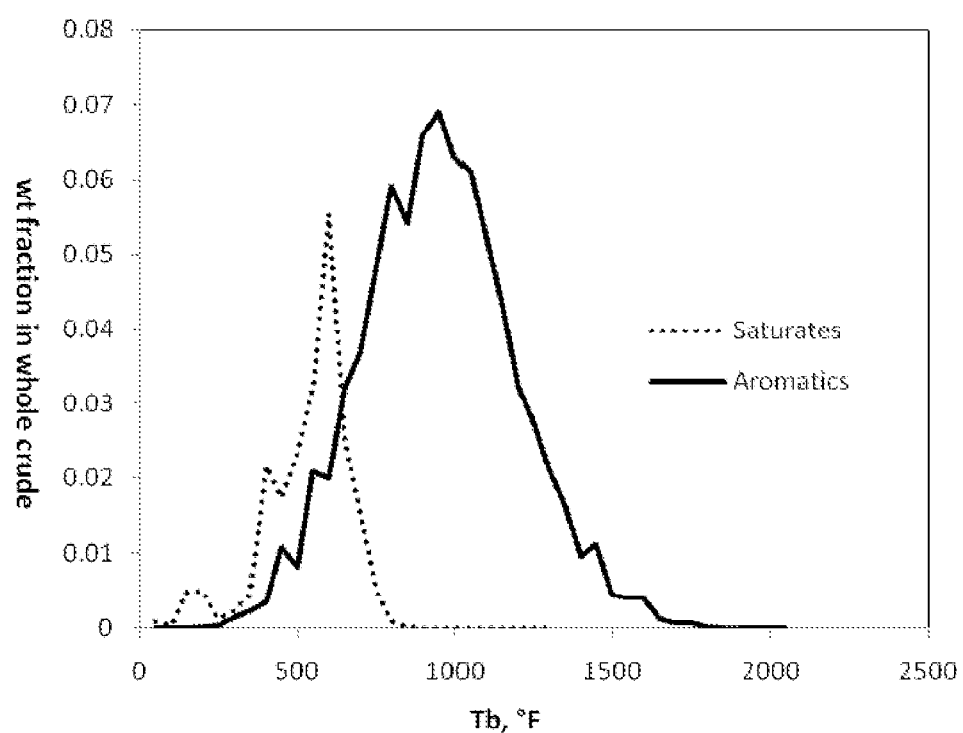
FIG. 47 is an illustration of model results for differential weight fractions of saturates and aromatics in the whole crude versus true boiling point for the crude oil Grane 2003 11.
Figure 48:
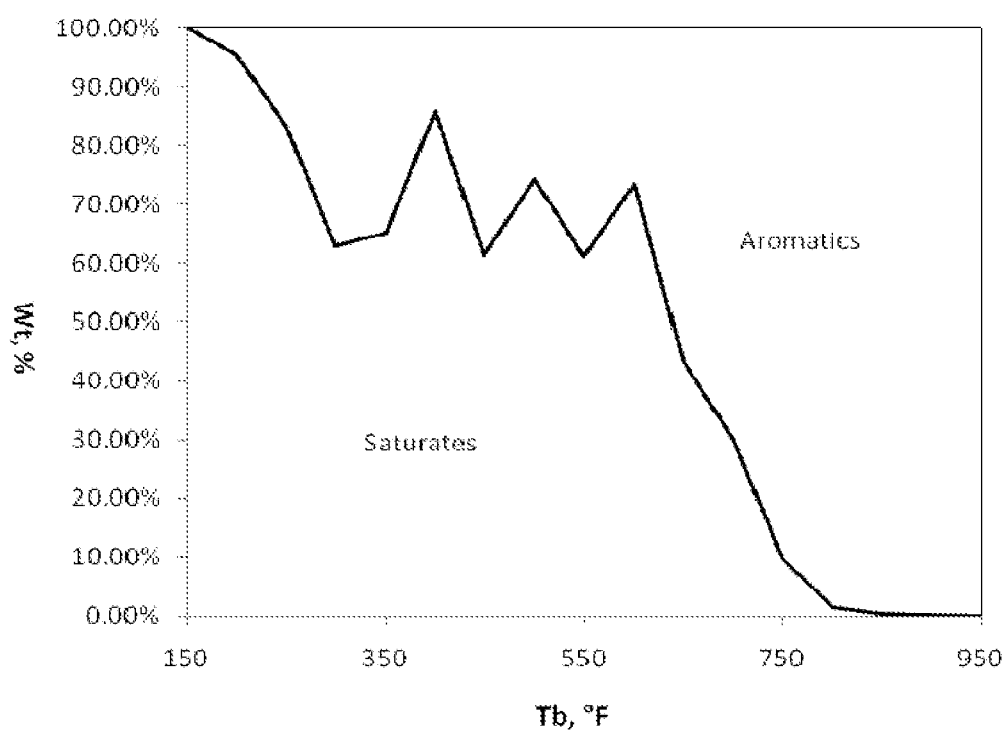
FIG. 48 is an illustration of model results for normalized weight percentage distributions of saturates and aromatics in the whole crude versus true boiling point for the crude oil Grane 2003 11.
Figure 49:
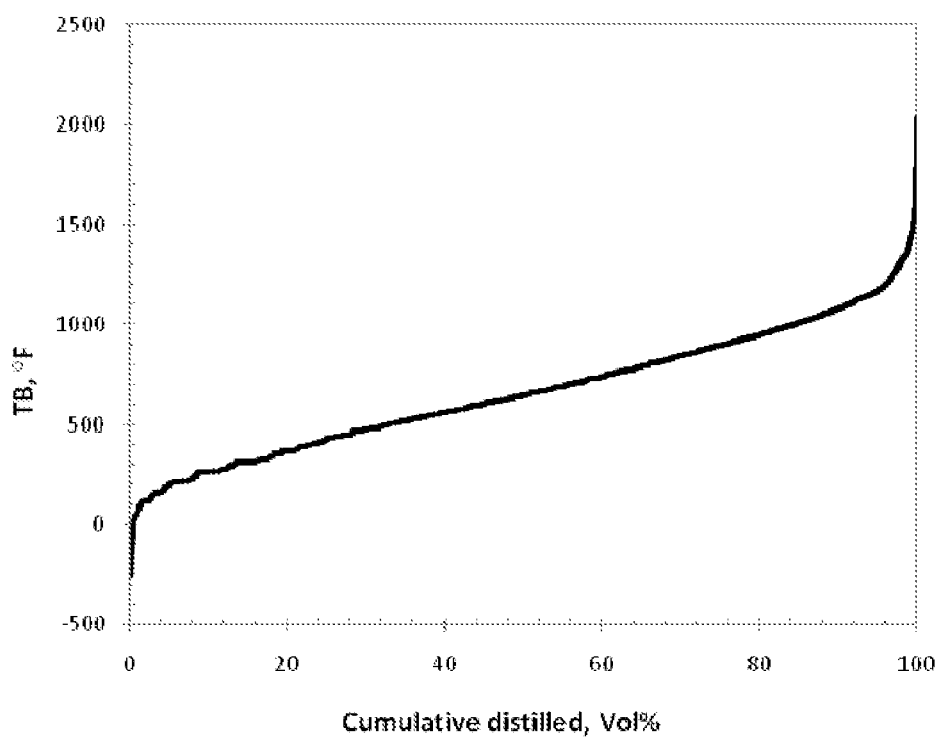
FIG. 49 is an illustration of model predictions for true boiling points for the blend crude.
Figure 50:
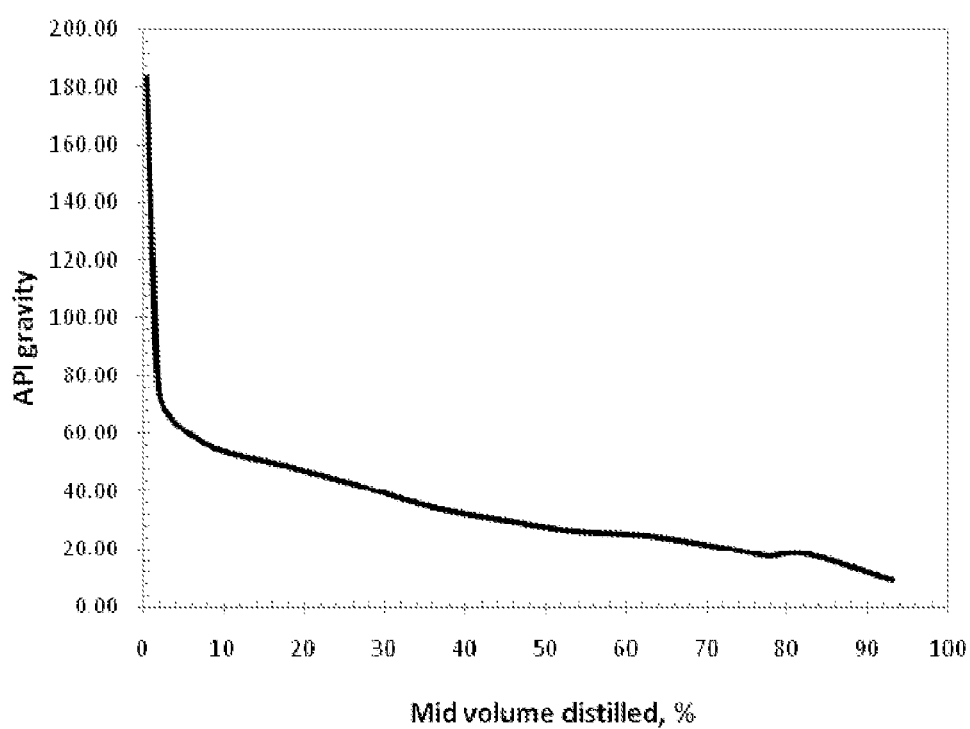
FIG. 50 is an illustration of model predictions for API gravities for the blend crude.
Figure 51:
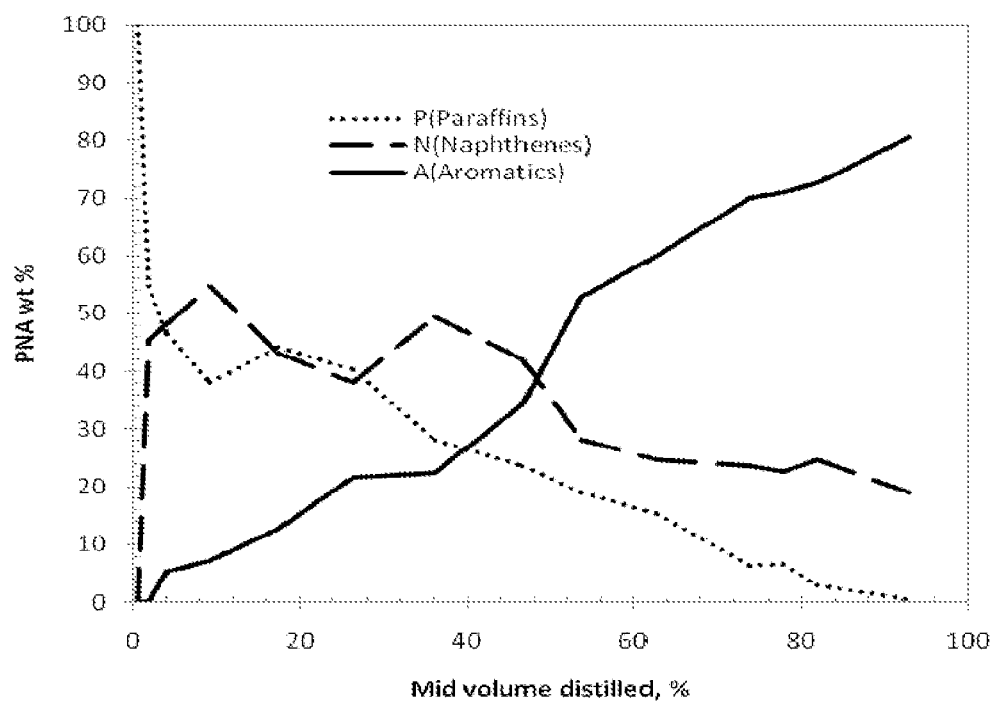
FIG. 51 is an illustration of model PNA distributions predictions for the blend crude.
Figure 52:
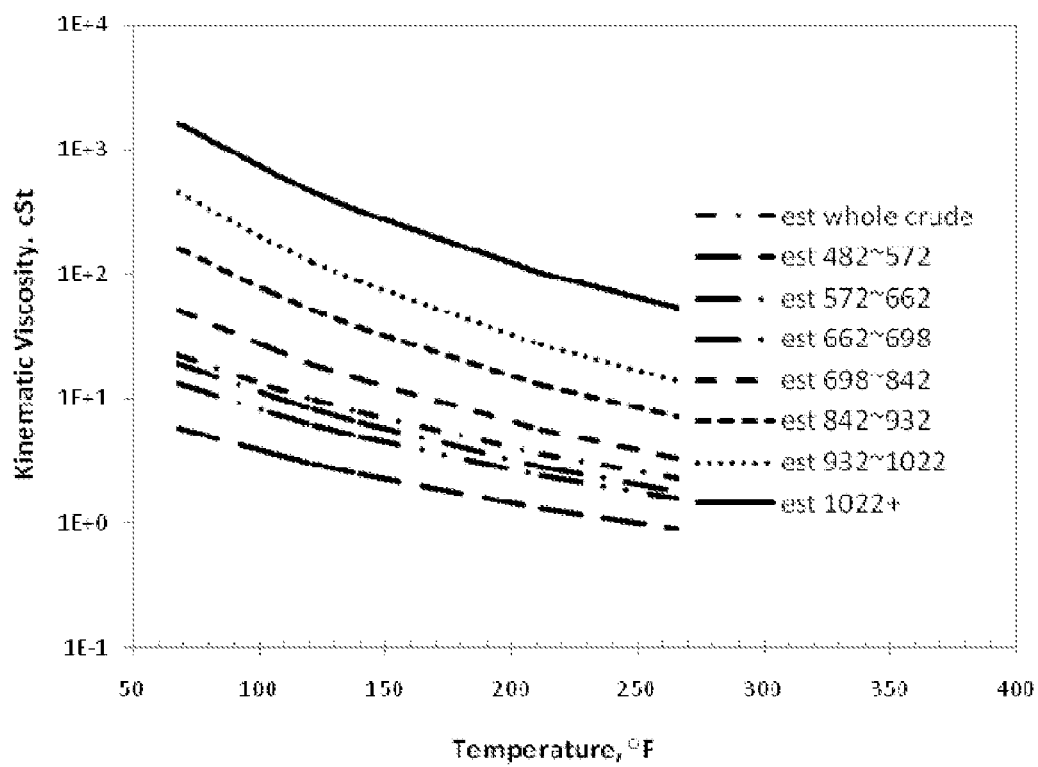
FIG. 52 is an illustration of model predictions for viscosities for the blend crude (Note that viscosity parameters are fixed at their default value with $k_0=-1$, $k_1=-10$, $k_2=500$, and $k_3=100$).
Figure 53:
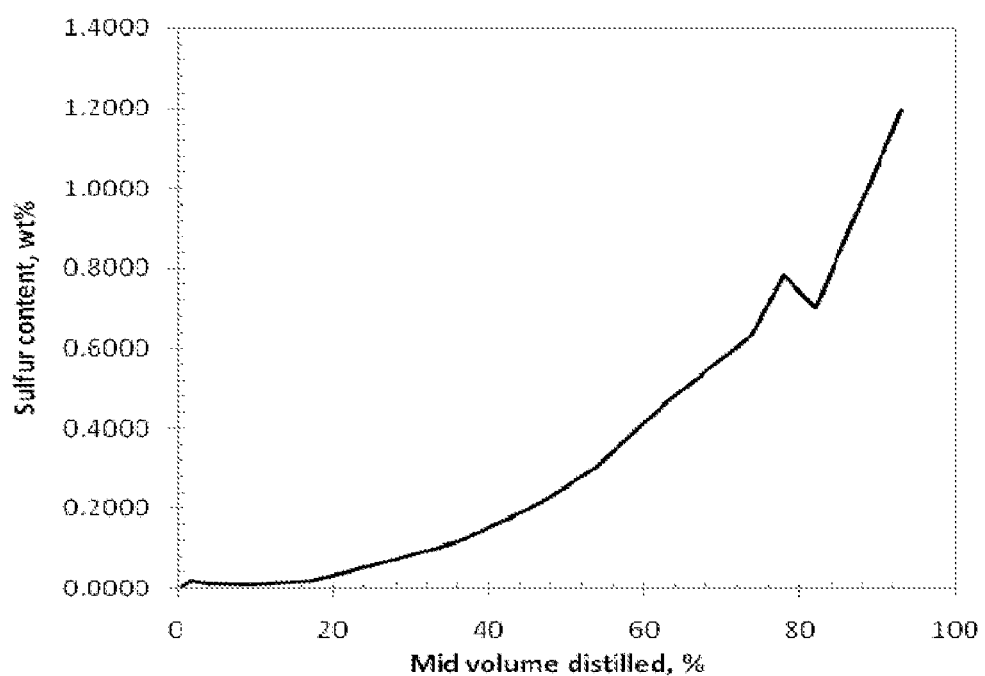
FIG. 53 is an illustration of model predictions for sulfur content for the blend crude.
Figure 54:
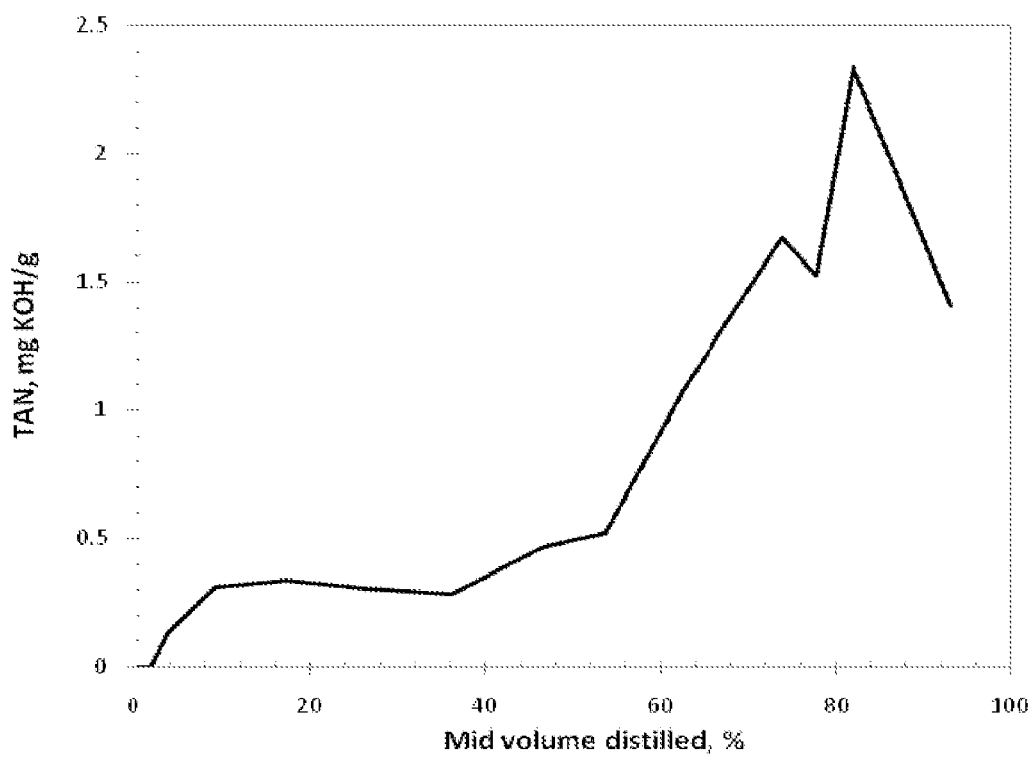
FIG. 54 is an illustration of model predictions for total acid number for the blend crude.
Figure 55:
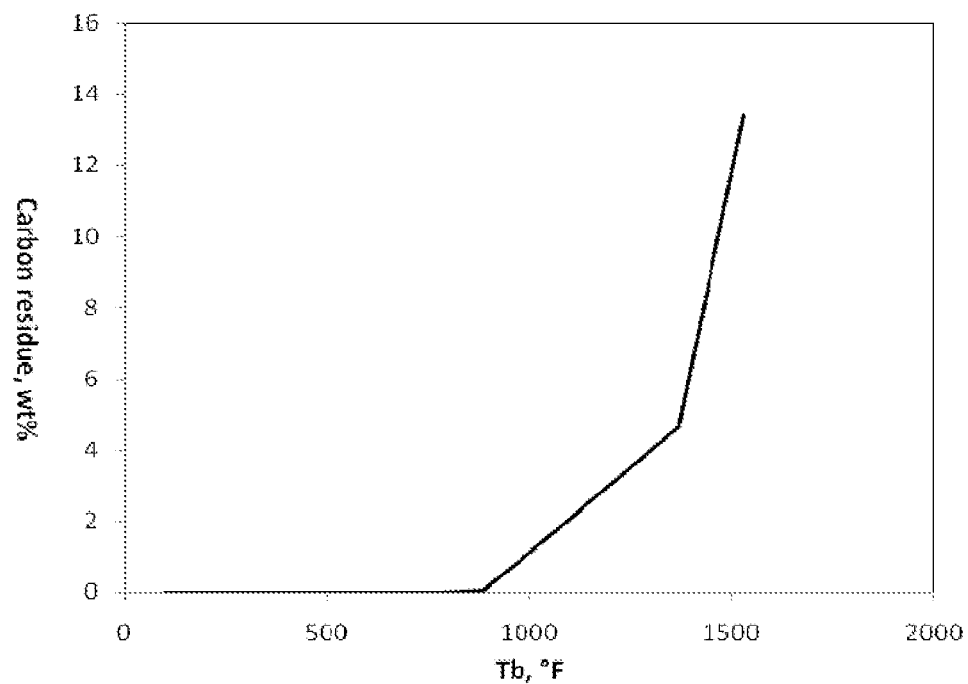
FIG. 55 is an illustration of model predictions for carbon residue for the blend crude.
Figure 56:
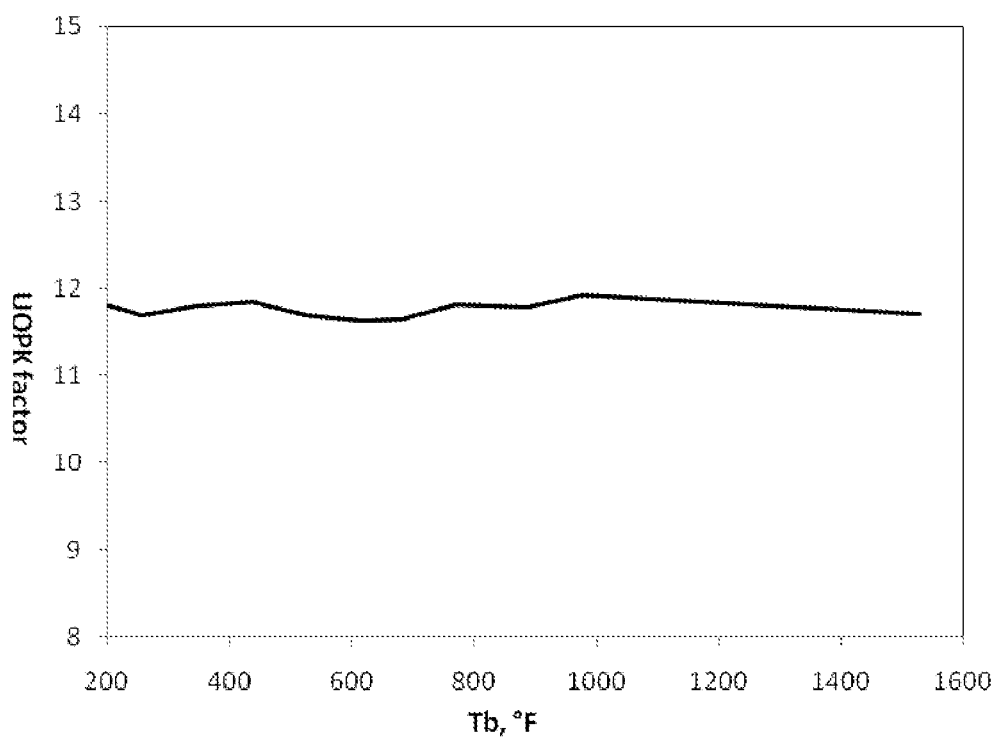
FIG. 56 is an illustration of model predictions for UOPK factor for the blend crude.
Figure 57:
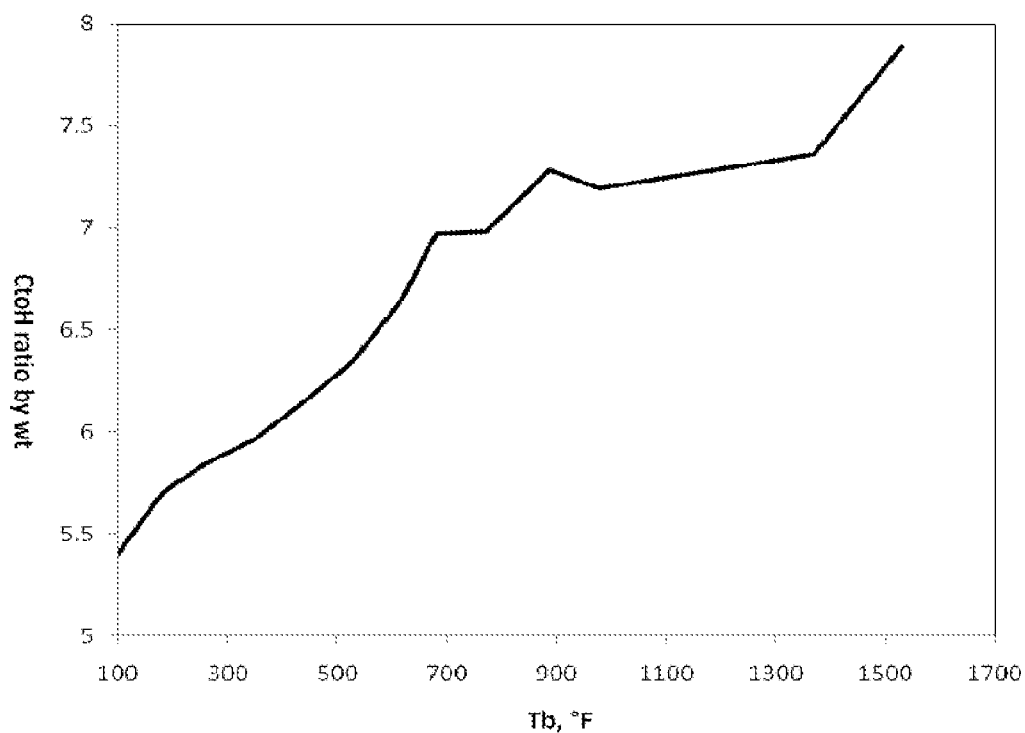
FIG. 57 is an illustration of model predictions for Carbon to Hydrogen ratio for the blend crude.

FIG. 43 shows the cumulative weight fractions of saturates and aromatics in the whole crude versus carbon number. Note that, for this heavy crude oil, paraffins content is very low. Therefore, paraffins and naphthenes are combined and shown together as saturates. FIG. 44 shows the differential weight fractions of saturates and aromatics in the whole crude versus carbon number. FIG. 45 shows the normalized weight percentage distributions of saturates and aromatics in whole crude versus carbon number. FIG. 46 shows the cumulative weight fractions of saturates and aromatics in the whole crude versus true boiling point. FIG. 47 shows the differential weight fractions of saturates and aromatics in whole crude versus true boiling point. FIG. 48 shows the normalized weight percentage distributions of saturates and aromatics in whole crude versus true boiling point.

3. Blend Crude Oil—60% Azeri BTC 2009 01 and 40% Grane 2003 11

3.1 General Information

The molecular distribution parameters for crude oils also provide the essential molecular basis for crude blending calculations. The chemical compositions of the blend crude are simply the arithmetic averages of the chemical compositions of the individual crude oils used in blending. The assay properties of the blend crude can then be computed based on the chemical compositions of the blend crude.

In this example, the blend crude contains 60% of light crude Azeri BTC 2009 01 and 40% of heavy crude Grane 2003 11.

3.2 Properties Plots

Based on the blending ratios of the two crude oils Azeri BTC 2009 01 and Grane 2003 11, the chemical compositions of the blend crude can be obtained and its properties can also be estimated.

FIGS. 49-57 show the model-predicted true boiling point curve, API gravity curve, PNA distributions curves, viscosity curves for whole crude and its fractions, sulfur content curve, total acid number curve, carbon residue curve, UOPK factor curve, and Carbon to Hydrogen ratio curve for the blend crude, respectively.

3.3 Molecule Distribution Plots

Figure 58:
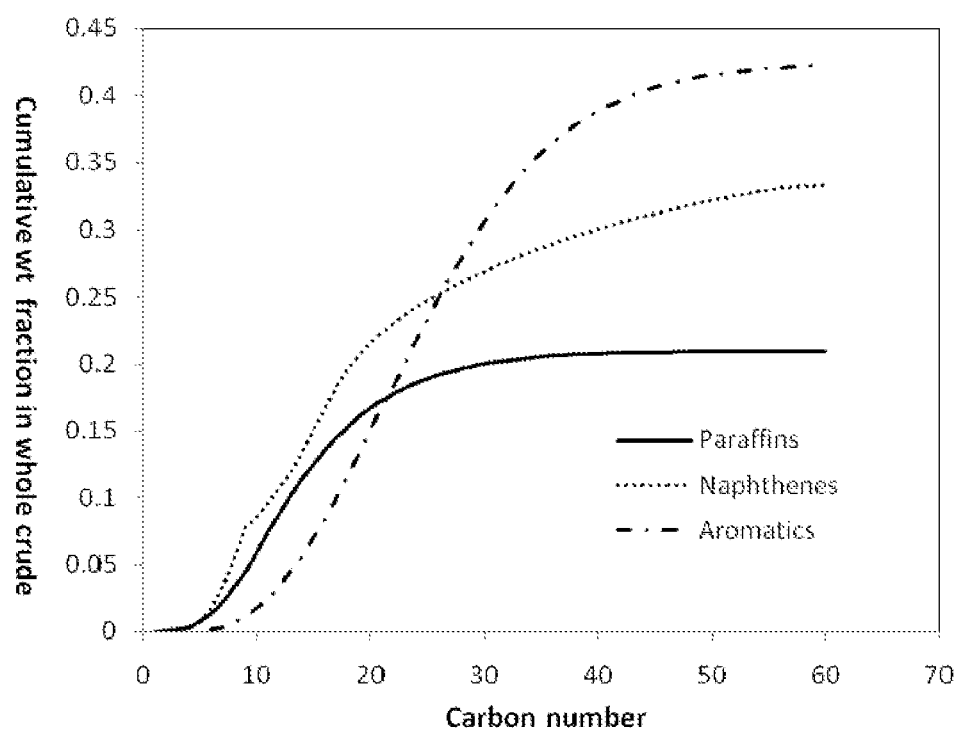
FIG. 58 is an illustration of model predictions for cumulative weight fractions of paraffins, naphthenes, and aromatics in whole crude versus carbon number for the blend crude.
Figure 59:
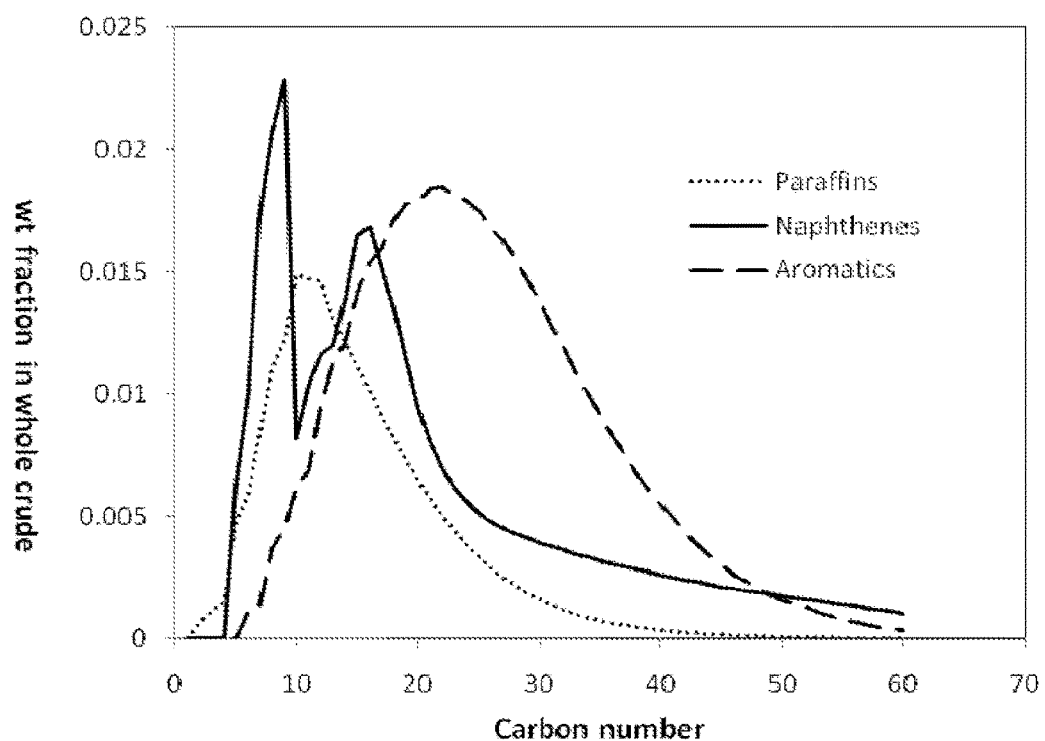
FIG. 59 is an illustration of model predictions for differential weight fractions of paraffins, naphthenes, and aromatics in whole crude versus carbon number for the blend crude.
Figure 60:
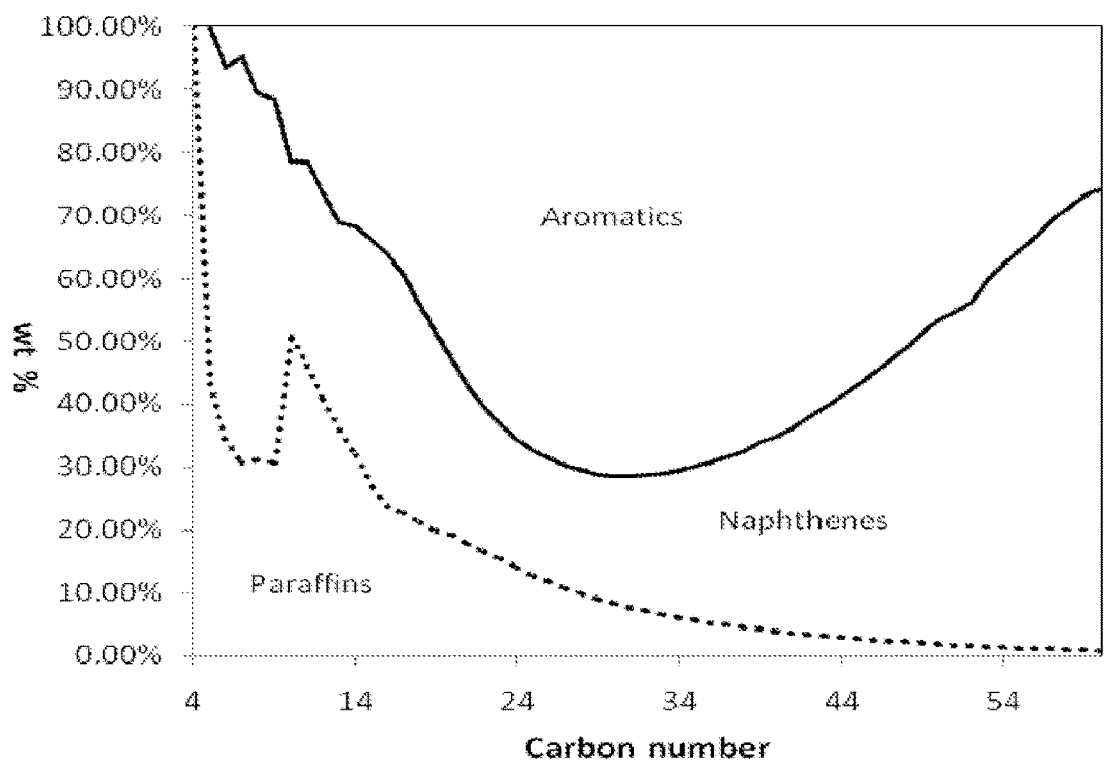
FIG. 60 is an illustration of model predictions for normalized weight percentage distributions of paraffins, naphthenes, and aromatics in whole crude versus carbon number for the blend crude.
Figure 61:
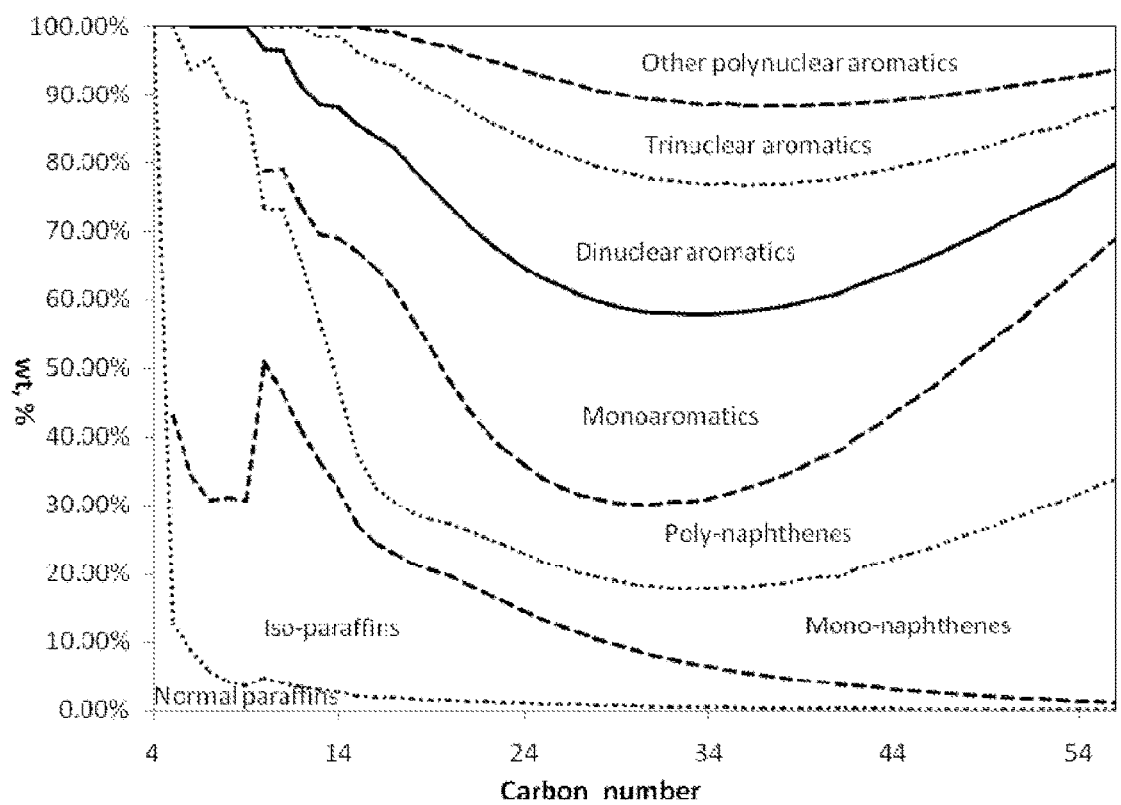
FIG. 61 is an illustration of model predictions for normalized weight percentage distributions of normal paraffins, iso-paraffins, mono-naphthenes, poly-naphthenes, monoaromatics, dinuclear aromatics, trinuclear aromatics, and other polynuclear aromatics in whole crude versus carbon number for the blend crude.
Figure 62:
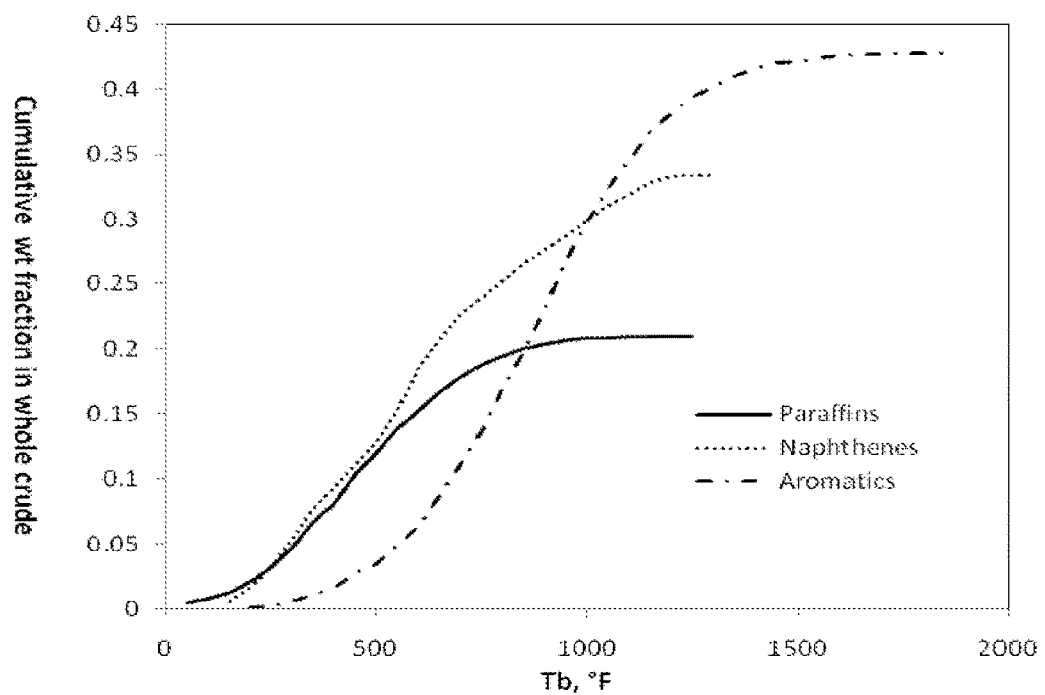
FIG. 62 is an illustration of model predictions for cumulative weight fractions of paraffins, naphthenes, and aromatics in whole crude versus true boiling point for the blend crude.
Figure 63:
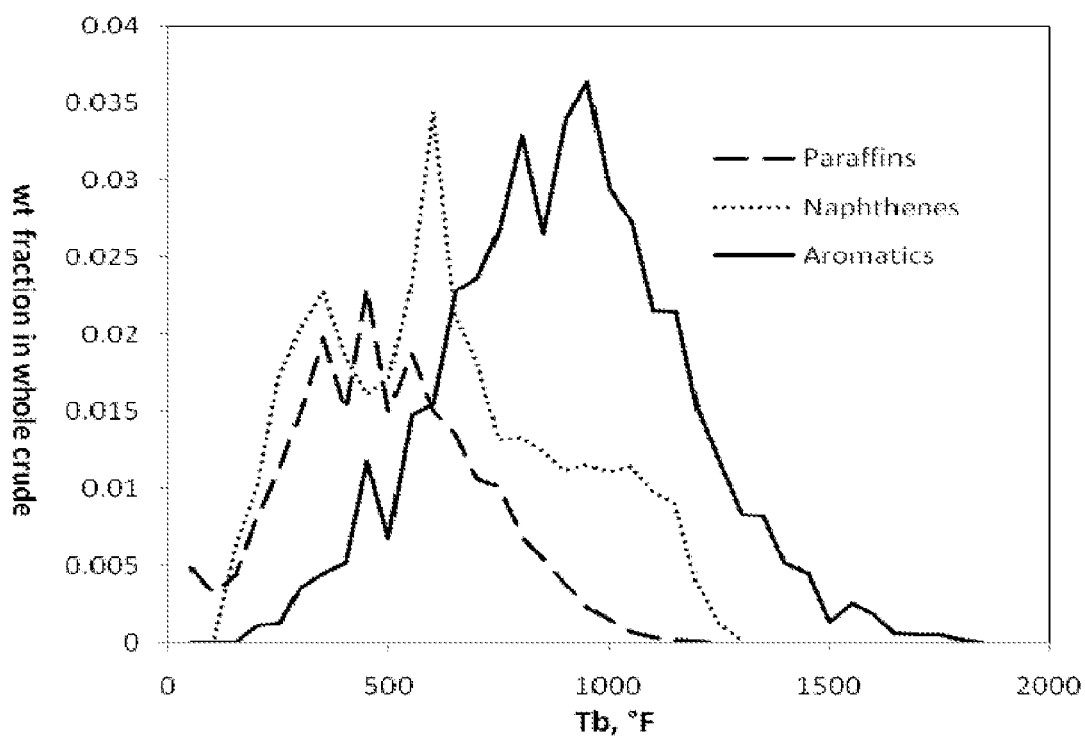
FIG. 63 is an illustration of model predictions for differential weight fractions of paraffins, naphthenes, and aromatics in whole crude versus true boiling point for the blend crude.
Figure 64:
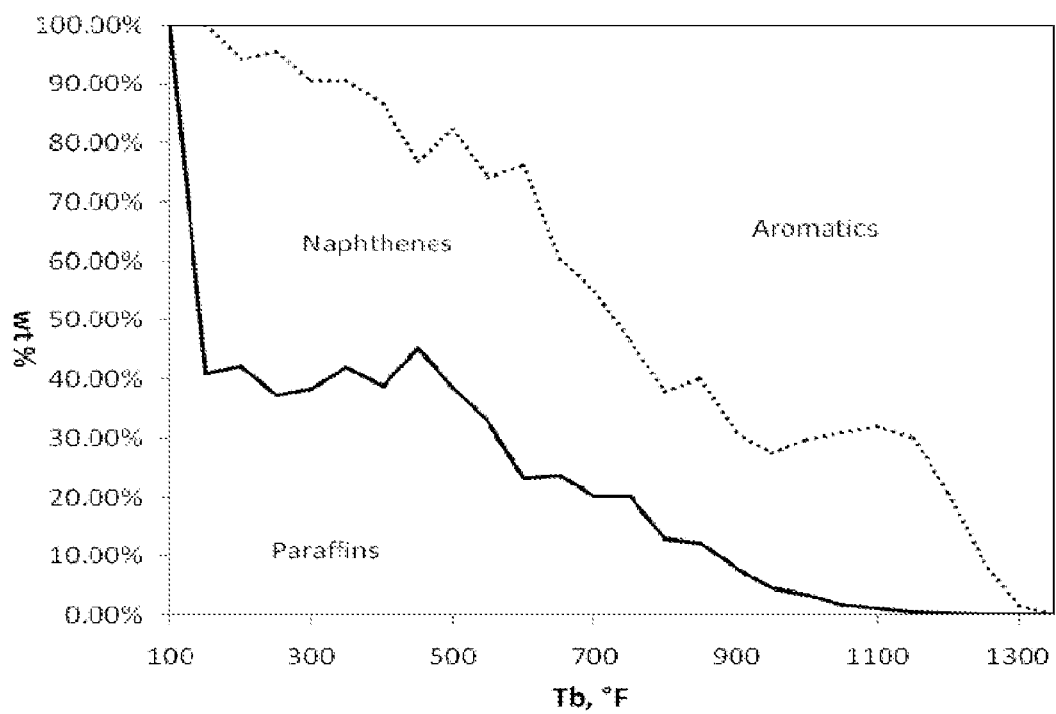
FIG. 64 is an illustration of model predictions for normalized weight percentage distributions of paraffins, naphthenes, and aromatics in whole crude versus true boiling point for the blend crude.
Figure 65:
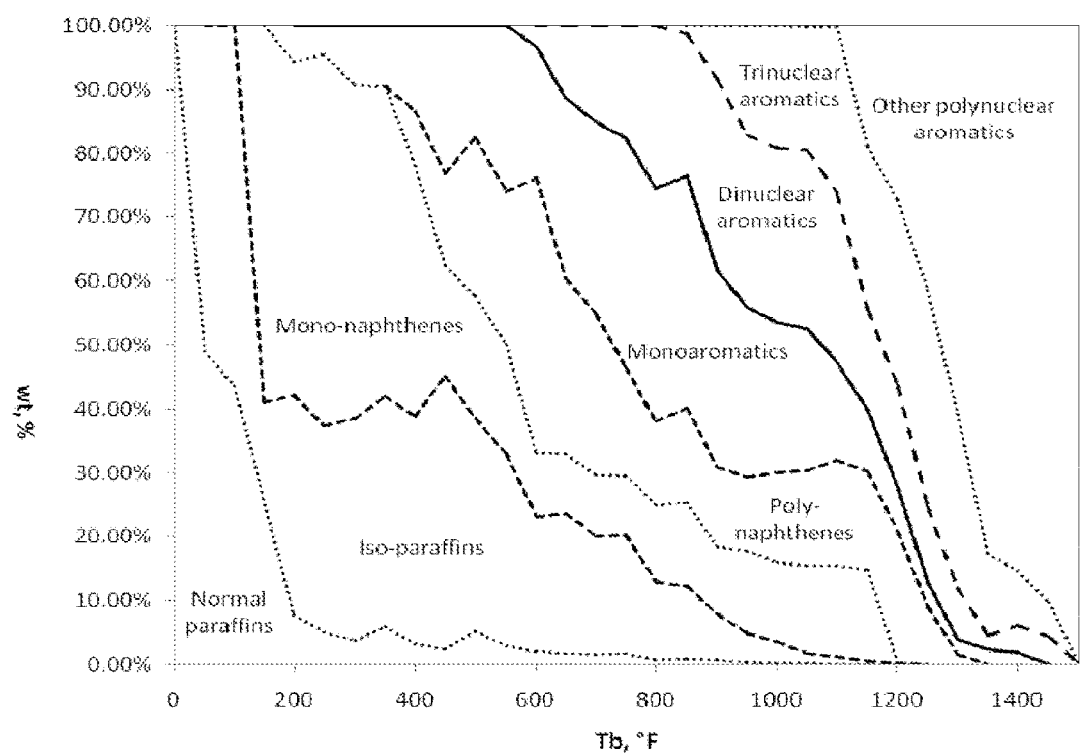
FIG. 65 is an illustration of model predictions for normalized weight percentage distributions of normal paraffins, iso-paraffins, mono-naphthenes, poly-naphthenes, monoaromatics, dinuclear aromatics, trinuclear aromatics, and other polynuclear aromatics in whole crude versus true boiling point for the blend crude.

FIG. 58 shows cumulative weight fractions of paraffins, naphthenes, and aromatics in whole crude versus carbon number. FIG. 59 shows differential weight fractions of paraffins, naphthenes, and aromatics in whole crude versus carbon number. FIG. 60 shows weight percentage distributions of paraffins, naphthenes, and aromatics in whole crude versus carbon number. FIG. 61 shows normalized weight percentage distributions of normal paraffins, iso-paraffins, mono-naphthenes, poly-naphthenes, monoaromatics, dinuclear aromatics, trinuclear aromatics, and other polynuclear aromatics in whole crude versus carbon number. FIG. 62 shows cumulative weight fractions of paraffins, naphthenes, and aromatics in whole crude versus true boiling point. FIG. 63 shows differential weight fractions of paraffins, naphthenes, and aromatics in whole crude versus true boiling point. FIG. 64 shows weight percentage distributions of paraffins, naphthenes, and aromatics in whole crude versus true boiling point. FIG. 65 shows normalized weight percentage distributions of normal paraffins, iso-paraffins, mono-naphthenes, poly-naphthenes, monoaromatics, dinuclear aromatics, trinuclear aromatics, and other polynuclear aromatics in whole crude versus true boiling point for the blend crude.

The relevant teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A computer-implemented method of determining a chemical composition of crude oil, the method comprising:
   in a processor:
   i) selecting classes of hydrocarbon constituent molecules, the classes comprising a paraffins class, a naphthenes class, and an aromatics class;
   ii) selecting, for each class segment types and a corresponding segment number range for each segment type, wherein each segment type is a molecular structural repeating unit of each class wherein:
      a) the segment types for the paraffins class comprise a zero-branch methylene group, a one-branch methylene group, and a two branch methylene group;
      b) the segment types for the naphthenes class comprise a cyclohexane side ring group, a zero-branch methylene group, and a methyl end group; and c) the segment types for the aromatics class comprise an aromatic side ring group, a cyclohexane side ring group, a zero-branch methylene group, and a methyl end group;

iii) selecting a probability distribution function for each segment type of each class and corresponding segment number range, wherein the probability distribution function has scale and shape parameters; and iv) regressing characterization data of the crude oil with the selected probability distribution function for each segment type of each class and corresponding segment number range, thereby determining the scale and shape parameters of the probability distribution function of each segment type of each class and determining a weight percent of the paraffins class, the naphthenes class, and the aromatics class; and v) outputting the determined scale and shape parameters of the probability distribution function of the segment types of each class and the determined weight percent of the paraffins class, the naphthenes class, and the aromatics class as the determined chemical composition of the crude oil.

2. The method of claim 1, further comprising estimating physical and chemical property values for each class as a function of the segment types of each class and corresponding segment number range.

3. The method of claim 1, further comprising:
estimating a chemical composition of the crude oil based on the selected probability distribution function for each segment type and the determined weight percent, and
estimating physical and chemical properties of the crude oil as a function of the estimated chemical composition.

4. The method of claim 3, wherein the estimated physical properties of the crude oil include one or more of boiling point, density, and viscosity.

5. The method of claim 3, wherein the estimated chemical properties of the crude oil include one or more of paraffin content, naphthene content, aromatic content, carbon content, hydrogen content, C/H ratio, asphaltene content, carbon residue, sulfur content, nitrogen content, and total acid number.

6. The method of claim 3, wherein determining the weight percent of the paraffins class, the naphthenes class, and the aromatics class includes matching the estimated physical and chemical properties of the crude oil against the crude oil characterization data thereby determining the weight percent.

7. The method of claim 1, wherein the physical properties of crude oil include one or more of vapor pressure, density, and viscosity.

8. The method of claim 1, wherein the chemical properties of crude oil include one or more of carbon content, hydrogen content, sulfur content, nitrogen content, and oxygen content.

9. The method of claim 1, wherein the characterization data of the crude oil includes one or more of boiling point, density, and viscosity.

10. The method of claim 9, wherein the characterization data of the crude oil further includes one or more of paraffin content, naphthene content, aromatic content, carbon content, hydrogen content, C/H ratio, asphaltene content, carbon residue, sulfur content, nitrogen content, and total acid number.

11. The method of claim 1, further comprising:
in the processor, predicting physical and chemical properties of the crude oil by representing the crude oil using the determined chemical composition of the crude oil.

12. The method of claim 11, further comprising: in the processor, using one or more of the determined chemical composition of the crude oil and the predicted physical and chemical properties of the crude oil to perform one or more of planning, scheduling, simulating, designing, optimizing, and controlling petroleum refining operations.

13. The method of claim 1, wherein the classes further comprise one or more of thiophenes, carbozoles, phenols, and naphthenic acids.

14. The method of claim 1, wherein the classes further comprise one or more of mercaptans, sulfides, and thiophenes.

15. The method of claim 1, wherein the classes further comprise one or more of carbazoles and quinolines.

16. The method of claim 1, wherein the classes further comprise one or more of phenols and carboxylic acids.

17. A method of blending crude oil, comprising the steps of:
A) in a processor, determining a chemical composition for each of two or more crude oil samples, wherein determining comprises:
i) selecting classes of hydrocarbon constituent molecules, the classes comprising a paraffins class, a naphthenes class, and an aromatics class;
ii) selecting, for each class, segment types and a corresponding segment number range for each segment type, wherein each segment type is a molecular structural repeating unit of each class, wherein:
a) the segment types for the paraffins class comprise a zero-branch methylene group, a one-branch methylene group, and a two branch methylene group;
b) the segment types for the naphthenes class comprise a cyclohexane side ring group, a zero-branch methylene group, and a methyl end group; and
c) the segment types for the aromatics class comprise an aromatic side ring group, a cyclohexane side ring group, a zero-branch methylene group, and a methyl end group;
iii) selecting a probability distribution function for each segment type of each class and corresponding segment number range, wherein the probability distribution function has scale and shape parameters; and
iv) regressing characterization data of the crude oil with the selected probability distribution function for each segment type of each class and corresponding segment number range, thereby determining the scale and shape parameters of the probability distribution function of each segment type of each class and determining a weight percent of the paraffins class, the naphthenes class, and the aromatics classes;
B) in a processor, based on said determined chemical compositions, predicting physical and chemical properties of the crude oil using the determined scale and shape parameters of the probability distribution function of the segment types of each class;
C) in a processor, determining respective ratios of the two or more crude oil samples based on the predicted physical and chemical properties, such that a resulting blend using the respective ratios of the sample crude oils has certain chemical composition and predicted physical and chemical properties; and D) forming the blend using amounts of the two or more sample crude oils in the determined respective ratios.

18. The method of claim 17, further comprising estimating physical and chemical property values for each class as a function of the segment types of each class and corresponding segment number range.

19. The method of claim 17, further comprising:
estimating a chemical composition of the crude oil based on the selected probability distribution function for each segment type and the determined weight percent, and
estimating physical and chemical properties of the crude oil as a function of the estimated chemical composition.

20. The method of claim 19, wherein the estimated physical properties of the crude oil include one or more of boiling point, density, and viscosity.

21. The method of claim 19, wherein the estimated chemical properties of the crude oil include one or more of paraffin content, naphthene content, aromatic content, carbon content, hydrogen content, C/H ratio, asphaltene content, carbon residue, sulfur content, nitrogen content, and total acid number.

22. The method of claim 19, wherein determining the weight percent of the paraffins class, the naphthenes class, and the aromatics class includes matching the estimated physical and chemical properties of the crude oil against the crude oil characterization data thereby determining the weight percent.

23. The method of claim 17, wherein the physical properties of the crude oil include one or more of vapor pressure, density, and viscosity.

24. The method of claim 17, wherein the chemical properties of the crude oil include one or more of carbon content, hydrogen content, sulfur content, nitrogen content, and oxygen content.

25. The method of claim 17, wherein the characterization data of the crude oil further includes one or more of boiling point, density, viscosity, paraffin content, naphthene content, aromatic content, carbon content, hydrogen content, C/H ratio, asphaltene content, carbon residue, sulfur content, nitrogen content, and total acid number.

26. The method of claim 17, wherein the classes further comprise one or more of thiophenes, carbozoles, phenols, and naphthenic acids.

27. The method of claim 17, wherein the classes further comprise one or more of mercaptans, sulfides, and thiophenes.

28. The method of claim 17, wherein the classes further comprise one or more of carbazoles and quinolines.

29. The method of claim 17, wherein the classes further comprise one or more of phenols and carboxylic acids.

* * * * *

UNITED STATES PATENT AND TRADEMARK OFFICE
CERTIFICATE OF CORRECTION

| | | |
|---|---|---|
| PATENT NO. | : 9,934,367 B2 | Page 1 of 1 |
| APPLICATION NO. | : 13/740095 | |
| DATED | : April 3, 2018 | |
| INVENTOR(S) | : Chau-Chyun Chen and HuiLing Que | |

It is certified that error appears in the above-identified patent and that said Letters Patent is hereby corrected as shown below:

In the Claims

In Claim 17, Column 38, Line 61, delete "class:" and insert -- class; --.

Signed and Sealed this
Twelfth Day of June, 2018

Andrei Iancu
*Director of the United States Patent and Trademark Office*